United States Patent
Lee

(10) Patent No.: US 11,773,357 B2
(45) Date of Patent: Oct. 3, 2023

(54) PERFUSION PLATE FOR MICROARRAY 3D BIOPRINTING

(71) Applicant: Cleveland State University, Cleveland, OH (US)

(72) Inventor: Moo-Yeal Lee, Pepper Pike, OH (US)

(73) Assignee: Cleveland State University, Cleveland, OH (US)

( * ) Notice: Subject to any disclaimer, the term of this patent is extended or adjusted under 35 U.S.C. 154(b) by 255 days.

(21) Appl. No.: 17/078,742

(22) Filed: Oct. 23, 2020

(65) Prior Publication Data

US 2021/0123007 A1    Apr. 29, 2021

Related U.S. Application Data

(60) Provisional application No. 62/926,022, filed on Oct. 25, 2019.

(51) Int. Cl.
| | | |
|---|---|---|
| C12M 3/00 | (2006.01) | |
| C12M 1/12 | (2006.01) | |
| C12M 1/00 | (2006.01) | |
| G01N 33/50 | (2006.01) | |
| C12M 1/32 | (2006.01) | |
| C12N 5/071 | (2010.01) | |

(52) U.S. Cl.
CPC ............ *C12M 21/08* (2013.01); *C12M 23/06* (2013.01); *C12M 23/12* (2013.01); *C12M 23/20* (2013.01); *C12M 23/22* (2013.01); *C12M 23/58* (2013.01); *C12M 25/06* (2013.01); *C12M 29/10* (2013.01); *C12N 5/0671* (2013.01); *G01N 33/5014* (2013.01); *G01N 33/5088* (2013.01)

(58) Field of Classification Search
CPC ...... C12M 21/08; C12M 23/06; C12M 23/12; C12M 23/20; C12M 23/22; C12M 23/58; C12M 25/06; C12M 29/10; C12N 5/0671; G01N 33/5014; G01N 33/5088
See application file for complete search history.

(56) References Cited

U.S. PATENT DOCUMENTS

| | | | |
|---|---|---|---|
| 4,871,647 | A | 10/1989 | Komamura et al. |
| 7,332,328 | B2 | 2/2008 | Webb et al. |
| 10,934,538 | B2 | 3/2021 | Lee |
| 11,390,836 | B2 * | 7/2022 | Lee .............. C12M 23/12 |
| 2011/0152128 | A1 | 6/2011 | Herrmann et al. |
| 2014/0141503 | A1 | 5/2014 | Hong et al. |
| 2015/0086445 | A1 | 3/2015 | Lee et al. |
| 2018/0014219 | A1 | 5/2018 | Lee |
| 2018/0142195 | A1 * | 5/2018 | Lee .............. C12M 29/10 |

FOREIGN PATENT DOCUMENTS

| | | |
|---|---|---|
| WO | 2007/053561 | 5/2007 |
| WO | 2017/123722 | 7/2017 |
| WO | 2018/094194 | 5/2018 |

OTHER PUBLICATIONS

Lohasz et al. Scalable Microfluidic Platform for Flexible Configuration of and Experiments with Microtissue Multiorgan Models. SLAS Technology. 2019, 24(1): 79-95. (Year: 2019).*
Langhans. Three-Dimensional in Vitro Cell Culture Models in Drug Discovery and Drug Repositioning. Front. Pharmacol. 2018; 9: 6. (Year: 2018).*
Lin et al. A Microfluidic Platform for High-throughput Single-cell Isolation and Culture. J. Vis. Exp. 2016; 112: e54105. (Year: 2016).*
Joshi, P., Yu, K.N., Kang, S.Y., Kwon, S.J., Kwon, P.S., Dordick, J.S., Kothapalli, C.R., and Lee, M.Y., 3D-cultured neural stem cell (NSC) microarrays on a micropillar chip for high-throughput developmental neurotoxicology, Experimental Cell Research, 370, 680-691, DOI: 10.1016/j.yexcr.2018.07.034 (2018).
Yu, K.N., Kang, S.Y., Hong, S., and Lee, M.Y., High-throughput metabolism-induced toxicity assays demonstrated on a 384-pillar plate, Archives of Toxicology, 92, 2501-2516, DOI: 10.1007/s00204-018-2249-1 (2018).
Roth, A.D., Lama, P., Dunn, S., Hong, S., and Lee, M.Y., Polymer coating on a micropillar chip for robust attachment of PuraMatrix peptide hydrogel for 3D hepatic cell culture, Materials Science and Engineering C, 90, 634-644, doi.org/10.1016/j.msec.2018.04.092 (2018).
Joshi, P., Datar, A., Yu, K.N., Kang, S.Y., and Lee, M.Y., High-content imaging assays on a miniaturized 3D cell culture platform, Toxicology In Vitro, 50, 147-159, doi: 10.1016/j.tiv.2018.02.014 (2018).
Lee, D.W., Kang, J.H., Hwang, H.J., Oh, M.S., Shin, B.C., Lee, M.Y., and Kuh, H.J., Pitch-tunable pillar arrays for high-throughput culture and immunohistological analysis of tumor spheroids, RSC Advances, 8, 4494-4502 (2018) S. Yu, S., Joshi, P., Park, Y.J., Yu, K.N., and Lee, M.Y., Deconvolution of images from 3D printed cells in layers on a chip, Biotechnology Progress, 34(2), 445-454, DOI 10.1002/btpr.2591 (2018).

(Continued)

*Primary Examiner* — Arthur S Leonard
*Assistant Examiner* — Jianjian Zhu
(74) *Attorney, Agent, or Firm* — Calfee, Halter & Griswold LLP

(57) ABSTRACT

A perfusion plate that can be combined with pillar plates containing cell layers is disclosed. The perfusion plate can have an inflow reservoir and an outflow reservoir connected by at least one channel, which fluidly connects the perfusion wells to the reservoirs for the flow of a fluid such as growth media. A perfusion plate can be part of an assembly containing a pillar plate, a lid, and a transparent bottom for visualizing cell growth in the perfusion wells. The perfusion-pillar plate assembly can facilitate perfusion-based tissue culture and tissue communication for high throughput, high-content, drug screening.

9 Claims, 39 Drawing Sheets

(56) References Cited

OTHER PUBLICATIONS

Yu, S., Joshi, P., Park, Y.J., Yu, K.N., and Lee, M.Y., Deconvolution of images from 3D printed cells in layers on a chip, Biotechnology Progress, 34(2), 445-454, DOI 10.1002/btpr.2591 (2018).

Yu, K.N., Nadanaciva, S.N., Rana, P., Lee, D.W., Ku, B.S., Roth, A.D., Dordick, J.S., Will, Y., and Lee, M.Y., Prediction of metabolism-induced hepatotoxicity on three-dimensional hepatic cell culture and enzyme microarrays, Archives of Toxicology, 92(3), 1295-1310, doi.org/10.1007/s00204-017-2126-3 (2018).

Lee, D.W., Oh, W.Y., Yi, S.H., Ku, B.S., Lee, M.Y., Cho, Y.H., and Yang, M.H., Estimation of bisphenol A—Human toxicity by 3D cell culture arrays, high throughput alternatives to animal tests, Toxicology Letters, 259, 87-94 (2016).

Kang, J.H., Lee, D.W., Hwang, H.J., Yeon, S.E., Lee, M.Y., and Kuh, H.J., Mini-pillar array for hydrogel-supported 3D culture and high-content histologic analysis of human tumor spheroids, Lab on a Chip, DOI: 10.1039/c6lc00526h (2016).

Lee, D.W., Lee, M.Y., Ku, B.S., and Nam, D.H., Automatic 3D cell analysis in high-throughput microarray using micropillar and microwell chips, Journal of Biomolecular Screening, 20(9), 1178-1184 (2015).

Lee, D.W., Choi, Y.S., Seo, Y.J., Lee, M.Y., Jeon, S.Y., Ku, B.S., Kim, S.J., Yi, S.H., and Nam, D.H., High-throughput, miniaturized clonogenic assay on a micropillar/microwell chip with brain tumor cells isolated from patients, Small, 10 (24), 5098-5105 (2014).

Kwon, S.J., Lee, D.W., Shah, D.A., Ku, B.S., Jeon, S.Y., Solanki, K., Ryan, J.D., Clark, D.S., Dordick, J.S., and Lee, M.Y., High-throughput and combinatorial gene expression on a chip for metabolism-induced toxicology screening, Nature Communications, 5:3739 DOI: 10.1038/ncomms4739 (2014).

Lee, D.W., Choi, Y.S., Seo, Y.J., Lee, M.Y., Jeon, S.Y., Ku, B.S., Kim, S.J., Yi, S.H., and Nam, D.H., High-throughput screening (HTS) of anticancer drug efficacy on a micropillar/microwell chip platform, Analytical Chemistry, 86(1), 535-542 (2014).

Lee, D.W., Lee, M.Y., Ku, B.S., Yi, S.H., Ryu, J.H., Jeon, R., and Yang, M.H., Application of the DataChip/MetaChip technology for the evaluation of ajoene toxicity in vitro, Archives of Toxicology, 88(2), 283-290 (2014).

Lee, D.W., Yi, S.H, Jeong, S.H., Ku, B.S., Kim, J.G., and Lee, M.Y., Plastic pillar inserts for three-dimensional (3D) cell cultures in 96-well plates, Sensors and Actuators B, 177(1), 78-85 (2013).

U.S. Appl. No. 62/570965, filed 2017.

* cited by examiner

See FIG. 7E

See FIG. 7F

PERFUSION PLATE FOR MICROARRAY 3D BIOPRINTING

CROSS-REFERENCE TO RELATED APPLICATIONS

This application claims priority to and the benefit of U.S. Provisional Patent Application No. 62/926,022, filed Oct. 25, 2019, the entire content of which are incorporated by reference herein.

STATEMENT REGARDING FEDERALLY SPONSORED RESEARCH

The inventive subject matter described herein was made with U.S. Government support under NIH/NIEHS grant no. R01ES025779; EPA Transform Tox Test Challenge grant; TeCK Fund/TVSF grant; and NIH/NIDDK grant no. UG3DK119982. The government has certain rights in the invention.

TECHNICAL FIELD

The subject matter described herein relates generally to a perfusion plate, perfusion plate assembly, and method of using a perfusion plate to grow cellular tissues. More specifically, the inventive subject matter described herein relates to using a microfluidic flow perfusion plate having a certain geometry to its growth media reservoirs and fluid flow microchannels and perfusion wells to support growth of 3D printed miniature cell constructs that are 3D printed on a pillar plate.

BACKGROUND

When developing therapeutic drugs, it is important to determine a drug's safety and efficacy. In the relatively early stages of drug development, drug safety and efficacy are often tested outside the living organism ("in vitro"). The in vitro assays currently available, however, using 2D cell monolayers or 3D cell spheroids, do not adequately mimic how drugs act in the living organism ("in vivo"). Thus, an in vitro cell or tissue model that can closely mimic the corresponding tissues in vivo and systematically simulate diseases is desired.

3D bioprinting is a promising technology in this regard. Generally, 3D bioprinting refers to robotically dispensing cells layer-by-layer in hydrogels, thus creating relatively largescale tissue constructs that more accurately mimic the in vivo environment. But because the tissue constructs are generally on a large scale, 3D bioprinting is not ideal for high throughput testing, and is thus limited as an alternative to the currently available in vitro assays. Recently, a method of microarray 3D bioprinting was developed, which allows for high throughput testing.

Microarray 3D bioprinting refers to dispensing very small amounts of cells along with other biological samples such as hydrogels, growth factors, extracellular matrices, biomolecules, drugs, DNAs, RNAs, viruses, bacteria, growth media, or combinations thereof, on a microwell/micropillar plate using a microarray spotter and then incubating the cells to create a mini-bioconstruct. This technology can potentially revolutionize tissue engineering and disease modeling for screening therapeutic drugs and studying toxicology.

Since microwell/micropillar plates (also known as "microwell/micropillar chip platforms" and "microarray biochips") contain arrays of up to 5,000 microwells/micropillars, this method is ideal for high throughput testing. However, the currently available microwell/micropillar plates are not ideal for constructing mini-tissues due to the limited space available on the micropillar plate or limited control of individual experimental conditions in the microwell chip.

For example, currently available micropillar plates use pillars with flat tops, which are not conducive to dispensing cells layer-by-layer. Thus, it is difficult to carry out 3D bioprinting on micropillar plates. In addition, the currently available microwell chips use wells that trap air bubbles in the hydrogel as the cell layers are printed. In addition, it is difficult to control each bioprinted tissue construct individually in the microwell chip because all tissue constructs in the microwell chip should be immersed in a petri dish with a universal growth medium. Thus, there is a need for designing a new structure of pillar-microwell on a chip that can facilitate layered cell printing on both the pillar and well, ensure robust cell spot attachment for high-content imaging and immunofluorescent assays, and avoid air bubble entrapment for robust 3D cell/tissue cultures.

In addition, currently available perfusion plates rely on a pump or a rocker plate to convey growth media or other fluid from one end of the perfusion plate to the other, to culture the cells in the perfusion wells. The current perfusion plates must also be attended to with regularity, sometimes as often as every three hours or more often. Additionally, there is a need to provide an improvement to imaging cells that are positioned in perfusion wells with nonconventional cell imaging devices. Thus, there is a need for a new perfusion plate that is complementary to the pillar-microwells and micropillars on a chip and does not rely on a rocker plate, pump, or other power-based mechanism for perfusing the growth media to the cells, and that can be left unattended for longer periods of time.

SUMMARY

The present disclosure is directed to a perfusion plate. The perfusion plate can include a base having a first major surface and a second major surface. The perfusion plate can include at least one perfusion well positioned in the base. The perfusion plate can include a first reservoir and a second reservoir each positioned in the base. The perfusion plate can include at least one channel, where the channel extends along at least a portion of the base under the perfusion well and fluidly connects the first reservoir to the second reservoir, and the channel is fluidly connected to the perfusion well. The perfusion plate can include a transparent plate attached to a bottom of the base.

In various embodiments, at least one reservoir and the at least one channel are coated with a hydrophilic material. In various embodiments, the hydrophilic material is one or more of: amphiphilic polymers, including poly(maleic anhydride-alt-1-octadecene) (PMA-OD), poly(maleic anhydride-alt-1-tetradecene) (PMA-TD), and polyethylene oxide-maleic anhydride copolymers, including ACM1510, ADM1510, AEM1510, AKM0530, and AKM1510, amphiphilic surfactants, including Brij C2 and C10, hydrogels, including alginate, collagen, PuraMatrix, fibrinogen, fibronectin, and Matrigel, and other hydrophilic polymers, including polydopamine, poly(2-hydroxyethyl methacrylate) (pHEMA), and poly-L-lysine (PLL). In various embodiments, the transparent plate is one of a thin glass slide or a plastic film. In various embodiments, the at least one perfusion well is sized to fit at least one pillar of a pillar plate within the perfusion well. In various embodiments, the at least one perfusion well comprises a plurality of perfusion wells, wherein each perfusion well is fluidly connected to an adjacent perfusion well by the at least one channel. In various embodiments, the at least one perfusion well comprises an array of multiple rows of perfusion wells, each row comprising a plurality of perfusion wells, wherein the perfusion wells of each row are fluidly connected to an adjacent perfusion well in that row by the at least one channel.

The present disclosure is also directed to a perfusion plate assembly including a perfusion plate, a pillar-microwell plate that has at least one pillar attached at a first end to the pillar-microwell plate and a microwell accessible from a second end of the pillar; a transparent plate secured to a bottom of the perfusion plate; and a lid to cover the perfusion plate when the pillar-microwell plate is attached to the perfusion plate.

The present disclosure is also directed to a method of operating a perfusion well plate, including the steps of (1) depositing cells into at least one pillar-microwell on a pillar plate by direct cell printing or transferring cell aggregates from an ultralow attachment (ULA) well plate; (2) submerging the at least one pillar having cells into at least one perfusion well in a perfusion plate; (3) adding a first volume of media fluid to a first reservoir and incubating the perfusion plate and pillar plate in an incubator; (4) after a first designated amount of time has elapsed, adding a second volume of fluid to the first reservoir to generate a unidirectional flow; and (5) after a second designated amount of time has elapsed, emptying the second reservoir and adding a third volume of fluid to the first reservoir. In other exemplary methods, the pillar plate can be rotated 90 degrees after a specified amount of time. In exemplary methods, a plurality of inflow reservoirs can be filled with various fluids, such as tissue-specific growth medias, which flow to the corresponding plurality of outflow reservoirs. In various embodiments, the step of depositing cells into at least one pillar-microwell is done by sandwiching a well plate having cells incubated within its wells with a pillar plate with hydrogel, inverting the sandwiched well plate and pillar plate for cell precipitation and encapsulation, and removing the well plate. In various embodiments, the cells further comprise a second type of cells, and the at least one pillar-microwell further comprises at least a second row of pillar-microwells, and further comprising the step of depositing the second type of cells into the pillar-microwells of the second row.

The present disclosure is also directed to a method of operating a perfusion plate having perfusion wells, including the steps of adding a liquid to a first reservoir at a tilted angle; aspirating out excess liquid collected in a second reservoir; adding a first volume of growth media to the first reservoir to remove remaining liquid in reservoirs, channels, and perfusion wells; aspirating excess growth media collected in the second reservoir; repeating the steps of adding and aspirating growth media two more times; depositing cells into at least one pillar-microwell on a pillar plate; submerging the at least one pillar having cells into at least one perfusion well in a perfusion plate; adding a second volume of growth media to a first reservoir and incubating the perfusion plate and pillar plate in a $CO_2$ incubator for cell culture; after a first designated amount of time has elapsed, adding a third volume of growth media to the first reservoir to generate slow, unidirectional flow; and after a second designated amount of time has elapsed, emptying the second reservoir and adding a fourth volume of growth media to the first reservoir.

The present disclosure is also directed to a method of loading cells from a well plate to a pillar plate. The method can include the step of loading cells into a plurality of wells on a well plate. The method can include the step of adding a hydrogel to a plurality of pillar-microwells on a pillar plate. The method can include the step of sandwiching a plurality of pillars on the pillar plate into the wells of the well plate. The method can include the step of inverting the well plate and the pillar plate. The method can include the step of removing the well plate from the pillar plate. The method can include the step of sandwiching the pillar plate with a second well plate having at least one well. The method can include the step of waiting for cell precipitation and encapsulation to occur. The method can include the step of removing the pillar plate from the second well plate. The method can include the step of rotating the pillar plate 90 degrees. The method can include the step of sandwiching the pillars of the pillar plate with the wells of the second pillar plate. In various embodiments, the second well plate is one of an ultralow attachment (ULA) plate, a microtiter plate, and a perfusion plate. In various embodiments, the cells remain incubated. In various embodiments, the well plate is one of a ULA plate, a microtiter plate, and a perfusion plate. In various embodiments, the cells loaded into the wells of the well plate comprise one or more of: human and animal cells, microbials, fungi, yeasts, and viruses.

These and other features, aspects, and advantages of the general inventive concepts will become better understood with reference to the following description and appended claims.

BRIEF DESCRIPTION OF THE DRAWINGS

The subject matter of the present disclosure is particularly described and distinctly claimed in the concluding portion of the specification. A more complete understanding of the disclosure, however, may best be obtained by referring to the detailed description and claims when considered in connection with the figures, wherein like numerals denote like elements.

DETAILED DESCRIPTION

Figure 1A:
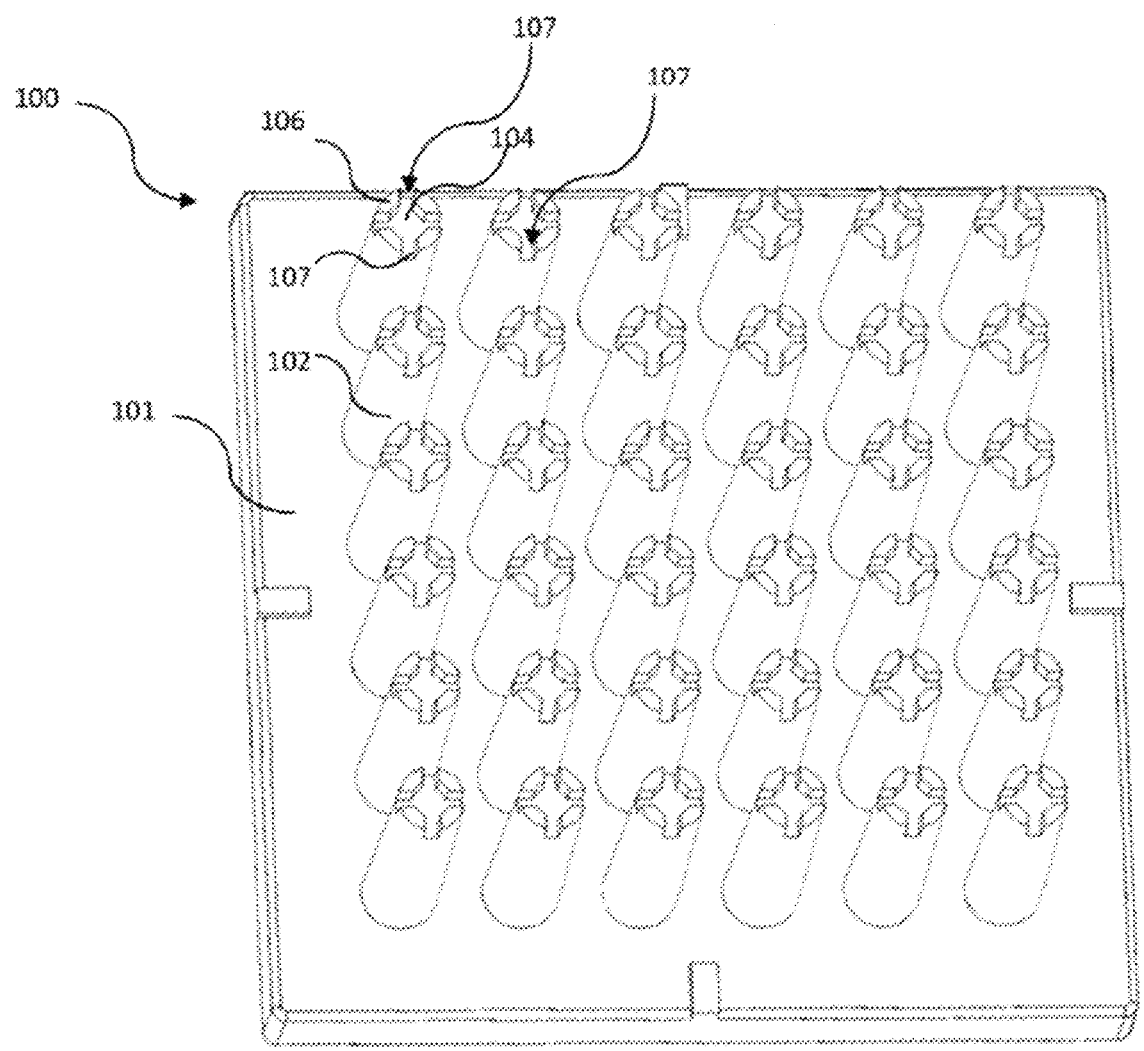
FIG. 1A shows a perspective view of an embodiment of a pillar-microwell (e.g., a pillar with four sidewalls and four slits) plate.

While various exemplary embodiments and methods are described herein, other embodiments, methods, and materials similar or equivalent to those described herein are encompassed by the general inventive concepts. All references cited herein, including published or corresponding U.S. or foreign patent applications, issued U.S. or foreign patents, and any other references, are each incorporated herein by reference in their entireties, including all data, tables, figures, and text presented in the cited references.

Unless defined otherwise, all technical and scientific terms used herein have the same meaning as commonly understood by one of ordinary skill in the art to which the invention belongs.

All percentages, parts, and ratios as used herein are by weight of the total formulation, unless otherwise specified. All such weights as they pertain to listed ingredients are based on the active level and, therefore, do not include solvents or by-products that can be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

The methods and embodiments of the present disclosure can comprise, consist of, or consist essentially of the essential elements of the disclosure as described herein, as well as any additional or optional element described herein or which is otherwise useful in carrying out the general inventive concepts.

To the extent that the terms "includes," "including," "contains," or "containing" are used in the specification or the claims, they are intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

All combinations of method or process steps as used herein can be performed in any order, unless otherwise specified or clearly implied to the contrary by the context in which the referenced combination is made.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, and 10) contained within the range.

When it comes to creating human organoids in a high-throughput screening (HTS) system, there are two different approaches typically taken: (1) differentiating pluripotent stem cells (PSCs) in hydrogels into human organoids in low-throughput platforms (e.g., 6-/24-well plates, petri dishes, and spinner flasks) and then isolating mature organoids and dispensing in a HTS system and (2) dispensing PSCs in hydrogels in a HTS system and differentiating into human organoids in situ. The former case is easier for HTS assays when mature organoids are "small" (below 100 µm in diameter) and uniform in size and shape for consistent dispensing in hydrogels using automated liquid handling machines. Except for tumor organoids derived from biopsy samples, mature organoids are typically 200 µm-2 mm in diameter, difficult to dispense consistently into high-density well plates, and hard to passage by using proteolytic and collagenolytic enzymes due to low cell viability after dissociation. Therefore, mechanical dissociation methods are commonly introduced for passaging mature organoids, which can lead to irregular organoids in size and difficulty in robotic dispensing. The latter case is more robust in terms of dispensing PSCs, but less convenient for HTS assays due to difficulty in changing growth media frequently without disturbing cells in hydrogels in high-density well plates.

The general concepts described in various embodiments herein are directed to miniature three-dimensional (3D) bioprinting technology for creating multiple human tissue/organoid arrays on microarray biochip platforms including a micropillar plate, a 384-pillar plate with a flat tip surface, a 384-pillar plate with sidewalls and slits (384PillarPlate), a clear-bottom, 384-deep well plate ("384DeepWellPlate") for static organoid culture, a 36-pillar plate with sidewalls and slits (36PillarPlate), and its complementary 36-perfusion well plate with reservoirs and microchannels (36PerfusionPlate).

The perfusion well plate can have any number of perfusion wells as long as there are at least enough perfusion wells to accommodate the pillar-microwells (i.e., multiple pillars, each pillar with sidewalls and slits) on the pillar plate. For example, a 36PerfusionPlate can be paired with a 36PillarPlate. Human cells including primary adult cells, stem cells, and primary cancer cells can be mixed with biomimetic hydrogels (e.g., alginate, Matrigel, Geltrex, collagen, PuraMatrix, gelatin, etc.), dispensed on the pillar plates precisely with a bioprinter, and cultured in 3D to mimic tissue morphology in vivo. Cell aggregates created by using ultralow attachment (ULA) well plates (e.g., commercially available ULA 96-well plate and ULA 384-well plate) can be transferred by sandwiching the pillar plates with biomimetic hydrogels onto the ULA plates with cell aggregates and inverting the sandwiched plates for rapid cell encapsulation and organotypic 3D cell culture. After cell loading and hydrogel gelation, the pillar plates containing various cell types such as brain, liver, pancreas, intestine, etc. can be engaged with microtiter well plates (e.g., 36-well plate, 96-well plate, 384-well plate, etc.) for static cell culture or perfusion well plates (e.g., 36-perfusion well plate, 96-perfusion well plate, 384-perfusion well plate, etc.) for perfusion cell culture. The number of wells in the well plates and/or perfusion well plates can be any number for which the geometry of the wells connected to the microchannels and reservoirs permits unidirectional and bidirectional flows of fluid through the channels from one reservoir to another. Bioprinted tissues/organoids on the pillar plate can be tested with compounds, stained with fluorescent dyes, and scanned with an automated fluorescent microscope or a microtiter plate reader for high-content imagining (HCI) of tissue functions as well as predictive assessment of drug efficacy and toxicity.

In various embodiments, the pillar plates and perfusion plates described herein utilize "3D bioprinting" with "microfluidic-like" features to offer several advantages over conventional static 3D cell culture models and dynamic microphysiological system (MPS) models. The pillar plates can allow users to dispense cells and aggregates suspended in biomimetic hydrogels via 3D bioprinting and provide a high-throughput capability by controlling individual pillars with printed organoids. Multiple cell arrays demonstrated in microfluidic chambers in MPSs cannot be controlled individually, resulting in low throughput. It is highly flexible so that organoids on the pillar plates can be cultured statically and tested dynamically (or vice versa) by simply separating the pillar plate and sandwiching onto the deep well plate or the perfusion well plate.

In addition, the perfusion well plate can allow connection of multiple organoid types on the pillar plate without using micropumps and tubes, which is a critical feature for modeling complex diseases.

Furthermore, the pillar/perfusion plates can be compatible with standard 384-well plates and existing HTS equipment such as automated fluorescence microscopes and microtiter well plate readers already available in laboratories. Bioprinted organoids with key organ functions can be analyzed on the pillar/perfusion plates by in situ tissue clearing and high-throughput, high-content cell imaging. Thus, there is high potential for adopting the pillar/perfusion plate platforms with human organoids for predictive compound screening. Conventional perfusion plates developed are unsuited for the pillar plate assembly, which limit rapid perfusion culture of bioprinted tissues/organoids.

To overcome the problems associated with static culture creation of biomimetic human tissues created in vitro, and create a high-throughput perfusion platform more compatible with in vivo microenvironments, a perfusion well plate according to the exemplary embodiments described herein can be combined with pillar plates comprising organotypic cell layers and facilitate perfusion-based tissue culture and tissue communication for high-throughput, high-content, drug screening without using micropumps and tubes.

The perfusion plates described in various embodiments herein overcome the lack of unilateral flow that occurs with conventional perfusion plates, and also solves the problem of having to change the fluid frequently, by permitting longer periods of time between fluid changes. The perfusion plates described in various embodiments herein also solve the problem of viewing the cells during use by permitting imaging through a transparent plate, and can be compatible with unique pillar plates, including 36-, 96-, and 384-pillar plates.

The exemplary embodiments of a perfusion plate described herein can provide predictive assessment of drug toxicity efficacy and pharmacokinetics for preclinical evaluations; human disease modeling on bioprinted tissue constructs; systematic study of cellular microenvironments for tissue engineering and regenerative medicines; and high-throughput, high-content screening of drug candidates and environmental toxicants. The embodiments described herein can provide rapid creation of human tissue constructs with miniature 3D printing; facilitate perfusion-based tissue culture with cell layers printed on a pillar plate; and facilitate perfusion-based tissue culture with cell aggregates transferred from a ULA well plate. The embodiments described herein having a nonadherent surface coating can reduce 2D cell growth and can provide a microfluidic growth medium flow without the use of syringe pumps, micropumps, and/or rockers. The embodiments described herein can facilitate tissue communication by rotating the pillar plate with multiple bioprinted tissues and engaging it with the perfusion well plate; cell aggregates can be grown to save resources such as human cells, growth factors, and extracellular matrices. The embodiments described herein can provide a high throughput, systematic study of cellular microenvironments for tissue engineering and regenerative medicines, and a high-throughput, high-content imaging of miniaturized human tissue constructs for mechanistic studies. The perfusion well plates can be manufactured using any conventional manufacturing process, including 3D printing and plastic injection molding. In various embodiments, the pillar and perfusion plates described herein can be manufactured via injection molding of polystyrene, which is non-cytotoxic and minimizes nonspecific adsorption of compounds.

Pillar Plate

Figure 1B:
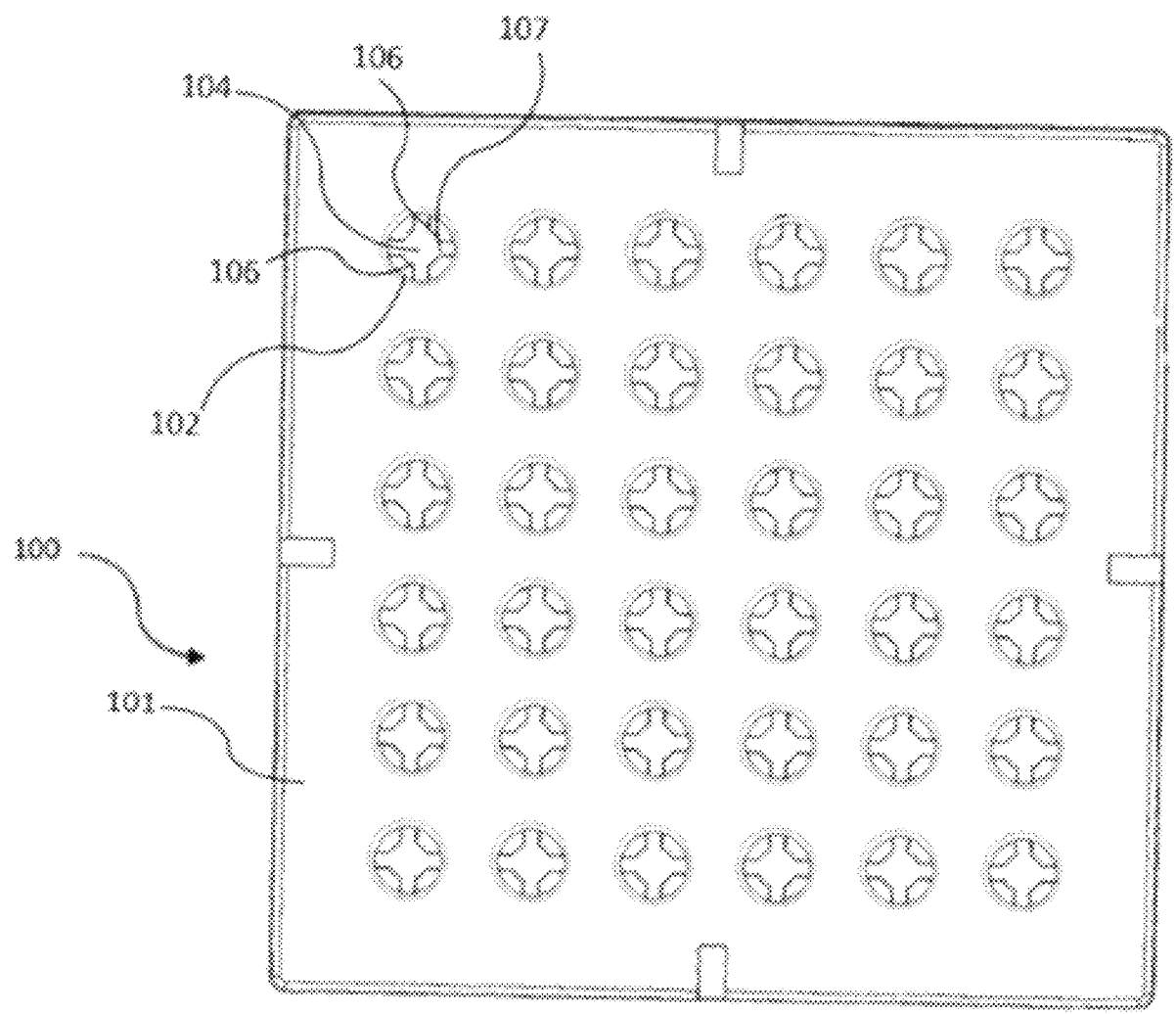
FIG. 1B shows a top-down view of the embodiment of a pillar-microwell plate of FIG. 1A.
Figure 3:
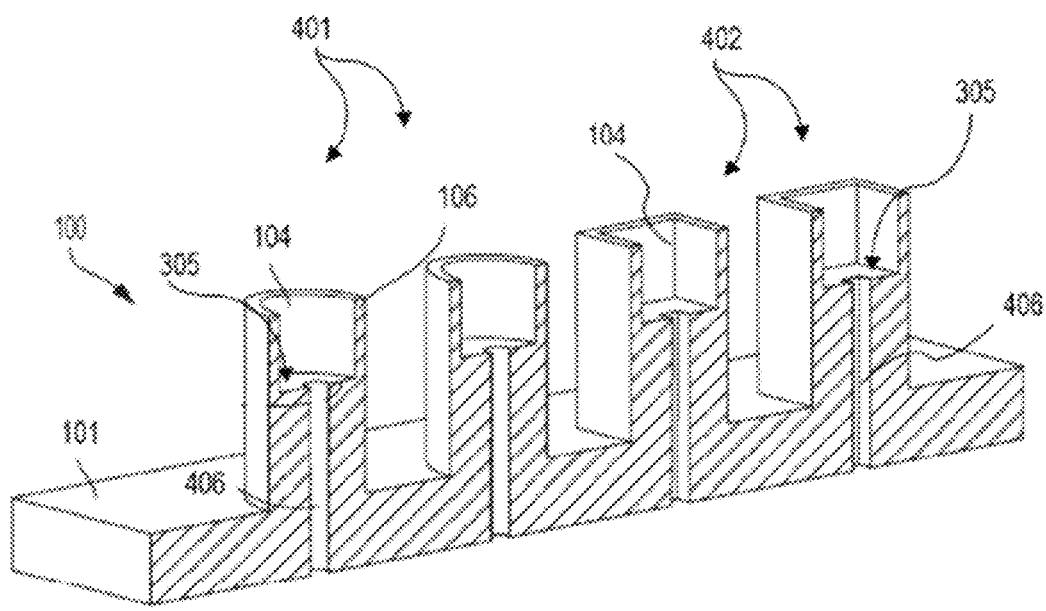
FIG. 3 shows a sectional view of various embodiments of pillar-microwells on a pillar plate.

Referring now to FIGS. 1A-1B, a pillar plate 100 according to an exemplary embodiment is illustrated. The pillar plate 100 can have pillars 102, each having a pillar-microwell 104 (i.e., pillar with sidewalls and slits) in the upper region of each pillar. The pillar-microwell 104 can also be referred to as wells or microwells on pillars. The pillars 102 can be arranged in a square array, such as 6 pillars by 6 pillars, to form a 36-pillar array. The pillar plate 100 can have greater than 36 pillars. For example, in another exemplary embodiment the pillar plate 100 can have 256 pillars, arranged in a 16 pillar by 16 pillar square array. In various embodiments, the pillar plate 100 can be a 96 pillar array, a 144 pillar array, a 384 pillar array, or a 1536 pillar array. The pillar-microwells 104 in FIG. 1A have a cylindrical geometry with one or more slits 107 cut into the sidewall 106 of the upper portion of the cylinder. There can be four slits, as shown in FIG. 1A, but the number of slits can vary. Referring now to FIG. 1B, a top-down view of the pillar plate 100 is shown, and the slits 107 extending from each microwell 104 to an exterior wall of a pillar 102 are illustrated. The depth of the pillar-microwells 104 does not extend the full height of the pillar 102 in which each microwell is situated. The pillars 102 are all connected to the pillar plate 100 at the base of each pillar 102. Referring now to FIG. 3, the microwell 104 of each pillar 102 can have a cylindrical geometry, an elongate square shaped geometry, or any other suitable geometry.

Referring back to FIG. 1B, the pillar plate 100 comprises a chip base 101 and at least one pillar 102. The pillars 102 can be micropillars. In some exemplary embodiments, the pillar plate 100 contains arrays of pillars 102, for example, about 90 to about 5,000 pillars. The pillar 102 can be any shape depending on the needs of the test. An embodiment of a pillar plate 100 containing an array of 36 pillars is depicted in FIGS. 1A and 1B. In other exemplary embodiments, the array can be of 384 pillars, or 256 pillars. In still other exemplary embodiments, the array can be of 96, 384, or 1536 pillars, or any commonly used configuration of pillars known in the field.

In some exemplary embodiments, the pillar 102 is between about 0.3-5 mm in width, about 0.3-5 mm in length, and about 1-20 mm in height. In various embodiments, the pillar 102 can be from about 0.3-5 mm in diameter and 1-20 mm in height. For example, a pillar 102 can be 2.6 mm in diameter and 13.5 mm in height.

Figure 2:
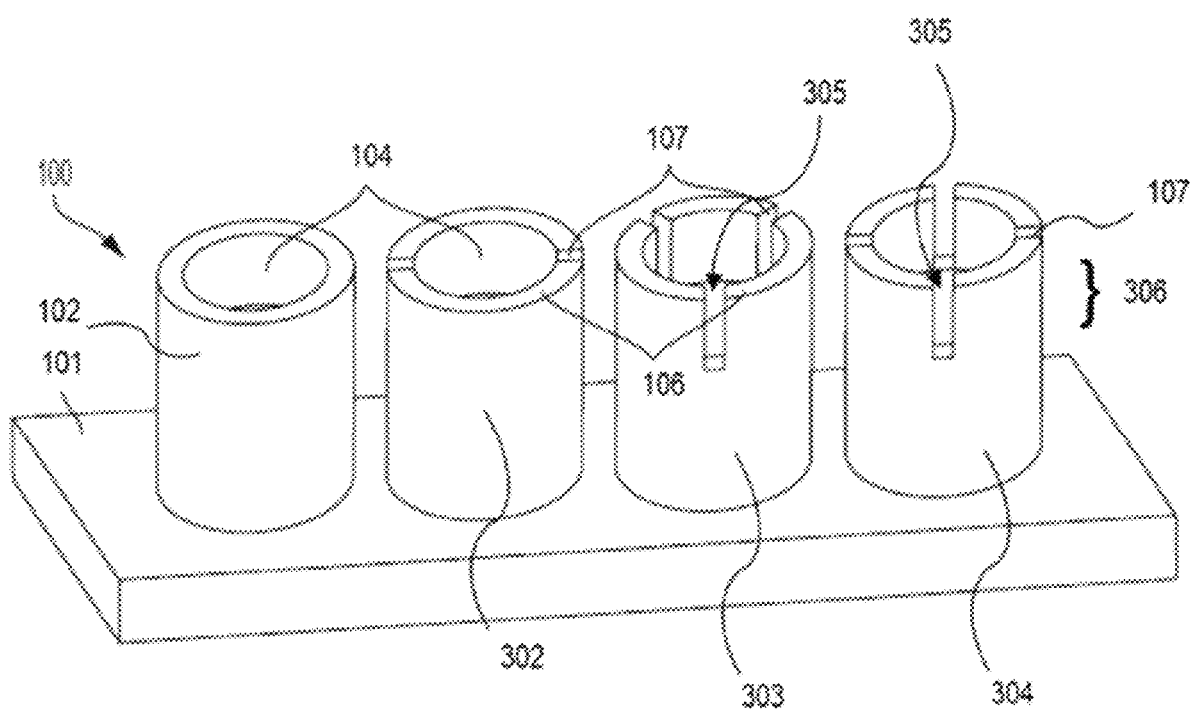
FIG. 2 shows a sectional view of various embodiments of pillar-microwells on a pillar plate.

Referring to FIG. 2, unlike conventional micropillars that have flat tops, the inventive pillar 102 comprises a top end 306 that comprises a pillar-microwell 104. The pillar-microwell 104 comprises a reservoir with a pillar-microwell base 305 and at least one sidewall 106. The pillar-microwell 104 can extend from the top end 306 of the pillar 102 to the pillar-microwell base 305. The pillar-microwell base 305 can be located between the chip base 101 and pillar top end 306. In various embodiments, the pillar-microwell 104 can hold any volume of sample, including 1-8 μL. The sidewall 106 can be between about 0.1-5 mm in height and about 0.2-1 mm in thickness. The pillar-microwell sidewall 106 can facilitate layer-by-layer cellular printing and robust cell spot attachment.

In some exemplary embodiments, the pillar plate 100 comprises a means for minimizing air bubble entrapment. For example, in some exemplary embodiments, the pillar-microwell sidewall 106 can contain at least one slit 107. The slit 107 is a gap in the sidewall 106 that extends at least partway through the width of the sidewall. In some further exemplary embodiments, the pillar-microwell sidewall 106 can contain 1-5 slits 107, or more. This particular geometry and/or the hydrophilic coating can prevent air bubble entrapment in the pillar-microwell 104.

Referring to FIG. 2, a row of exemplary pillars 102 with pillar-microwells 104 is shown. The pillars 102 are cylindrical and have cylindrical shaped pillar-microwells 104. Each pillar-microwell 104 has a microwell base 305 at the bottom of the pillar-microwell 104. Various embodiments of slits 107 in the sidewall 106 is illustrated in FIG. 2. A first pillar 102 has no slits 107; a second pillar 302 has two slits 107 offset from each other by 180 degrees; a third pillar 303 has three slits 107 offset from each adjacent slit by 120 degrees, and a fourth pillar 304 has four slits 107 offset from each adjacent slit by 90 degrees.

Referring now to FIG. 3, a cross-section of a row of exemplary embodiments of a pillar plate 100 having pillars on a chip base 101 is illustrated. The pillars can be cylindrical pillars 401 with sidewalls 106 having cylindrical exteriors and cylindrical shaped pillar-microwells 104. The pillars can also be square-shaped pillars 402 or have another geometry with straight-sided exterior walls, and have a pillar-microwell 104 with straight sided walls that can form a square-shape cross-section. The square-shaped pillars 402 can have four planar exterior surfaces and square shaped pillar-microwells.

In another exemplary embodiment, the pillar plate 100 comprises a means for minimizing air bubble entrapment. The pillars 401, 402 can comprise a bore 406 that extends from the pillar-microwell base 305 at least partially through the pillar 402. In some exemplary embodiments, the diameter of the bore 406 is less than the diameter of the pillar 402. For example, in some exemplary embodiments, the diameter of the bore 406 can be, but is not limited to, 0.4 mm for a pillar with a diameter of 2 mm, or the diameter of the bore 406 can be, but is not limited to, 1 mm for a pillar with a diameter of 5 mm.

In another exemplary embodiment, the micropillar 102 comprises a bore 406 that extends from the pillar-microwell base 305 at least partially through the micropillar 102. In exemplary embodiments, the diameter of the bore 406 is less than the diameter of the micropillar. For example, in some exemplary embodiments, the diameter of the bore 406 can be, but is not limited to, 0.4 mm for a pillar with a diameter of 2 mm, or the diameter of the bore 406 can be, but is not limited to, 1 mm for a pillar with a diameter of 5 mm.

Further, in some exemplary embodiments, the pillar-microwell base can be plasma treated or coated with functional polymers to enhance robust cell spot attachment. Exemplary functional polymers include, but are not limited to, amphiphilic polymers, including poly(maleic anhydride-alt-1-octadecene) (PMA-OD), poly(maleic anhydride-alt-1-tetradecene) (PMA-TD), and polyethylene oxide-maleic anhydride copolymers, including ACM1510, ADM1510, AEM1510, AKM0530, and AKM1510, amphiphilic surfactants, including Brij C2 and C10, hydrogels, including alginate, collagen, PuraMatrix, fibrinogen, fibronectin, and Matrigel, other hydrophilic polymers, including polydopamine, poly(2-hydroxyethyl methacrylate) (pHEMA), and poly-L-lysine (PLL), and salts, including barium chloride ($BaCl_2$) and calcium chloride ($CaCl_2$)).

Figure 4:
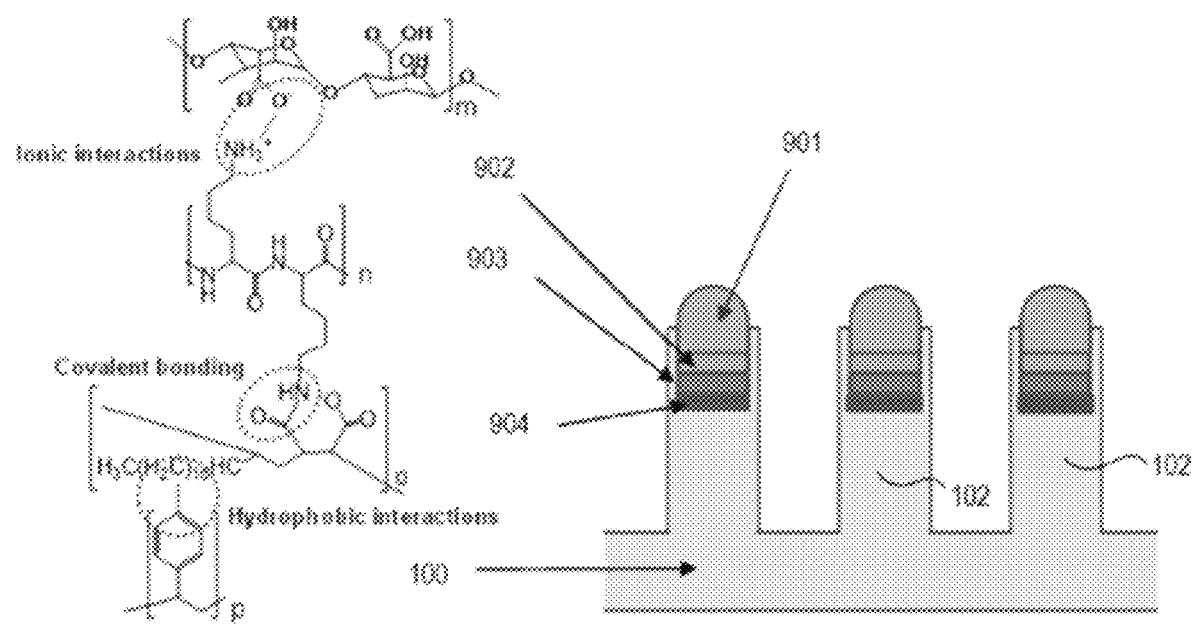
FIG. 4 shows an embodiment of surface coating on pillar-microwells of a pillar plate.
Figure 5A:
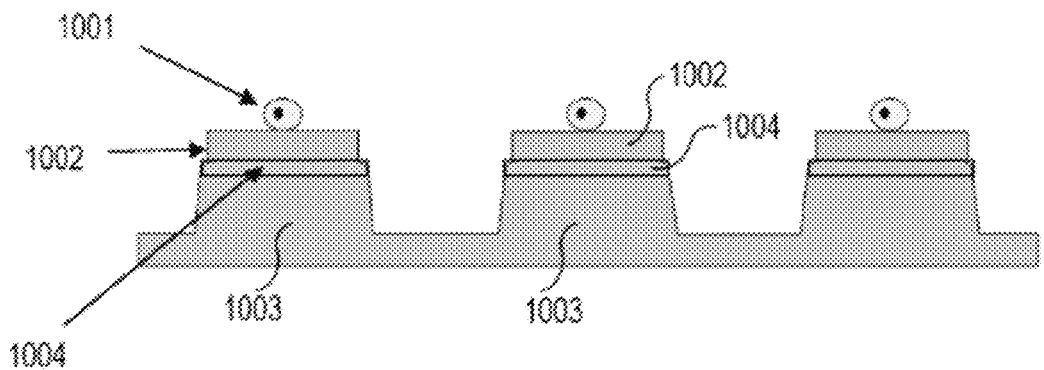
FIG. 5A shows an embodiment of a coating on a pillar plate.

Referring now to FIG. 4, a schematic representation of the surface chemistry of an embodiment of a functionalized pillar 102 is illustrated. The exemplary surface chemistry of the pillar plate 100 is for the purpose of avoiding air bubble entrapment on the pillar plate 100 while also avoiding 2D cell growth on the surface of the pillars 102. The pillar plate 100 can be polystyrene or can be made of other materials. An ultralow attachment (ULA) surface chemistry on the pillar plate 100 exists by printing nonadherent, hydrophilic polymers such as alginate and polyhydroxyethylmethacrylate (polyHEMA). In various embodiments, the surface coating is selected from poly(maleic anhydride-alt-1-octodecene) (PMA-OD), ploy-L-lysine (PLL)/$CaCl_2$) and alginate coatings. The coatings can create a nonadherent surface on the pillar plate 100 while maintaining robust interaction with Geltrex that encapsulates cell aggregates. For example, there can be multiple layers of surface coating such as PMA-OD 904, covered with PLL/$CaCl_2$) 903, and covered with alginate 902. The Geltrex encapsulated cell aggregates 901 can be deposited on top of the surface coating layers (as shown in FIG. 5A). If the pillar-microwells and/or perfusion plate wells are made of a hydrophobic polymer, it can need to be treated so that it is hydrophilic.

Accurately printing biological samples into a small, hydrophobic microwell on the pillar 102 is challenging due to high surface tension and associated problems such as air bubble entrapment. If the microwell is hydrophobic, air-bubble entrapment can be exacerbated. Air bubble entrapment can further be a problem at the incubating step of this method. To alleviate this problem, the surface property of the microwell on the pillar 102 can be changed from hydrophobic to hydrophilic. In some exemplary methods, this is carried out by treating the microwell on the pillar with plasma for 5-30 minutes. Exemplary gases for plasma treatment comprise atmospheric air, argon, oxygen, or nitrogen. In addition, in some exemplary embodiments, the surface of the microwell can be coated with a hydrophilic polymer, such as polydopamine, polyethylene glycol, collagen, or poly-L-lysine to enhance the hydrophilicity of the microwell surface.

Figure 5B:
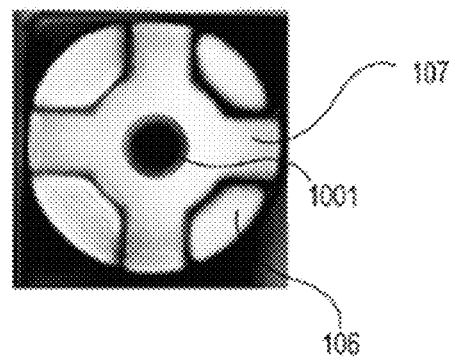
FIG. 5B shows an image of a cell spheroid loaded on a pillar plate.
Figure 5C:
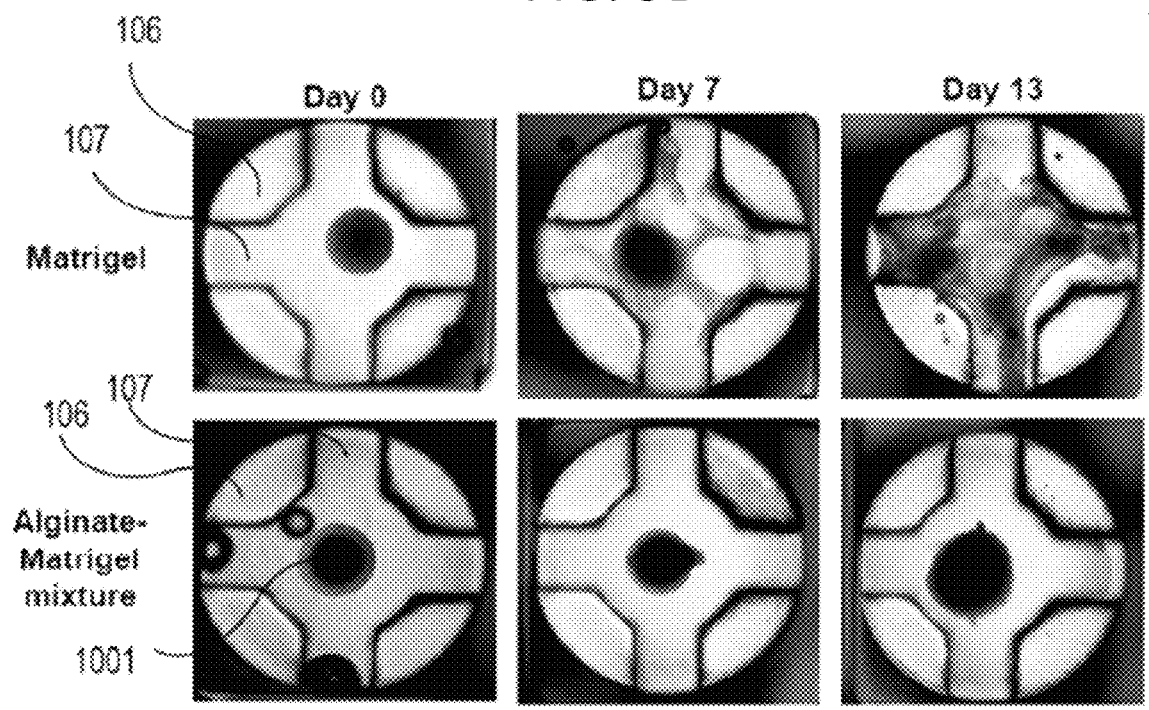
FIG. 5C shows images of cell spheroids grown on a pillar plate with different coatings.

Referring now to FIG. 5A, schematic of a pillar 1003 coated with an alginate-Matrigel mixture 1002 and a PMA-OD and PLL/CaCl$_2$) coating 1004 is illustrated. The mixture of alginate and Matrigel coated on the pillar plate prevents 2D growth of Hep3B cell spheroids and maintains the spherical morphology of the Hep3B cell spheroids 1001. Referring now to FIGS. 5B and 5C, images of Hep3B cell spheroid 1001 growth are shown. FIG. 5B is an image of Hep3B cell spheroids 1001 grown on alginate-Matrigel surface in the pillar microwell 106 having slits 107, without Matrigel encapsulation after 7 days. FIG. 5C shows, in a close up view of pillars including sidewall 106 and slits 107, a plurality of images of Hep3B cell spheroid 1001 growth on Matrigel-coated and the mixture of alginate and Matrigel-coated pillar plates, after zero days, 7 days, and 13 days. The Hep3B spheroids on the alginate-Matrigel layer, with no Matrigel encapsulation, maintained spherical morphology for a longer period of time without 2D growth as compared to the Matrigel-only counterparts.

Figure 6A:
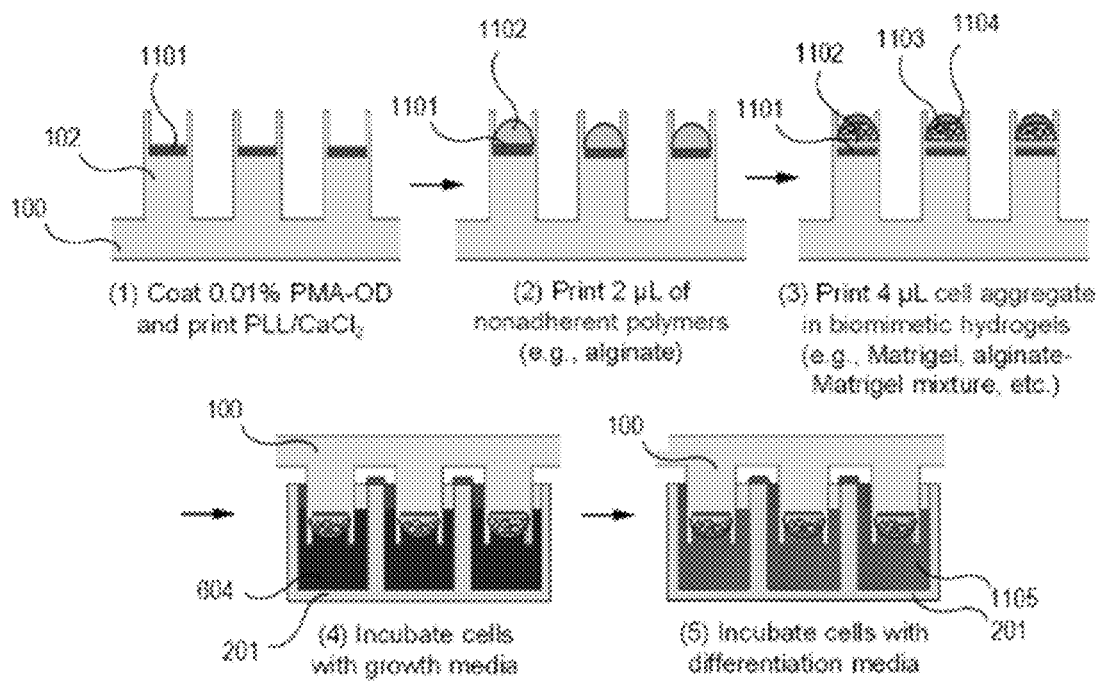
FIG. 6A shows images conveying the procedure for surface coating, cell printing, and cell culture on a pillar plate, according to an exemplary embodiment.

After surface coating of the pillar-microwells, cells can be loaded and/or cultured on the pillar plates. The cell loading strategies on the pillar plates according to the exemplary embodiments described herein can be used to conduct high throughput testing on the pillar plates. The experimental procedures and methods using the pillar plate described herein can vary based on available equipment and desired cell growth techniques. Cell suspensions or cell aggregates can be printed on pillars according to known conventional techniques, and can be printed on conventional pillars or other pillar-microwell structures, including but not limited to the pillar structures described herein. This can include use of known hydrogels and ULA plates. Incubating and/or growing cells on the pillars and/or in the pillar-microwells as described herein can be achieved by engaging the pillar plate with a well plate such as the exemplary embodiments described herein, and applying growth media according to the methods described herein (as shown in FIG. 6A). However, the cell incubation and/or growth is not limited to the use of the conventional microtiter well plates. A well plate, including but not limited to a ULA plate, and/or incubation and/or growth with perfusion, can also be used.

Two exemplary methods of loading human cells onto pillar plates are described, including direct cell printing onto the pillar-microwells on the pillar plates (FIG. 6A) and transferring cell aggregates from a ULA well plate to the pillar plates (FIGS. 7A-7J). According to the first exemplary method (FIG. 6A), direct cell printing in biomimetic hydrogels allows users to create multiple layers of different cell types for mimicking human tissues in vivo.

With reference to FIG. 6A, step (1), the microwell in at least one and as many as all of the pillars 102 of the pillar plate 100 is functionalized by surface coating 1101. The surface coating can be 0.01% PMA-OD and/or PLL/CaCl$_2$), which can be printed on the surface. The pillar-microwell structure on the pillar plate 100 can be any aforementioned structure.

In step (2) of FIG. 6A, a volume of nonadherent polymer 1102 is printed on the surface coating 1101. The volume can be 1-8 μL of a nonadherent polymer such as alginate and polyhydroxyethylmethacrylate (polyHEMA). In step (3) of FIG. 6A, a volume of cell aggregate 1103 in biomimetic hydrogel 1104 can be printed on the nonadherent polymers 1102. For example, a volume of 1-7 μL of cell aggregates can be used. Exemplary biomimetic hydrogels include alginate, collagen, PuraMatrix, fibrinogen, fibronectin, Matrigel, and mixtures of these hydrogels. The application of the surface coating, nonadherent polymers, and cell aggregates is not limited to the examples provided herein, but can include any known technique for applying a surface coating, nonadherent polymers, and cell aggregates.

In step (4) of FIG. 6A, the pillar plate 100 is inverted and placed on the perfusion well plate 201 or conventional microtiter well plates so that the pillars 102 are each inserted into perfusion wells or static wells, and the cells are incubated with growth media 604. In step (5) of FIG. 6A, the cells are incubated with differentiation media 1105.

Figure 6B:
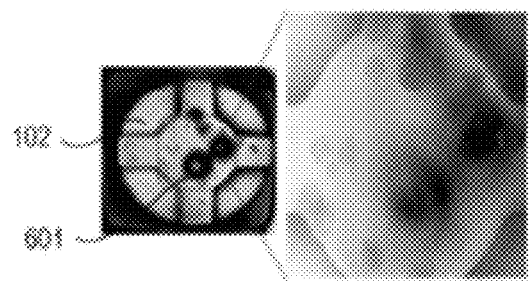
FIG. 6B shows images of Hep3B cell aggregates loaded on a pillar-microwell for organotypic tumor tissue culture.
Figure 6C:
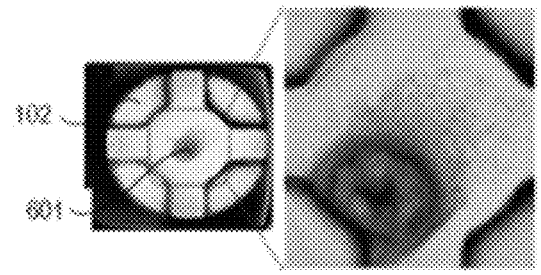
FIG. 6C shows images of hindgut spheroids loaded on a pillar-microwell for human intestine organoid culture.

FIGS. 6B and 6C illustrate Hep3B cell aggregates and intestinal organoids cultured on the pillar plates by direct cell printing. Referring to FIG. 6B, 4× bright-field images of Hep3B human hepatoma cell aggregates 601 in a pillar-microwell 102 are shown. Hep3B aggregates in 120-180 μm diameter were printed successfully in 3-fold diluted Geltrex on the 384-pillar plate. The aggregates were generated by seeding Hep3B cells at 6.7×10$^5$ cells/mL in MPc350 6-well inserts and incubating for two days. Referring to FIG. 6C, 4× bright-field images of hindgut cell aggregates 601 which are premature human intestinal organoids (HIOs) are shown in a pillar-microwell 102. Intestinal organoids in 400-700 μm diameter were printed successfully in 2-fold diluted Geltrex on the 384-pillar plate.

According to the second exemplary method (FIGS. 7A-J), transferring cell aggregates from a ULA well plate can be performed by sandwiching the pillar plate 100 with thermosensitive hydrogels such as Matrigel and collagen onto the ULA well plate 201 with cell aggregates, which allows users to rapidly transfer spheroids formed from ULA well plates 201 without potentially cumbersome cell printing. Further, as described in U.S. patent application Ser. No. 15/816,485, a blank pillar plate can be engaged with a well plate containing cell suspension in biomimetic hydrogels for cell loading. The methods described herein are exemplary and are not to be considered limiting as to the use of the pillar plate and the ULA well plate assembly described herein.

Referring to FIGS. 7A-7I, experimental procedures for embedding cell aggregates on the pillar plate by having the cells encapsulated in a hydrogel, are illustrated. The exemplary method provided herein can accomplish Matrigel embedding without pipetting, which is known to be time consuming and cumbersome. The exemplary method can include the steps of first creating cell aggregates in a well plate, which can be a ULA well plate, a perfusion plate, or a microtiter plate. The cell aggregates can be created in the wells by incubating a cell suspension with a growth media in the wells for about 2 to 3 days. The cell aggregation occurs due to gravity and cell adhesion. Next, thermosensitive hydrogels, such as Matrigel (without gelation), can be loaded into pillar-microwells on a pillar plate for cell aggregate encapsulation. Immediately after the hydrogel loading, the pillar plate can be sandwiched with the well plate, and the sandwiched plates can be inverted. While inverted, the cell aggregates in the growth media in the well plate settle onto the pillar-microwells of the pillar plate by gravity, and then become encapsulated in the thermosensitive hydrogel by gelation, due to an elevated temperature.

In an exemplary method, the cells can be loaded onto the pillars of a pillar plate. First, cell aggregates can be created in a ULA well plate by incubating cell suspension in growth media for 2-3 days. The incubation can take place in an environment having a temperature of, for example, 37° C. The hydrogel, which includes but is not limited to cold Matrigel, can be loaded in the pillar-microwells on a pillar plate. Immediately after hydrogel loading, the pillar plate can be sandwiched with the ULA well plate. The sandwiched pillar plate and ULA well plate can then be inverted.

While inverted, the cell aggregates in growth media in the ULA well plate can settle onto the pillar-microwells of the pillar plate and then become encapsulated in the hydrogel by gelation.

The cell aggregates can be transferred in a similar manner from a perfusion plate to the pillar plate, by sandwiching the plates and inverting them. The cell aggregates will remain protected by the encapsulation. The cell aggregates can be transferred from any one of a ULA plate, a microtiter well plate, or a perfusion plate to the pillar plate according to any of the exemplary embodiments described herein. The new plate can have growth media in its wells including but not limited to the growth media described herein. Further, once the cell aggregates have been transferred to the pillar plates and/or any further plates from the pillar plates, testing can be performed on the cell aggregates. The encapsulation protects the cell aggregates and eliminates the need for pipetting the cell aggregates, to vary the growth media applied to the cells. Testing can include any traditional testing, including but not limited to that described herein.

Figure 7A:
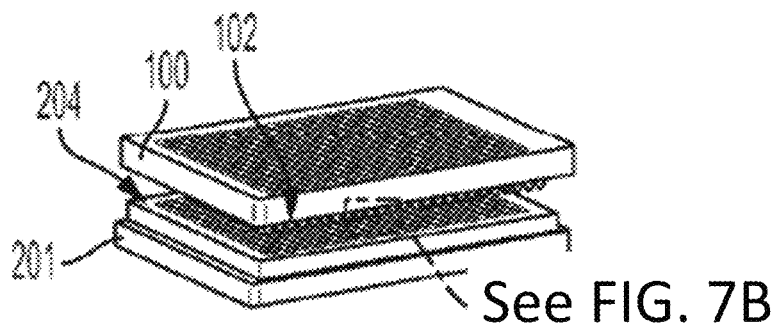
FIG. 7A shows sandwiching a pillar plate with thermosensitive hydrogel on pillar-microwells onto an ultralow attachment (ULA) well plate with cell aggregates.
Figure 7B:
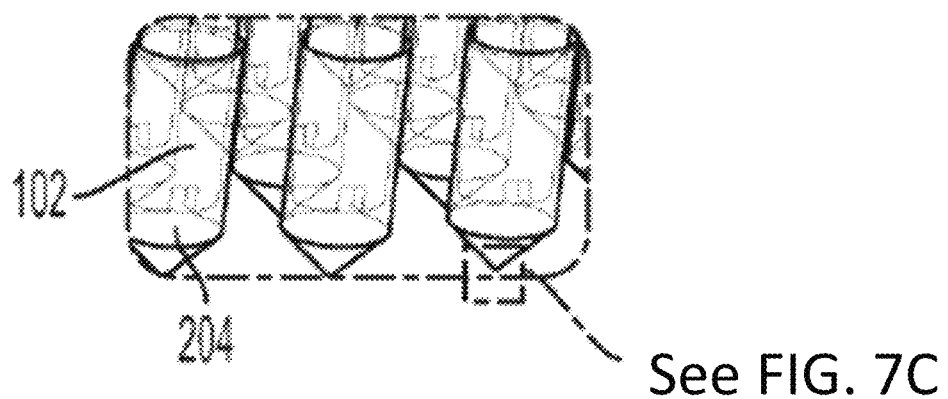
FIG. 7B shows a close-up view of pillar-microwells engaged with ULA wells of FIG. 7A.
Figure 7C:
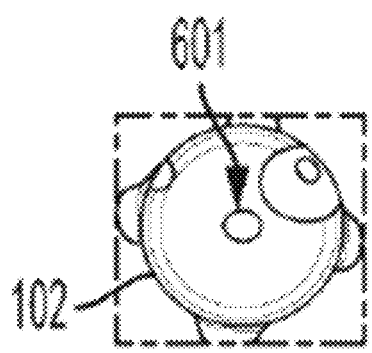
FIG. 7C shows a cell aggregate in the center of a ULA well from FIG. 7B.

Referring now to FIG. 7A, in one example, after forming cell aggregates in a ULA 384-well plate 201 for 2 days, the 384-pillar plate 100 with Matrigel in pillar-microwells was sandwiched onto the ULA 384-well plate 201 with neural stem cell aggregates, and then the sandwiched plates were inverted. FIG. 7A shows the ULA well plate and the pillar plate in an exploded view to improve visibility of the plates for explanatory purposes, but in use, they are positioned together so that the pillars are inserted into the ULA wells. The diameter of cell aggregates was approximately 350 μm. FIG. 7B illustrates a close-up view of the pillar-microwells 102 positioned into the ULA wells 204. FIG. 7C illustrates a close-up view of one pillar-microwell 102 positioned in a ULA well having a cell aggregate 601. The cell aggregate 601 can be a neural stem cell aggregate, for example.

Figure 7D:
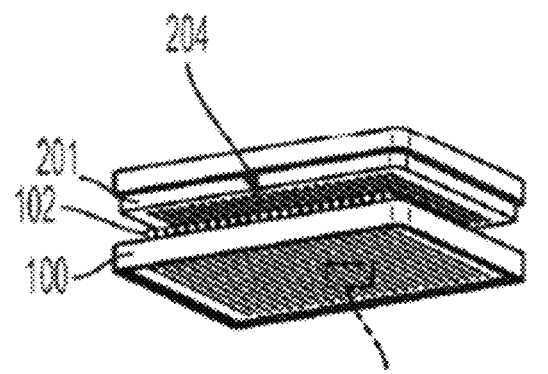
FIG. 7D shows transferring cell aggregates from the ULA well plate to the pillar plate by inverting the sandwiched plates.
Figure 7E:
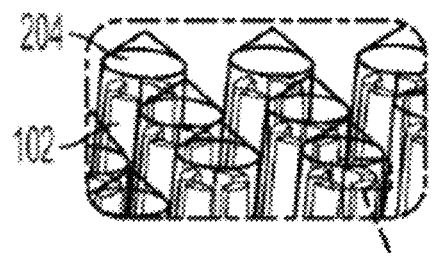
FIG. 7E shows a close-up view of inverted pillar-microwells engaged with ULA wells of FIG. 7D.
Figure 7F:
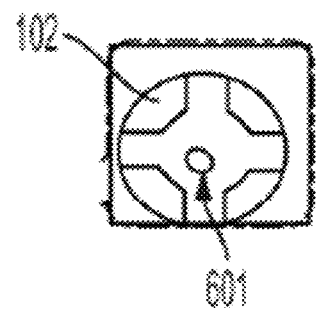
FIG. 7F shows a cell aggregate loaded on a pillar-microwell from FIG. 7E.
Figure 7G:
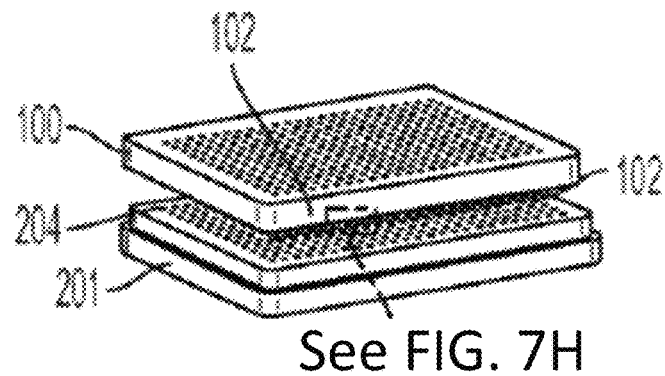
FIG. 7G shows the pillar plate with encapsulated cell aggregates in thermosensitive hydrogel sandwiched onto a new well plate with cell culture media.

Referring now to FIGS. 7D-7F, an example of inverted plates for transferring cell aggregates is illustrated. FIG. 7D illustrates the pillar plate 201 and the ULA well plate 100 in an exploded view to improve visibility of the plates for explanatory purposes, and FIG. 7E illustrates a close-up view of the pillar-microwells 102 inserted into the ULA wells 204. FIG. 7F illustrates a close-up view of one pillar-microwell 102 having a cell aggregate 601. Referring back to FIG. 7D, the inverted plates were incubated at room temperature for 5 minutes for cell aggregates precipitation and then at 37° C. for 20 minutes for Matrigel gelation. Over 95% of cell aggregates were successfully encapsulated in Matrigel on the 384-pillar plate without pipetting. Referring now to FIG. 7G, the sandwiched plates were inverted again to place the 384-pillar plate on top for long-term organoid culture. Growth media were replaced every 1-2 days.

Figure 7H:
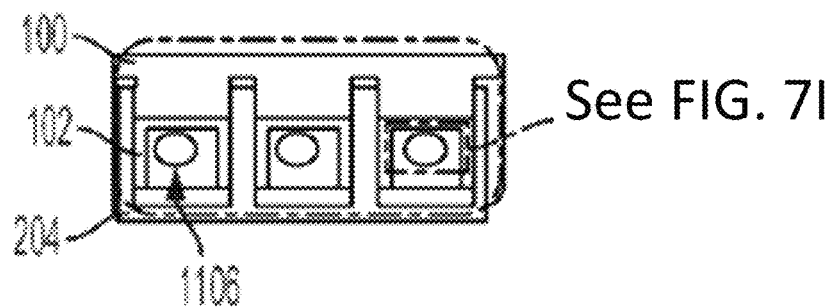
FIG. 7H shows a close-up view of pillar-microwells with cell aggregates sandwiched with wells of FIG. 7G.
Figure 7I:
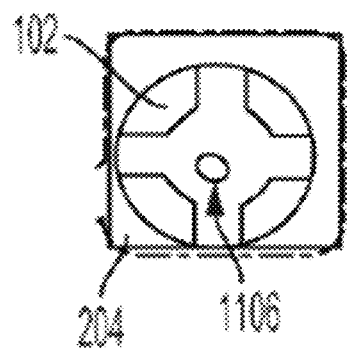
FIG. 7I shows a cell aggregate encapsulated in thermosensitive hydrogel on a pillar-microwell from FIG. 7H.

Referring now to FIGS. 7G-7I, after discarding the ULA plate, an example of a pillar plate 100 positioned on top of a microtiter well plate 201, so that the contents of a pillar-microwell 102 are positioned between the pillar plate 100 and the microtiter well plate 201, is illustrated. The pillars 102 are each inserted into a microtiter well 204. The plates are in an exploded view to improve visibility of the plates for explanatory purposes. FIG. 7H illustrates a close-up view of the pillars 102 in the microtiter wells, and the cell aggregates 1106 that are growing inside the pillar-microwell. FIG. 7I illustrates a close-up view of one pillar-microwell 102 inserted into a microtiter well 204, having a cell aggregate 1106 contained between the pillar and the microtiter well.

Figure 7J:
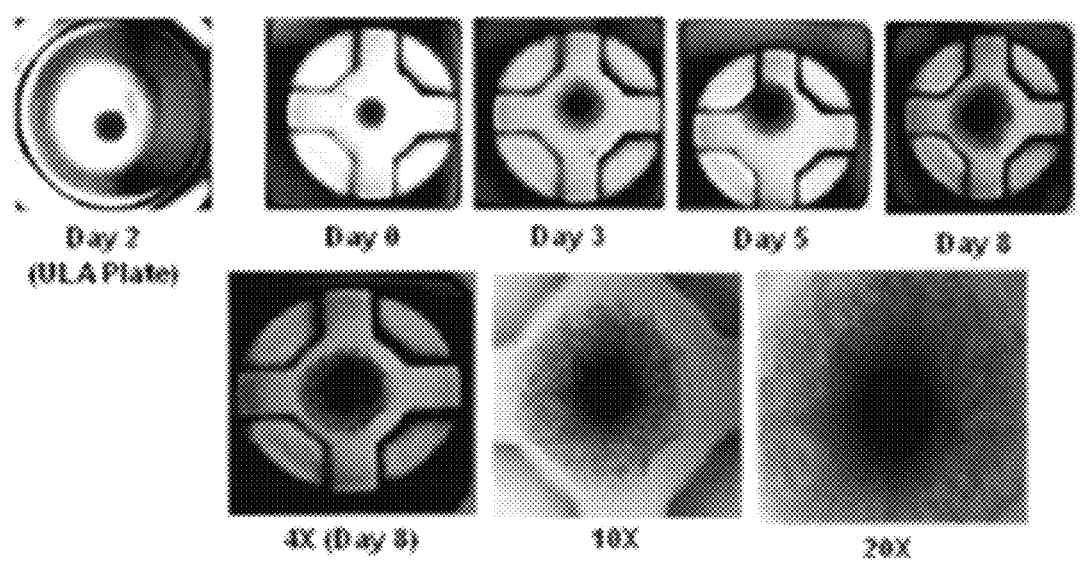
FIG. 7J shows images of ReNcell VM aggregates transferred from a ULA well plate to a pillar plate and cultured over time.

Referring now to FIG. 7J, the growth of neural stem cell aggregates in Matrigel on the 384-pillar plate over time is shown. In the top row of images of FIG. 7J, moving from left to right, respectively, the stem cell aggregates at day 2 in a ULA well plate for comparison is shown, then at day 0, day 3, day 5, and day 8 on the pillar plate, are shown. In the bottom row of images in FIG. 7J, magnifications of the neural stem cell aggregates on the pillar plate at day 8 are shown, from left to right, at 4× magnification, 10× magnification, and 20× magnification. The neural stem cell aggregates have an appearance very similar to neurospheres in shape. Two spheres can be loaded in close proximity.

Perfusion Plate

Figure 8A:
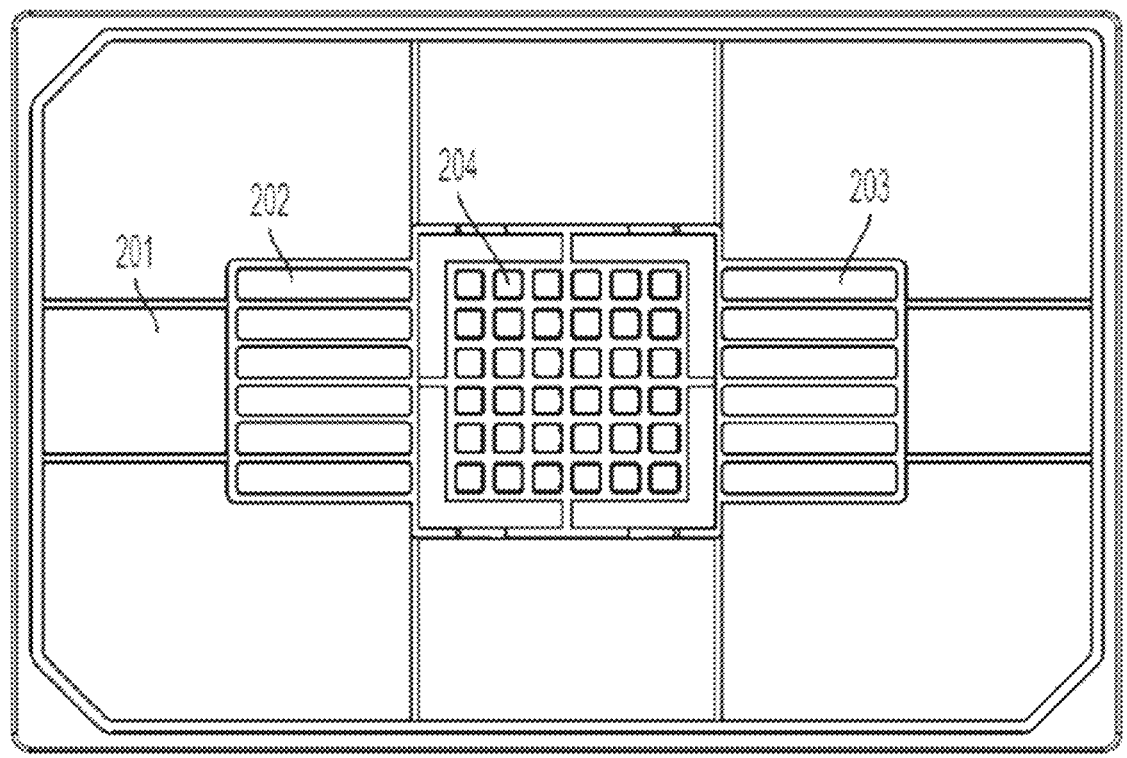
FIG. 8A shows a top-down view of a perfusion plate according to an exemplary embodiment.
Figure 8B:
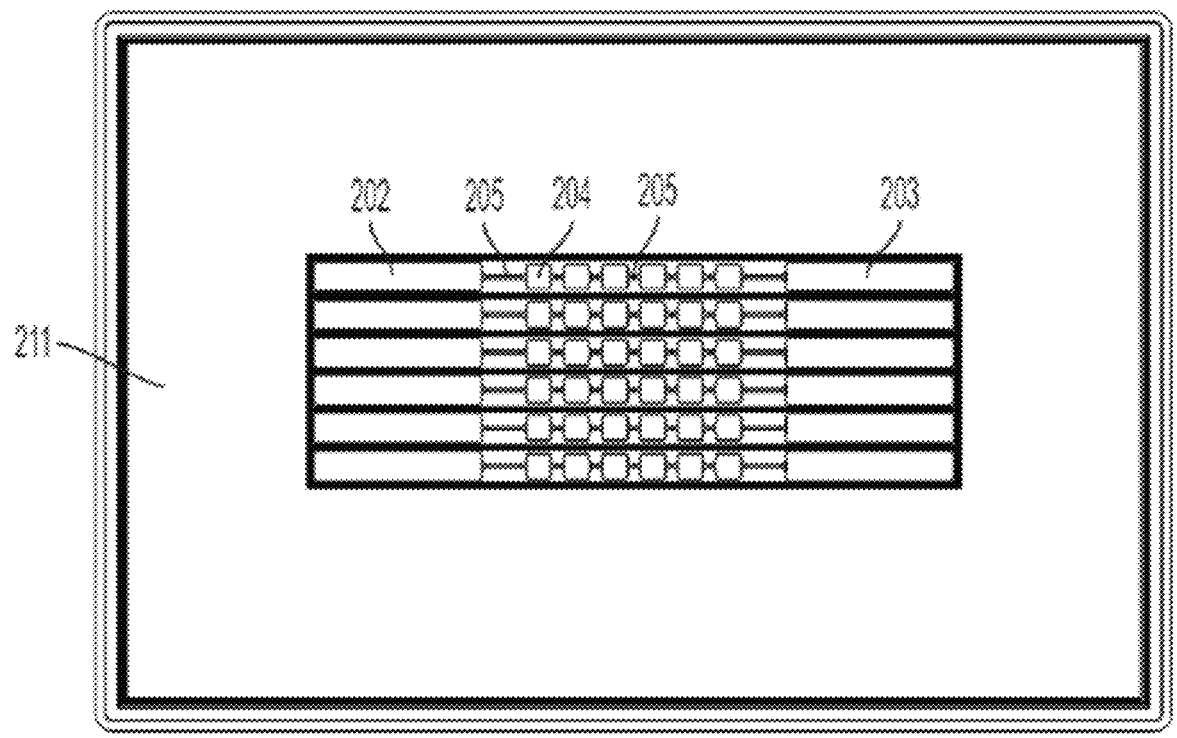
FIG. 8B shows a bottom-up view of the embodiment of the perfusion plate of FIG. 8A.
Figure 8C:
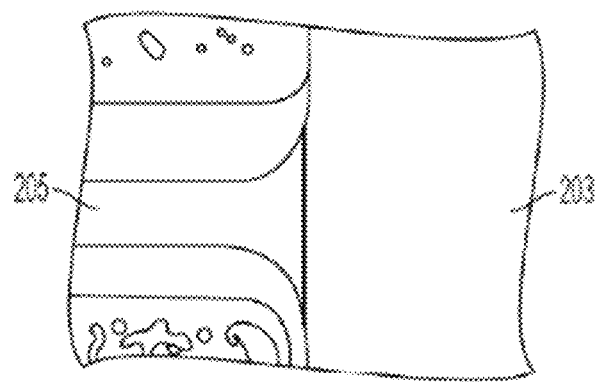
FIG. 8C shows a close-up view of the embodiment of the perfusion plate shown in FIG. 8B.

Referring now to FIGS. 8A-8C, a perfusion plate 201 having reservoirs 202, 203, perfusion wells 204, is illustrated. In FIG. 8A, a top-down view of the perfusion plate 201 is shown. The reservoirs 202, 203 and perfusion wells 204 are arranged on the perfusion plate 201. There are two sets of reservoirs, the inflow reservoirs 202 and the outflow reservoirs 203. Fluid, such as cell growth media, can flow from the inflow reservoirs 202 to the outflow reservoirs 203 by passing through microchannels 205 (see FIG. 8B). The perfusion wells 204 can be arranged in an array of 6 perfusion wells by 6 perfusion wells, in the embodiment of FIGS. 8A-8C, but any number array of perfusion wells 204 can be used.

The perfusion well array can match the pillar array (see FIGS. 1A-FIG. 4), as described in various embodiments herein, in number, arrangement of the array, and/or geometry. The interior geometry of the perfusion wells 204 can match the exterior geometry of the pillar-microwells 104 of the pillar plate 100 (see FIGS. 2-3). When the pillar-microwells 104 of the pillar plate 100 are inserted into the perfusion wells 204 of the perfusion plate 201, the slits 107 can line up with the microchannels 205 so that the microchannels 205 are fluidly connected to the pillar-microwells 104. The perfusion plate 201 can be a 36-perfusion well plate, a 256-perfusion well plate, or a 384-perfusion well plate, or have 36, 256, or 384 perfusion wells. The perfusion plate 201 can have at least as many perfusion wells 204 as a pillar plate 100 has pillar-microwells 104, so that the pillar-microwells 104 on a pillar plate 100 can be used with the perfusion plate 201 and the contents on the pillar-microwells 104 are positioned within perfusion wells 204. The perfusion plate 201 can also have a greater number of perfusion wells 204 than the number of pillar-microwells 104 on a corresponding pillar plate 100.

In FIG. 8B, a bottom-up view of the perfusion plate 201 is shown. The perfusion plate 201 is visible through a transparent plate 211, which can be attached to the bottom of the perfusion plate by using an adhesive or by ultrasonic welding. The transparent plate 211 can be a thin glass slide or a thin plastic film, or any other transparent sheet-like element. Cells that are incubated, grown, and/or tested with the exemplary perfusion plates described in any of the embodiments herein can be imaged through the transparent plate 211 on the bottom of the perfusion plate 201. At least one microchannel 205 fluidly connects the perfusion wells 204 to the inflow reservoirs 202 and the outflow reservoirs 203. FIG. 8C illustrates a close-up view of a microchannel 205 fluidly connected to the inflow reservoirs 202 and the outflow reservoirs 203.

Figure 9:
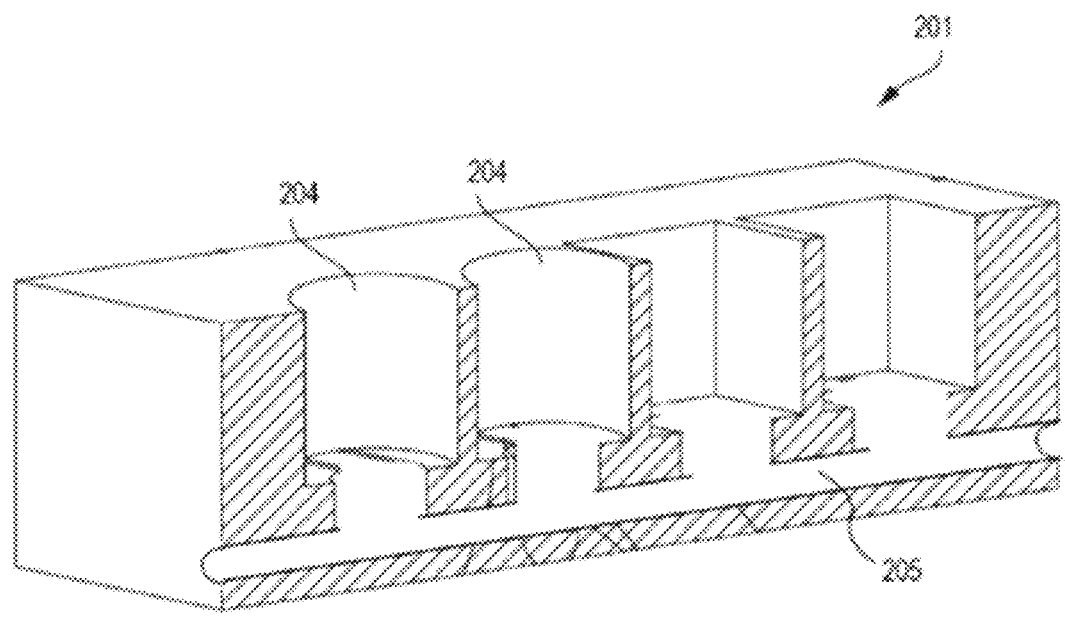
FIG. 9 shows a sectional view of various embodiments of perfusion wells in the perfusion plate.

Referring now to FIG. 9, a cross section of a row of exemplary embodiments of perfusion wells 204 in a perfusion plate 201 is illustrated. The perfusion wells 204 correspond to the pillar-microwells 104 illustrated in FIG. 2. That is, the perfusion wells 204 can have a cylindrical shape or they can have a shape with planar walls. The perfusion wells 204 can each be fluidly connected to a microchannel 205 that is fluidly connected at a first end to an inflow reservoir 202 (shown in FIG. 8B) and fluidly connected at a second end to an outflow reservoir 202 (shown in FIG. 8B). For example, in some exemplary embodiments, the dimension of the microchannel 205 can be 0.2 mm (width) by 0.2 mm (height) by 1.2 mm (length). In various embodiments, the dimension of the perfusion well 204 can be 3.2 mm (width) by 3.2 mm (length) by 13 mm (height). In various embodiments, the dimension of the perfusion well 204 can be 3.2 mm (width) by 20 mm (length) by 16 mm (height).

Table 1 below provides information on an exemplary embodiment outside of a range of perfusion wells 204 and reservoirs (for example the inflow reservoirs 202 and the outflow reservoirs 203) and their maximum allowable volumes. The reservoirs can each have a volume ranging from 0 μL to 1200 μL. In various embodiments, the reservoirs can each have a volume ranging from 300 μL to 700 μL. In various embodiments, the reservoirs can each have a volume ranging from 900 μL to 1100 μL. The perfusion wells can each have a volume from 0 μL to 110 μL. In various embodiments, the perfusion wells can each have a volume from 30 μL to 60 μL. The perfusion wells can each have a volume from 60 μL to 90 μL. In various embodiments, the inflow reservoir can have an operational volume from 600 μL to 1000 μL. In various embodiments, the inflow reservoir can have an operational volume from 800 μL to 1200 μL. In various embodiments, the inflow reservoir can have an operational volume from 900 μL to 1100 μL. The outflow reservoir can have an operational volume of 0 μL at the beginning of using the perfusion plate, because the growth media or other fluid has not yet moved from the inflow reservoir to the outflow reservoir.

TABLE 1

Liquid volume allowed in the perfusion well plate

| Channel composition | Number | Max. volume (μL) | Total volume (μL) | Operational volume for cell culture (μL) |
| --- | --- | --- | --- | --- |
| Reservoir | 2 | 1169 | 2338 | 1000 (inflow) 0 (outflow) |
| Perfusion well | 6 | 108 | 648 | 50-60 |

Figure 10:
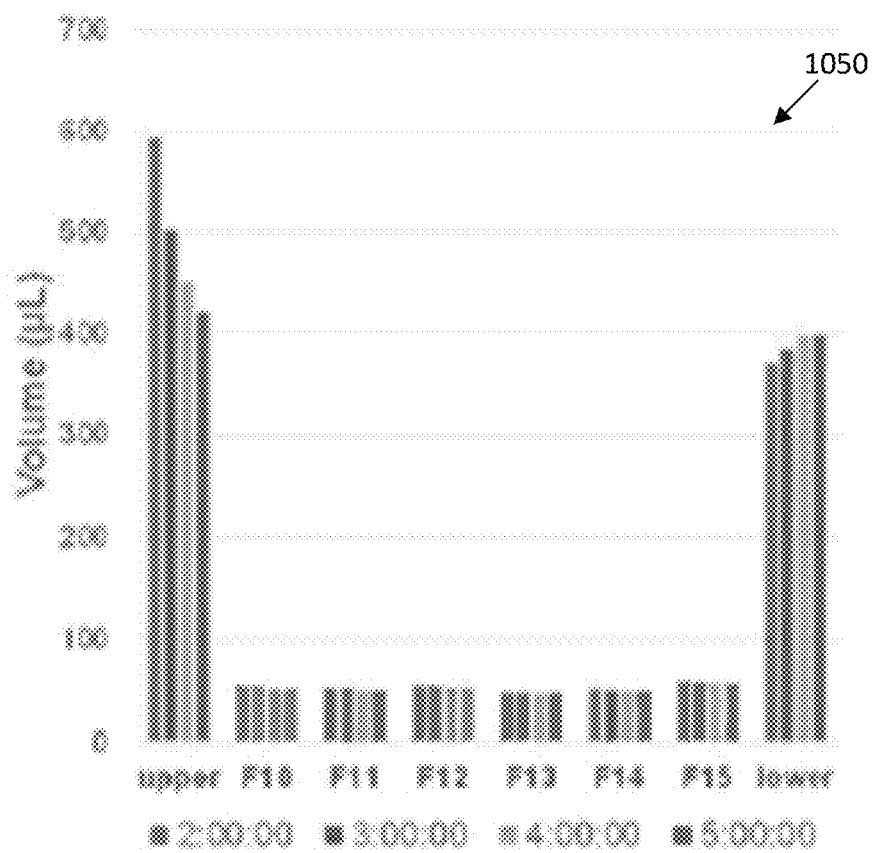
FIG. 10 shows changes in flow rates over time in the reservoirs and perfusion wells of a perfusion plate according to an exemplary embodiment.

Referring now to FIG. 10, a chart 1050 indicating flow rates in a 36 well perfusion plate is illustrated. In this example, 1200 μL of 10 μM rhodamine B-dextran was provided in the inflow reservoirs and measured at time intervals of 2, 3, 4, and 5 hours. The X-axis indicates the reservoir and the row of perfusion wells, and the Y-axis indicates the volume in μL. For each reservoir and perfusion well, moving from left to right, the first bar indicates the volume at hour 2, the second bar indicates the volume at hour 3, the third bar indicates the volume at hour 4, and the fourth bar indicates the volume at hour 5.

Figure 11:
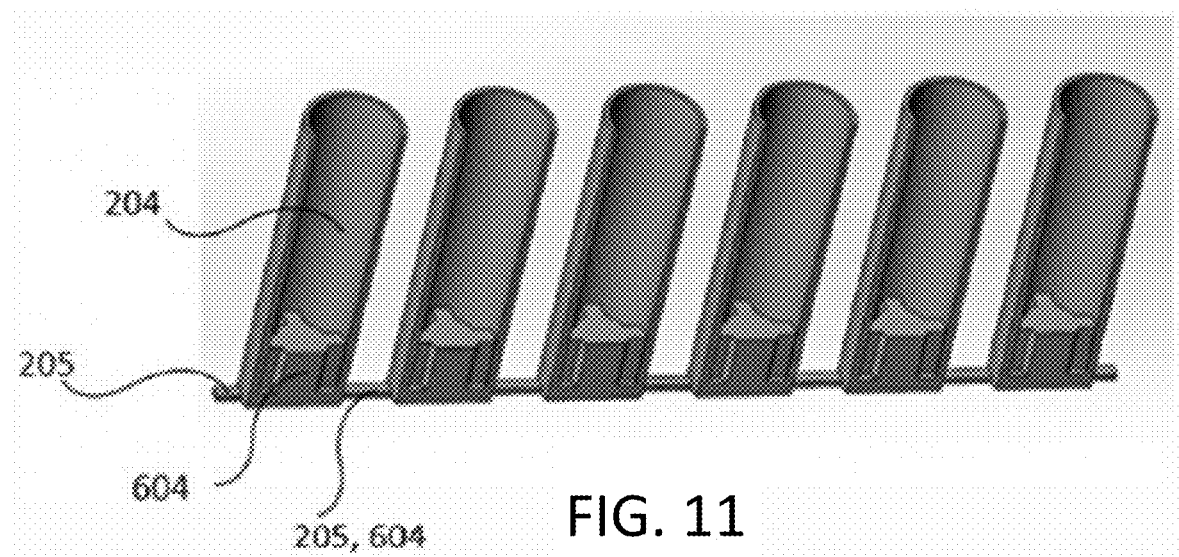
FIG. 11 shows fluid in microchannels and perfusion wells of a perfusion plate at a certain moment in time for COMSOL Multiphysics simulation.

Referring now to FIG. 11, a row of perfusion wells 204 fluidly connected to each other by a perfusion channel 205 (also referred to as microchannel 205) is illustrated. The perfusion wells 204 can each have a volume of growth media 604 in them, and the microchannel 205 can be filled with growth media 604 as well. The fluid is not limited to growth media 604 but can be any media that is used in the perfusion plate. The velocity at which the growth media 604 moves varies. In a simulation performed using one row of 6 perfusion wells connected by microchannels 205 having a dimension of 0.4 mm by 0.2 mm, to simulate an array of 256 perfusion wells, the greatest velocity profiles were found in and around the microchannels 205. The velocity in and around the microchannels 205 ranged from about $1.2\times10^{-3}$ mm/s to $2.0\times10^{-3}$ mm/s and the velocity in and around the perfusion wells 204 ranged from 0.0 mm/s to $0.8\times10^{-3}$ mm per second. The velocities are faster the farther away from a channel or well wall the growth media is, and slower the closer the growth media is to the wall. In some exemplary embodiments, the dimension of the microchannel 205 can be, but is not limited to, 0.2 mm (width) by 0.2 mm (height) by 1.2 mm (length).

Pillar and Perfusion Plate Assembly

Figure 12A:
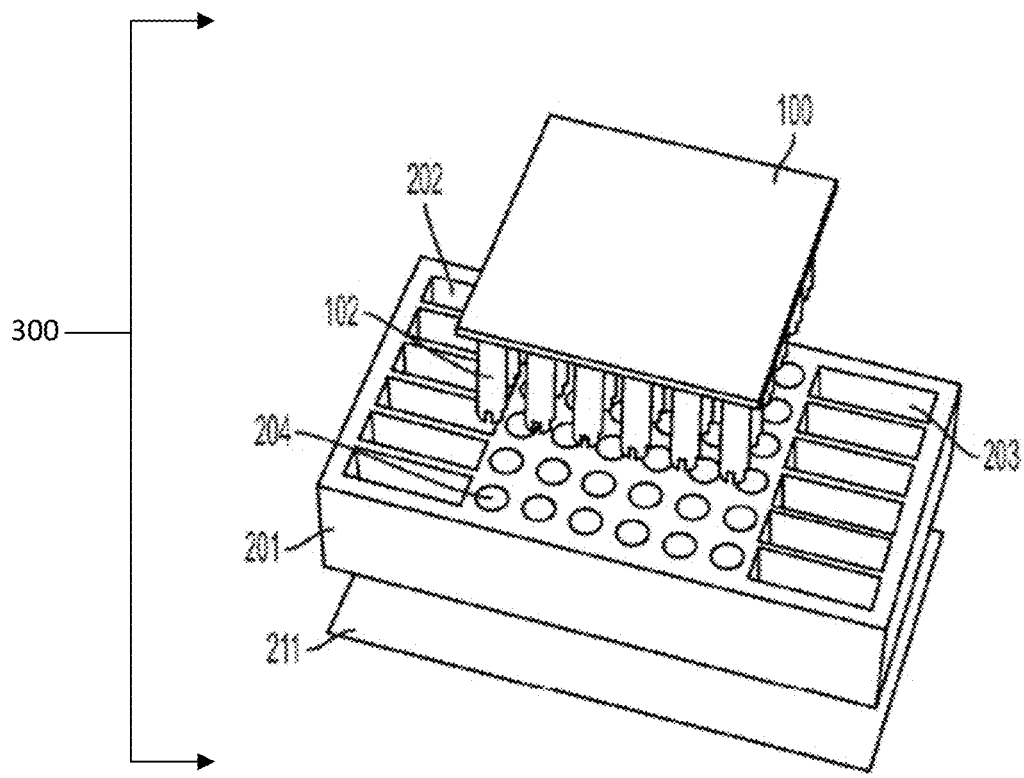
FIG. 12A shows an expanded perspective view of an assembly including a pillar plate, a perfusion plate, and a transparent plate.
Figure 12B:
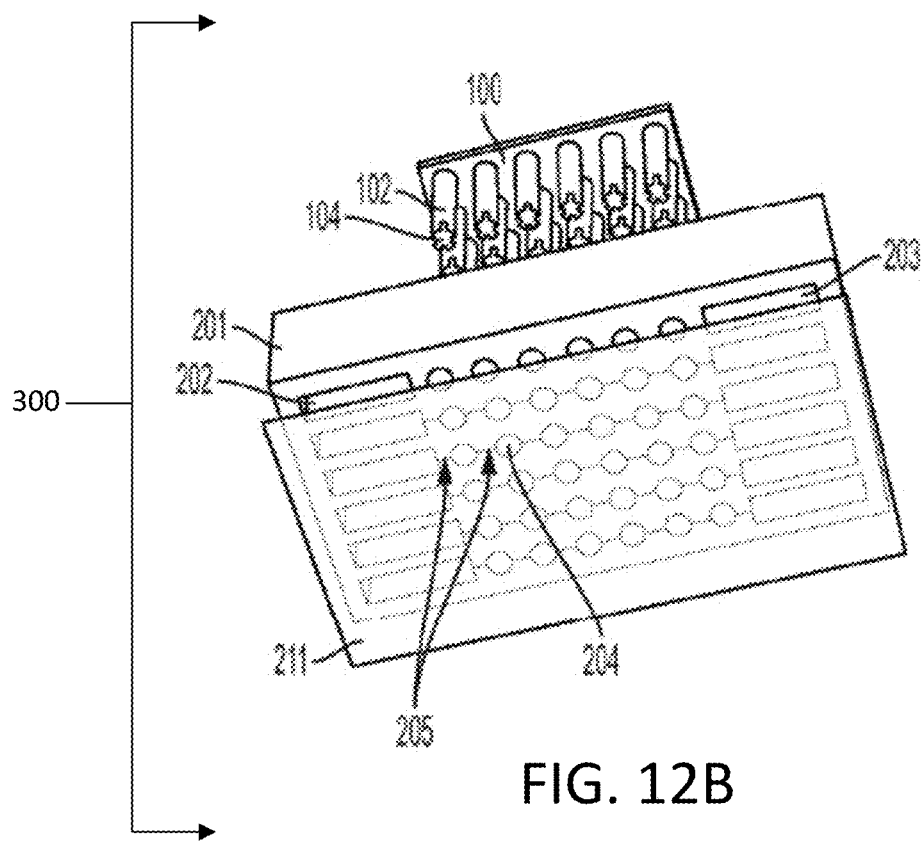
FIG. 12B shows an expanded perspective view of the assembly of FIG. 12A.
Figure 12C:
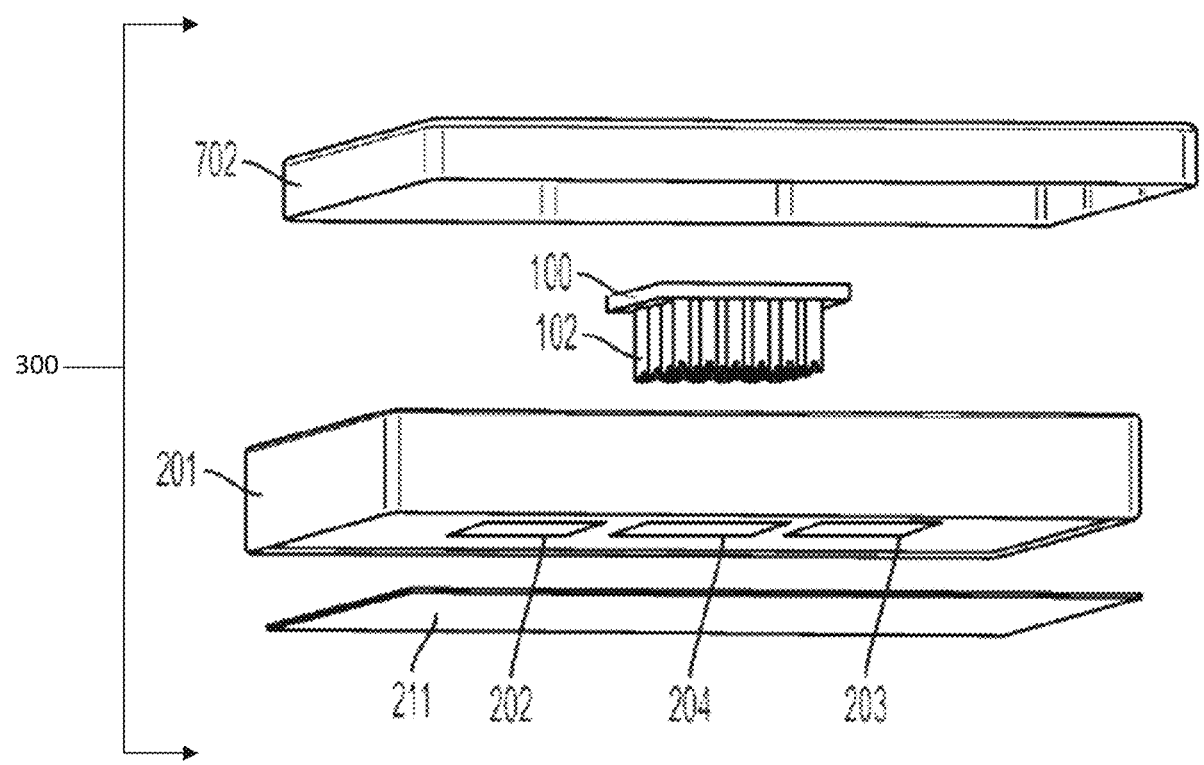
FIG. 12C shows an expanded side view of the assembly of FIG. 12A further including a lid.

Referring to FIGS. 12A-12C, an assembly 300 can comprise a pillar plate 100, a perfusion plate 201, and a transparent plate 211, each according to various embodiments described above. Referring to FIGS. 12A-12C, an expanded view of the assembly 300 is illustrated. The pillar plate 100 can have an array of 36 pillars, and the pillars 102 can be inserted into the perfusion wells 204. FIG. 12A shows a top perspective view in which inflow reservoirs 202, outflow reservoirs 203, pillars 102, and perfusion wells 204 are illustrated. FIG. 12B shows a bottom perspective view, showing the same components as FIG. 12A, and also illustrating microchannels 205 and pillar-microwells 104. FIG. 12C shows an expanded side view of the assembly 300, with a lid 702 that can be placed on top of the perfusion plate 201 with transparent plate 211 attached to its bottom, once the pillar plate 100 with pillars 102 are positioned in the perfusion wells 204. For cell culture and imaging, a thin glass slide (or a thin plastic film) can be attached at the bottom of the 36-well perfusion plate with microchannels for connecting 36 perfusion wells. Growth media can be added to the inflow reservoirs 202 and flow unidirectionally without using a syringe pump or a rocker to the outflow reservoirs 203. The 36-pillar plate with organoids can be fit between the perfusion plate 201 and pillar plate 100 according to the exemplary embodiments described herein to investigate organoid interactions.

Another exemplary embodiment having 256 perfusion wells in a perfusion plate and 256 pillars on a pillar plate can be used the same way as the 36-array embodiment. Various organoids can be printed rapidly onto a 256-pillar plate using the microarray spotter that is combined with the 256-perfusion well plate containing individual growth media in each reservoir for organoid cultures. After long-term cell culture, the pillar plate containing organoids can be separated, rotated at 90-degree angle, and engaged with a new perfusion plate containing compounds in universal growth media for mechanistic toxicity assays. As explained above, the number of pillars and perfusion wells do not have to be the same, as long as there are at least as many perfusion wells as pillars when the pillar plate is engaged with the perfusion plate.

Figure 13:
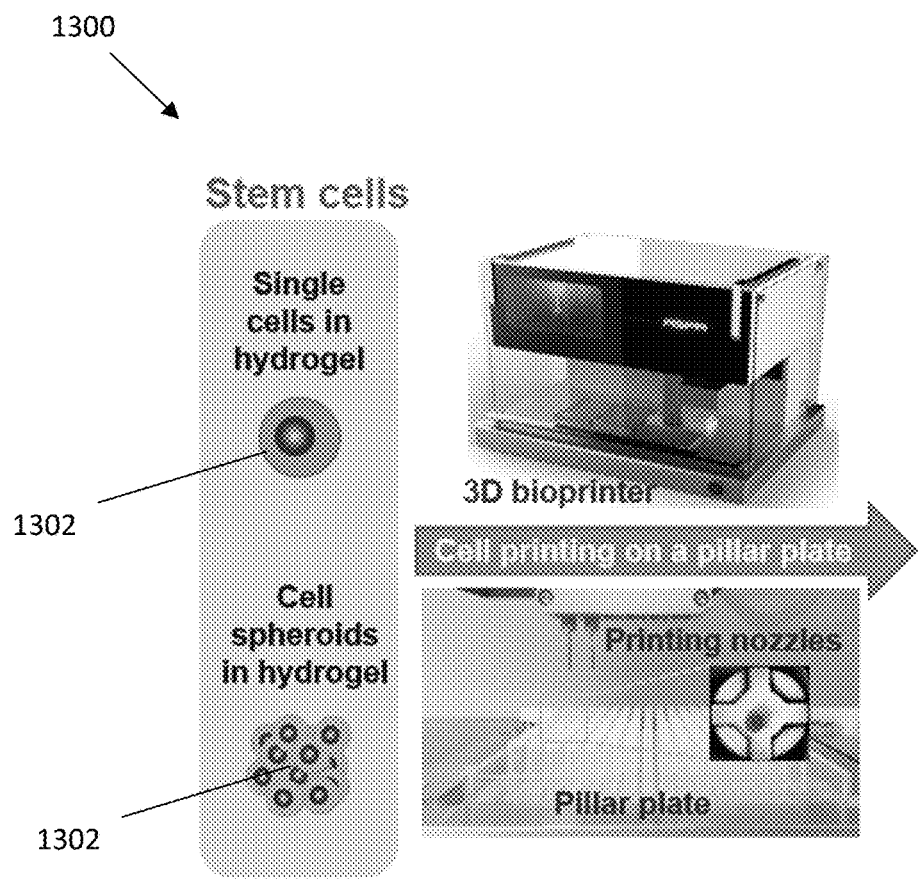
FIG. 13 shows miniature 3D bioprinting technology and associated pillar and perfusion plate platforms for human organoid culture and analysis.
Figure 13:
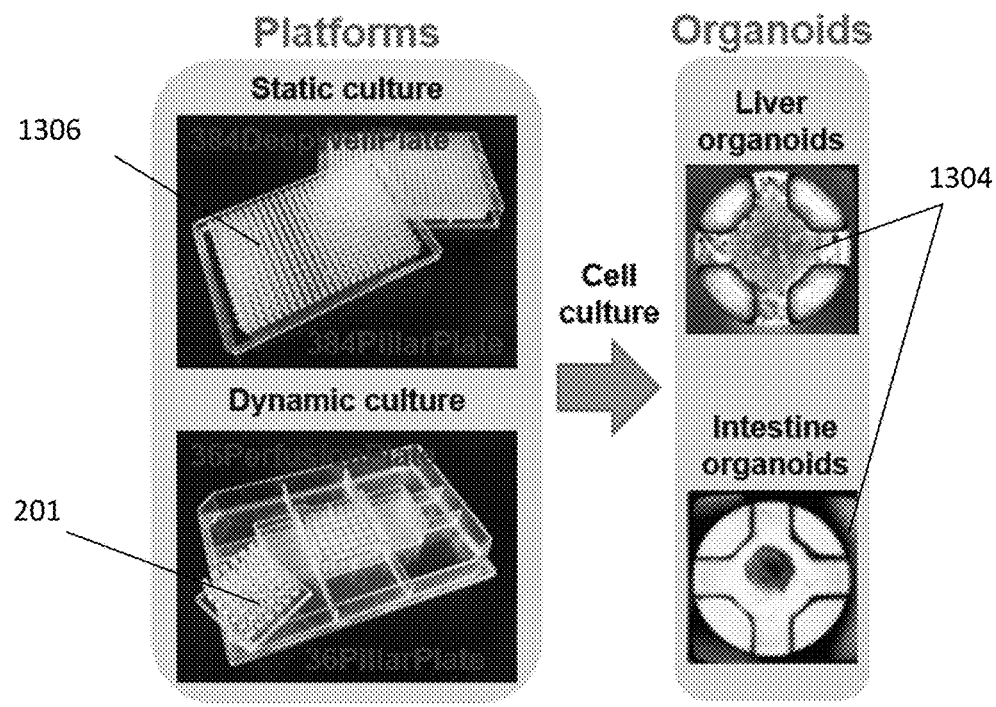

With reference to FIG. 13, in accordance with various embodiments, a method of miniature 3D bioprinting for organoid culture 1300 can comprise printing (e.g., rapid cell printing) or loading (e.g., manual cell loading) stem cells onto platforms, culturing the cells to form organoids 1304, and analyzing the organoids 1304 via at least one of real time imaging, functional assays, disease modeling, or compound screening. In various embodiments, pluripotent stem cells (PSCs) and cell aggregates suspended in biomimetic hydrogels can be printed on the pillar plates (see FIG. 1) precisely with a 3D bioprinter. After hydrogel gelation, the pillar plates containing PSCs can be sandwiched with a deep well plate 1306 or a perfusion well plate 201 with differentiation and maturation media for static and dynamic cultures of organoids. Bioprinted organoids can be tested with compounds, stained with fluorescent dyes and antibodies, and scanned with an automated fluorescence microscope for high-content imaging (HCI) of organoid functions as well as predictive assessment of compound toxicity.

Figure 14A:
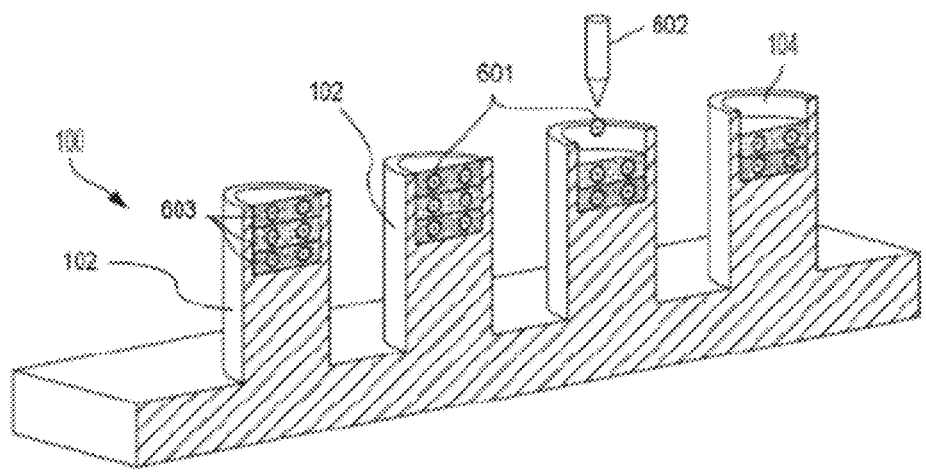
FIG. 14A shows a sectional view of embodiments of pillar-microwells containing cells printed in layers.
Figure 14B:
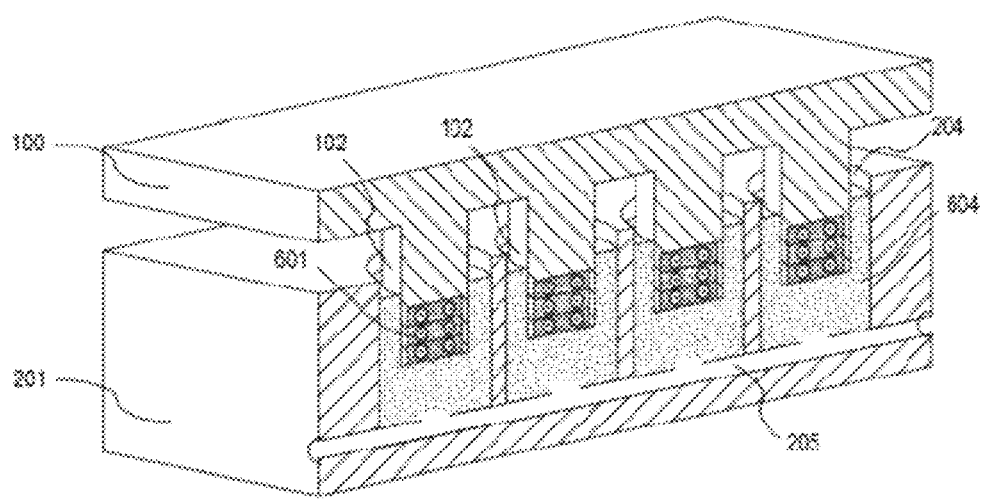
FIG. 14B shows a sectional view of embodiments of pillar-microwells containing cells positioned in perfusion wells by sandwiching the pillar plate onto the perfusion plate.

Referring to FIGS. 14A-14B, the pillar plate 100 and perfusion plates 201 enable several methods for microarray 3D bioprinting. One exemplary method generally comprises dispensing cells 601 into the microwell 104 of at least one pillar 102 and incubating the cells to create a desired mini-bioconstruct. In some exemplary embodiments, the mini-bioconstructs can be created to mimic particular tissues such as, but not limited to, a heart, liver, or brain. For example, human liver tissue constructs can be created by printing primary hepatocytes/HepaRG, hepatic sinusoidal endothelial cells, hepatic stellate cells, and Kupffer cells layer-by-layer in Matrigel to maintain liver-specific functions. Also, for example, human brain organoids can be generated by printing neural stem cells in Matrigel and differentiating into different neural lineages for several months.

Referring to FIG. 14A, in some exemplary methods, cells 601 are dispensed into the pillar-microwell 104 of each pillar 102 of the pillar plate 100 by a microarray spotter 602. In various embodiments, the cells 601 can include viral particles. A microarray spotter 602 is a robotic device capable of dispensing small amounts of liquid, also known as "spots." In some exemplary methods, the microarray spotter 602 can be capable of printing spots into multiple pillar-microwells 104 on the same pillar plate 100. The microarray spotter can be capable of printing from about 20 nL to about 5000 nL of cells into the pillar-microwells 104. Exemplary microarray spotters include S+ MicroArrayer and ASFA™ spotter, commercially available from Samsung, and MBD Korea, as well as MicroSys, PixSys, and CellJet from DigiLab.

In some exemplary methods, prior to dispensing cells, a cell suspension 603 can be made comprising the cells, at least one hydrogel, and growth media. Optionally, one or more biomolecules, drugs, DNAs, RNAs, proteins, bacteria, viruses, or combinations thereof can be included in the cell suspension. For example, the biomolecules, drugs, DNAs, RNAs, proteins, bacteria, viruses, or combinations thereof can be chosen to mimic a particular biological environment, such as particular tissue (liver, heart, brain, etc.).

A hydrogel is generally a polymer that contains water. For example, suitable hydrogels can be alginate, methacrylated alginate, chitosan, hyaluronic acid, fibrinogen, collagen, methacrylated collagen, PuraMatrix, Matrigel, PepGel, and polyethylene glycol. The cells can be entrapped in a hydrogel using various mechanisms such as, but not limited to, ionic, photo, enzymatic, and chemical crosslinking. Crosslinking agents can include salts or enzymes that facilitate gelling of the hydrogel. Examples of suitable crosslinking mechanisms include ionic crosslinking (e.g., alginate with barium chloride and calcium chloride; PuraMatrix with salts), affinity/covalent bonding (e.g., functionalized polymers with streptavidin and biotin), photopolymerization (e.g., methacrylated alginate with photoinitiators), and biocatalysis (e.g., fibrinogen with thrombin).

The cell suspension concentration can be from about 10,000 to about 20 million cells/mL, about 500,000 to about 5 million cells/mL, or about 1 million to about 2 million cells/mL. The growth media can be from about 90 w/v % to about 99.9 w/v % of the final cell suspension. The hydrogel can be from about 0.1 w/v % to about 10 w/v % of the final cell-suspension.

Growth media is generally a liquid designed to support cell growth, differentiation, and maturation. Suitable examples of growth media can include Dulbecco's Modified Eagle Medium (DMEM), Roswell Park Memorial Institute Medium (RPMI), and William's E Medium. Biomolecules can include molecules that support cellular or tissue growth, such as extracellular matrices (ECMs), growth factors, compounds, cytokines, and carbohydrates.

In some further exemplary methods, prior to dispensing the cells with the microarray spotter 602, the pillar-microwells 104 are treated with plasma or coated with functional polymers for cell spot attachment and hydrogel gelation.

Referring to FIG. 14B, the cells are positioned between the pillar plate 100 and the perfusion plate 201. The perfusion wells 204 are filled with cell aggregates 601 and growth media 604. The pillars 102 of the pillar plate have been inserted into the perfusion wells 204. The microchannels 205 fluidly connect the perfusion wells 204 and thus fluidly connect the pillar-microwells and the cells within the pillar-microwells.

Figure 14C:
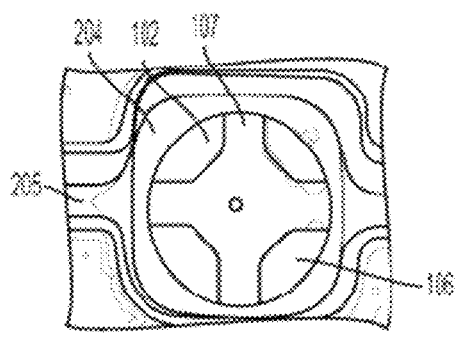
FIG. 14C shows a close-up view of a pillar inserted in a perfusion well.

FIG. 14C shows a view of the bottom of the perfusion well 204 with a pillar 102 having four slits 107 and four sidewalls 106 inserted into the perfusion well. The perfusion channels 205 that connect the perfusion well 204 to the reservoirs are visible. The transparent plate can be attached to the bottom of the perfusion plate by using ultrasonic welding or glue. The perfusion plate can be manufactured in two pieces; the perfusion plate with wells that does not have a bottom, and a bottom plate that is attached to the perfusion plate.

Figure 15A:
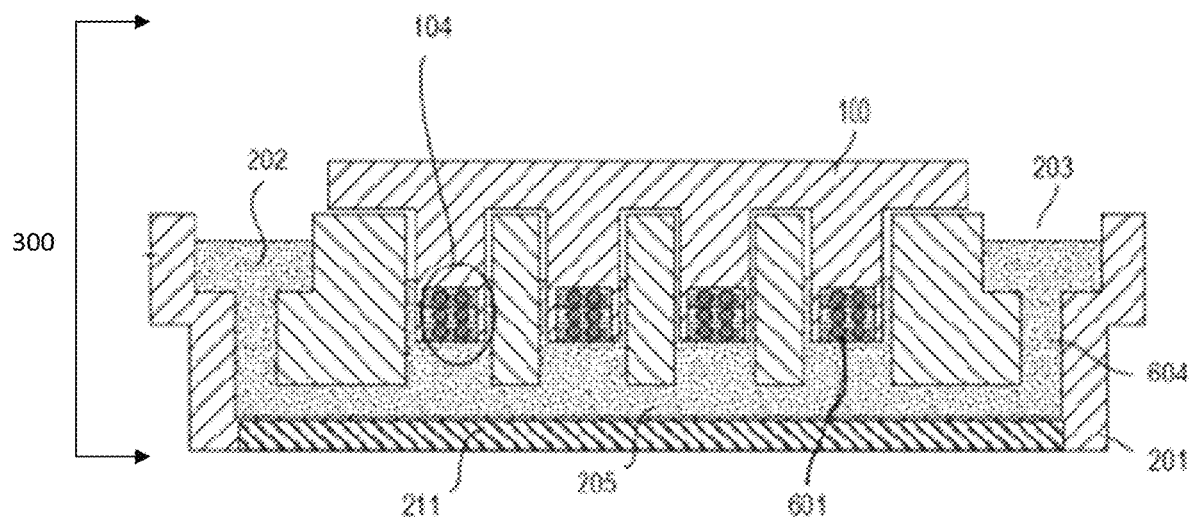
FIG. 15A shows a cross-sectional view of an embodiment of a pillar plate with cells engaged with an embodiment of a perfusion plate with reservoirs and microchannels.
Figure 15B:
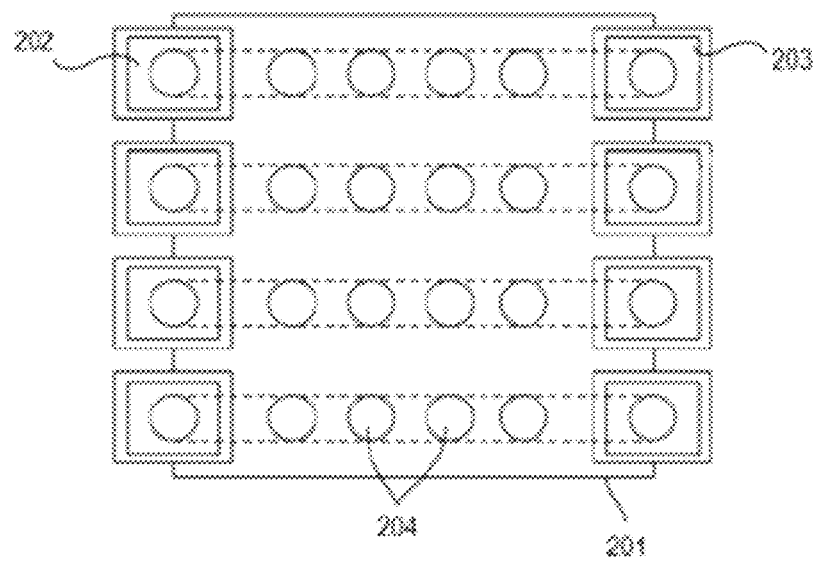
FIG. 15B shows a top view of an embodiment of a perfusion plate with reservoirs, microchannels, and perfusion wells.

Referring to FIGS. 15A and 15B, the assembly 300 is illustrated in accordance with various embodiments described herein. In some exemplary methods, the pillar plate 100 with cell aggregates 601 can be incubated by submerging the pillar-microwells 104 in a perfusion plate 201 containing growth media 604. This method can, for example, be used for long term cultures and can mimic circulatory systems to study, for example, organ-organ interactions. The one or more perfusion wells 204 can contain growth media 604 that flows from an inflow reservoir 202 to an outflow reservoir 203 through the perfusion channels 205. The growth media 604 can contain test compounds, biomolecules, drugs, DNAs, RNAs, proteins, bacteria, cells, viruses, or combinations thereof that can flow through or reside in the one or more channels 205. For example, an embodiment of the perfusion plate 201 can contain one compartment for liver co-cultures, one compartment for brain cell co-cultures and porous microchannels (not shown) simulating the blood brain barrier positioned and between perfusion wells, such that the growth media 604 or other fluid must pass through the porous microchannels before reaching the next perfusion well in a row of perfusion wells, for example positioned in a microchannel. simulating the blood brain barrier. As shown in FIG. 15A, a pillar plate 100 containing pillar-microwells 104 or conventional pillars with a flat surface tip can be engaged with the perfusion channel plate 201 so that the contents on the pillar or in the pillar-microwell 104 can be in contact with the growth media 604 in the channel 205. As shown in FIG. 15B, the perfusion channel plate can contain perfusion wells 204 through which a pillar or pillar-microwell 104 can be inserted. The perfusion plate can have a transparent plate 211 attached to its bottom.

In some exemplary embodiments, after a mini-bioconstruct is created, at least one biosample can be added. Suitable biosamples can include biomolecules, drugs, DNAs, RNAs, cells, growth factors, extracellular matrices, proteins, viruses, bacteria, cells, or combinations thereof. The at least one biosample can be chosen to mimic a particular biological environment or condition. In some exemplary embodiments, the at least one biosample can be printed directly onto the mini-bioconstruct, whether contained in a pillar-microwell 104, using the microarray spotter 602. In some further exemplary embodiments, the at least one biosample can be printed into the wells of a conventional microtiter plate using the microarray spotter; then the pillar-microwells 104 containing mini-bioconstructs can be inserted into the microtiter wells containing biosamples or other mini-bioconstructs.

In some exemplary embodiments where the mini-bioconstruct is created in the inventive perfusion well plate 201, biosamples or biomolecules can be added by engaging the pillar plates that have been prepared with at least one biosample or biomolecule.

Figure 16A:
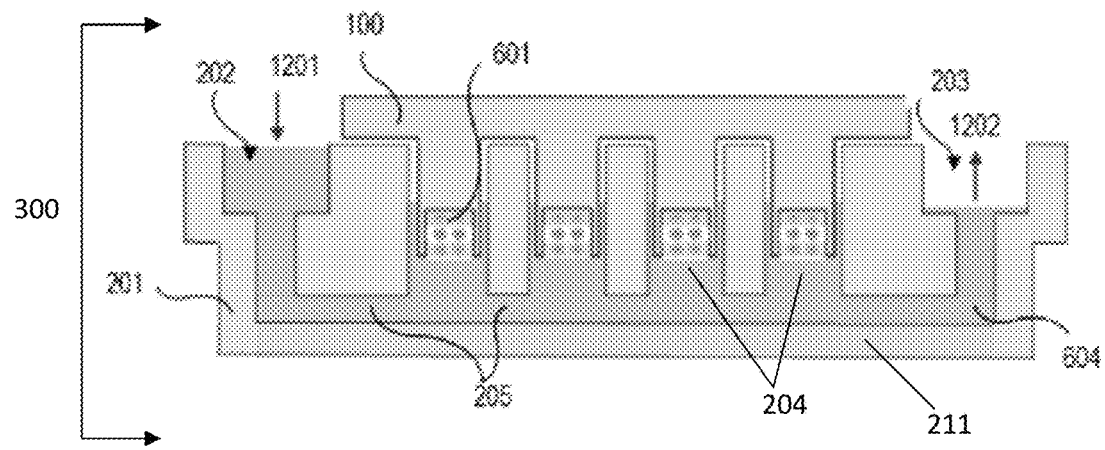
FIG. 16A shows the operation of a perfusion plate to generate a unidirectional flow according to an exemplary embodiment.
Figure 16B:
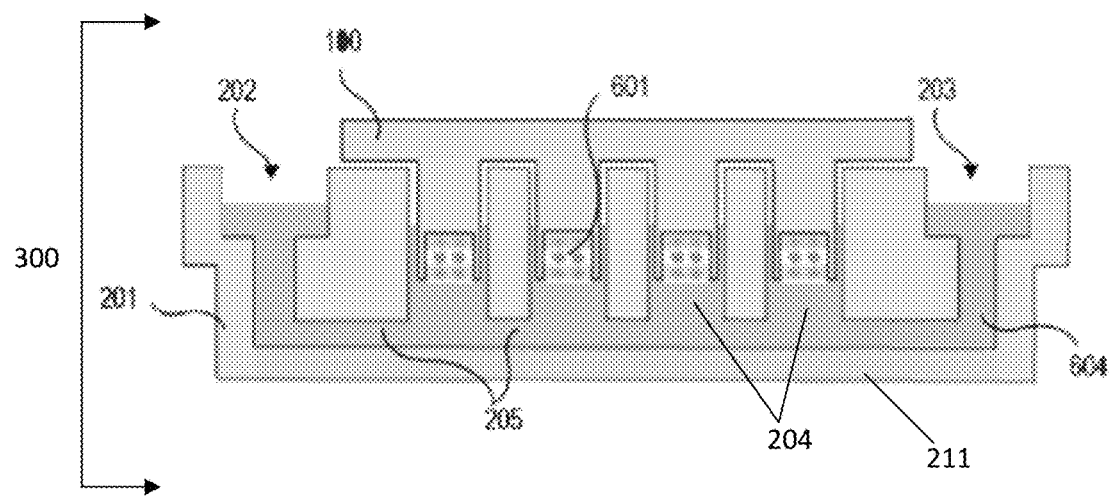
FIG. 16B shows the operation of a perfusion plate to generate a unidirectional flow according to an exemplary embodiment.
Figure 16C:
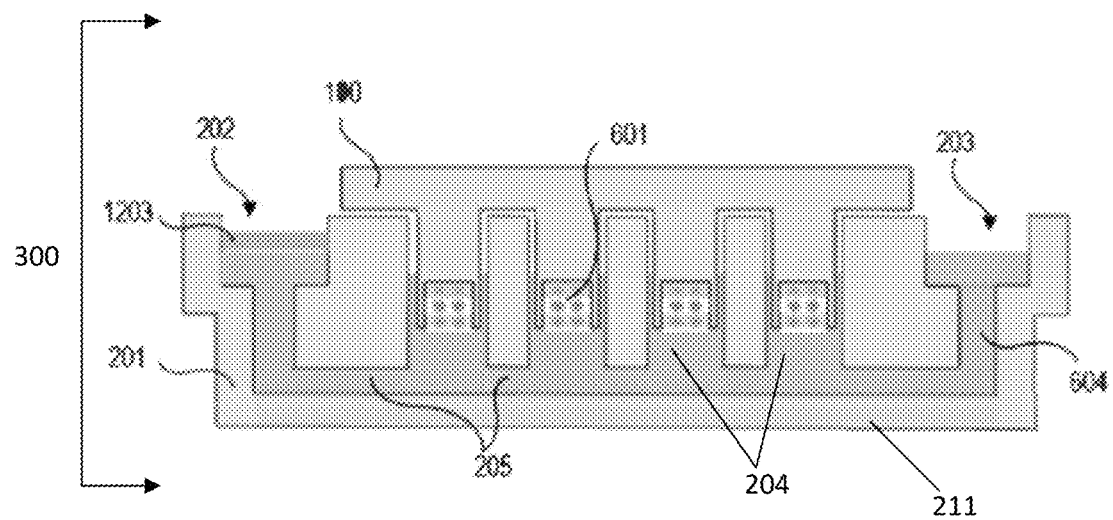
FIG. 16C shows the operation of a perfusion plate to generate a unidirectional flow according to an exemplary embodiment.

Referring now to FIGS. 16A-16C, the fluid flow operation of the perfusion plate 201 is illustrated. The velocity of the unidirectional flow can depend on the volume and number of the reservoirs and channels. The perfusion plate 201 can have a first flow and a second flow, wherein the second flow is faster than the first flow. The first flow can be slower than the second flow due to the addition of fresh growth media 604. FIG. 16A is an illustration of removing old growth media 604 in the outflow reservoirs 203 as indicated by arrow 1202, and adding 1000 µL of fresh growth media 604 in the inflow reservoirs 202, as indicated by arrow 1201. FIG. 16B is an illustration of the growth media 604 reaching an equilibrium between the inflow reservoir 202 and the outflow reservoir 203 after about 3 hours. FIG. 16C illustrates the addition of 0.3 to 0.5 mL of fresh growth media 1203 to generate a unidirectional flow that is slower than when the additional fresh growth media 1203 was added. While FIGS. 16A-16C illustrate a single inflow reservoir 202 and outflow reservoir 203, in the exemplary embodiments described herein, there can be multiple inflow reservoirs and outflow reservoirs, as many as one for each row of perfusion wells 204.

In various embodiments, the geometry of the fluidic microchannels 205 provides control of the fluid flow without the use of a pump and/or rocker plate. For example, in some exemplary embodiments, the dimension of the microchannels 205 can be, but is not limited to, 0.2 mm (width) by 0.2 mm (height) by 1.2 mm (length), the dimension of the perfusion well 204 can be, but is not limited to, 3.2 mm (width) by 3.2 mm (length) by 13 mm (height), and the dimension of the inflow reservoir 202 and outflow reservoir 203 can be, but is not limited to, 3.2 mm (width) by 20 mm (length) by 16 mm (height). The flow can be generated by adding more fluid, which can be growth media 604, to the inflow reservoir 202 and/or removing fluid from the outflow reservoir 203. The flow can be induced by gravity and the geometry of the reservoirs and channels, and the direction of the flow is indicated by inflow arrow 1201 and outflow arrow 1202 in FIG. 16A. Cells 601 are positioned in the pillar-microwells of the pillar plate 100, which is engaged with the perfusion plate 201 such that the pillar-microwells are each inserted in to the perfusion wells. The assembly 300 described herein can be compatible with a pump and/or a rocker plate, but a pump and/or rocker plate is not required for fluid flow. The reservoirs and channels can have a coating that is hydrophilic. The hydrophilic coating can made by amphiphilic polymers, including poly(maleic anhydride-alt-1-octadecene) (PMA-OD), poly(maleic anhydride-alt-1-tetradecene) (PMA-TD), and polyethylene oxide-maleic anhydride copolymers, including ACM1510, ADM1510, AEM1510, AKM0530, and AKM1510, amphiphilic surfactants, including Brij C2 and C10, hydrogels, including alginate, collagen, PuraMatrix, fibrinogen, fibronectin, and Matrigel, and other hydrophilic polymers, including polydopamine, poly(2-hydroxyethyl methacrylate) (pHEMA), and poly-L-lysine (PLL) to enhance the hydrophilicity of the surface. The hydrophilic coating in the channels and reservoirs serves a different purpose from the hydrophilic coating in the wells of the pillars and perfusion wells. In the microchannels and the reservoirs, the hydrophilic coating encourages fluid flow of the growth media from the inflow reservoir to the outflow reservoir without air bubble entrapment.

The inflow reservoir 202 and outflow reservoir 203 can have different features from each other. The perfusion well plate 201 can be made from polystyrene. The inflow reservoir 202 and outflow reservoir 203, microchannel 205, and perfusion well 204 geometry can generate unidirectional flow without a pump and/or rocker plate for up to 3 hours, and in some circumstances, up to 24 hours. In still other circumstances, the inflow reservoir 202 and outflow reservoir 203, microchannel 205, and perfusion well 204 geometry can generate flow without a pump and/or rocker plate for up to two days, depending on the geometry and hydrophilicity of the coating. The inflow reservoir 202 and outflow reservoir 203, microchannel 205, and perfusion well 204 geometry along with a hydrophilic coating encourages the fluid to flow in one direction, from the inflow reservoir to the outflow reservoir, for unidirectional flow. The hydrophilic coating can coat the outflow reservoir 203, and can be different than a coating on the inflow reservoir 202. Hydrophilicity of each microchannel surface can be varied by coating them with different polymer solutions in perfusion wells.

Figure 17A:
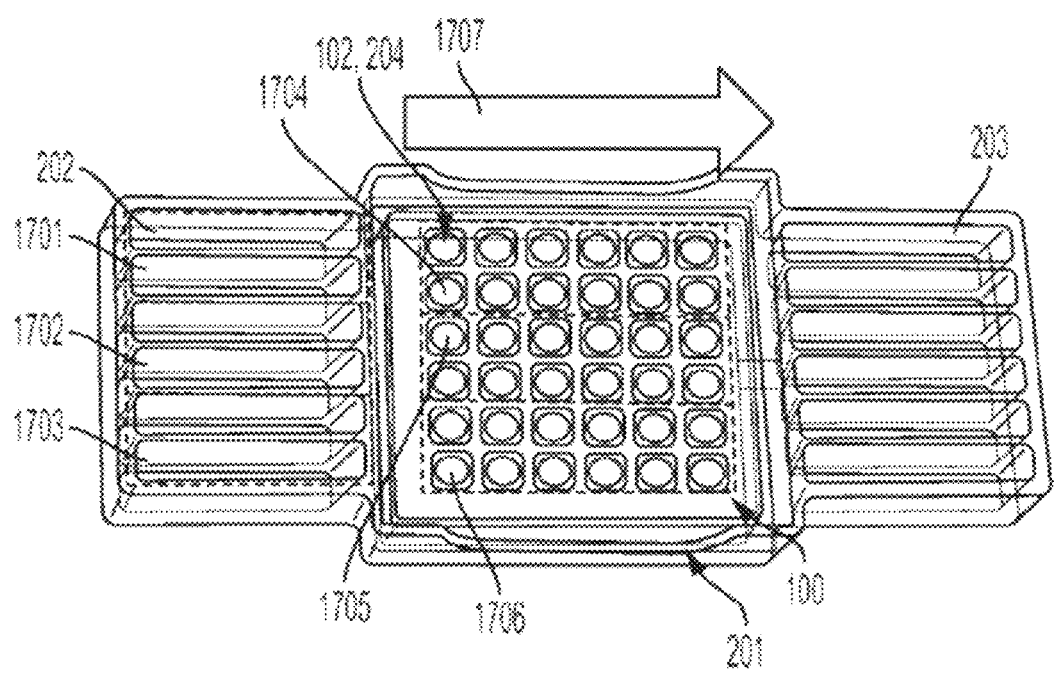
FIG. 17A shows a schematic illustration of multiple organoid communications on a pillar plate and perfusion plate assembly according to an exemplary embodiment.
Figure 17B:
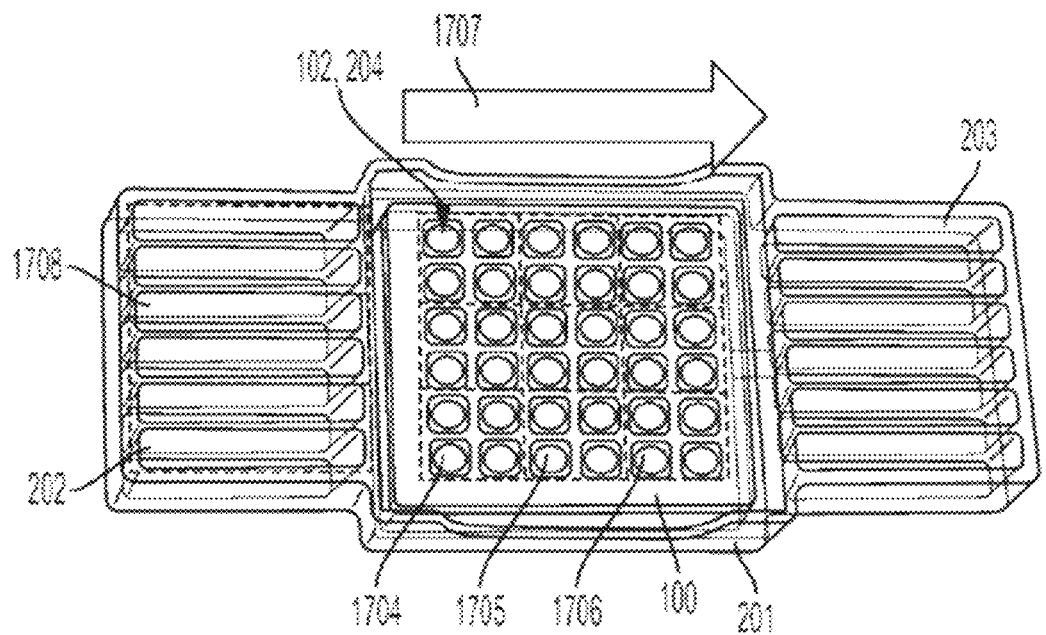
FIG. 17B shows a schematic illustration of multiple organoid communications on a pillar plate and perfusion plate assembly according to an exemplary embodiment.

The assembly 300 has the pillar plate 100 with a complementary design to the perfusion plate 201, unidirectional flow in the perfusion wells 204 without the use of pumps and rockers, a transparent plate 211 comprising a flat and clear bottom with thin glass slide or plastic film bonding for cell imaging, and a perfusion well 204 structure that avoids air bubble entrapment in its microchannels. Human cells can be cultured in combination with the perfusion well plate and detached and analyzed in microtiter well plates. Cell analysis can be done with commercially available automated fluorescent microscopes or microtiter plate readers. Referring to FIGS. 17A-17B (see Example 4), tissue-tissue communications can be performed easily by rotating the pillar plate with different tissues at a 90 degree angle.

In accordance with various embodiments, a unidirectional flow in the perfusion wells can be generated by adding growth media in a first reservoir (e.g., the outflow reservoir) and removing growth media from a second reservoir (e.g., the inflow reservoir). The perfusion plate can then be placed on a flat surface or an incubator for cell culture.

In accordance with various embodiments, a method of operating a perfusion plate can include the steps of: depositing cells into at least one pillar-microwell in a pillar on a pillar plate, submerging the at least one pillar having cells in its pillar-microwell into at least one perfusion well in a perfusion plate, wherein the perfusion plate comprises a first reservoir and a second reservoir, adding a first volume of media fluid to the first reservoir of the perfusion plate, incubating the perfusion plate and pillar plate in an incubator for cell culture, removing a second volume of media fluid from the second reservoir, and placing the perfusion plate and pillar plate on a flat surface to generate a unidirectional flow of the first volume of media fluid.

In accordance with various embodiments, a bidirectional flow in the perfusion wells can be generated by adding growth media in a first reservoir (e.g., the outflow reservoir) and from a second reservoir (e.g., the inflow reservoir) and placing the perfusion plate on a digital rocker.

In accordance with various embodiments, a method of operating a perfusion plate can include the steps of: depositing cells into at least one pillar-microwell in a pillar on a pillar plate, submerging the at least one pillar having cells in its pillar-microwell into at least one perfusion well in a perfusion plate, wherein the perfusion plate comprises a first reservoir and a second reservoir, adding a first volume of media fluid to the first reservoir of the perfusion plate, incubating the perfusion plate and pillar plate in an incubator for cell culture, removing a second volume of media fluid from the second reservoir, and placing the perfusion plate and pillar plate on a flat surface to generate a unidirectional flow of the first volume of media fluid.

EXAMPLES

Example 1

An exemplary method of operating a perfusion well plate can have the following steps: Step 1: deposit cells into at least one pillar-microwell on the pillar plate. Step 2: submerge at least one pillar-microwell with cells on its pillar into at least one perfusion well in the perfusion plate. Step 3: add a first volume of media fluid to an inflow reservoir and incubate the perfusion plate and the pillar plate in an incubator for cell culture. Step 4: after a first designated amount of time has elapsed, add a second volume of fluid to the inflow reservoir, after a certain amount of time, to generate slow, unidirectional flow. Step 5: empty the outflow reservoir and add a third volume of fluid to the inflow reservoir.

Example 2

An example of an experimental procedure to operate the perfusion well plate in accordance with various embodiments can have the following steps. Step 1: Add 1 mL of 70% ethanol in the inflow reservoirs at a tilted angle to rapidly remove air in microchannels. Step 2: Aspirate out excess ethanol collected in the outflow reservoirs by vacuum. Step 3: Add 1 mL of growth media in the inflow reservoirs at a tilted angle to remove ethanol remaining in the reservoirs, the microchannels, and the perfusion wells. Step 4: Aspirate out excess growth media collected in the outflow reservoirs by vacuum. Step 5: Repeat Steps 3 and 4 twice to completely remove the ethanol. Step 6: Place the perfusion well plate flat and engage the pillar plate with human cells onto the perfusion well plate, so that the human cells are positioned between at least one pillar and a corresponding perfusion well. Step 7: Add 1 mL of fresh growth media in the inflow reservoirs and incubate the engaged plates in a $CO_2$ incubator for cell culture. Step 8: After approximately 3 hours, add 0.3-0.5 mL of fresh growth media in the upper reservoirs to generate slow, unidirectional flow. Step 9: Every 1-2 days, empty the outflow reservoirs using 1 mL pipette and add fresh growth media in the inflow reservoirs for cell culture.

Example 3

Figure 18A:
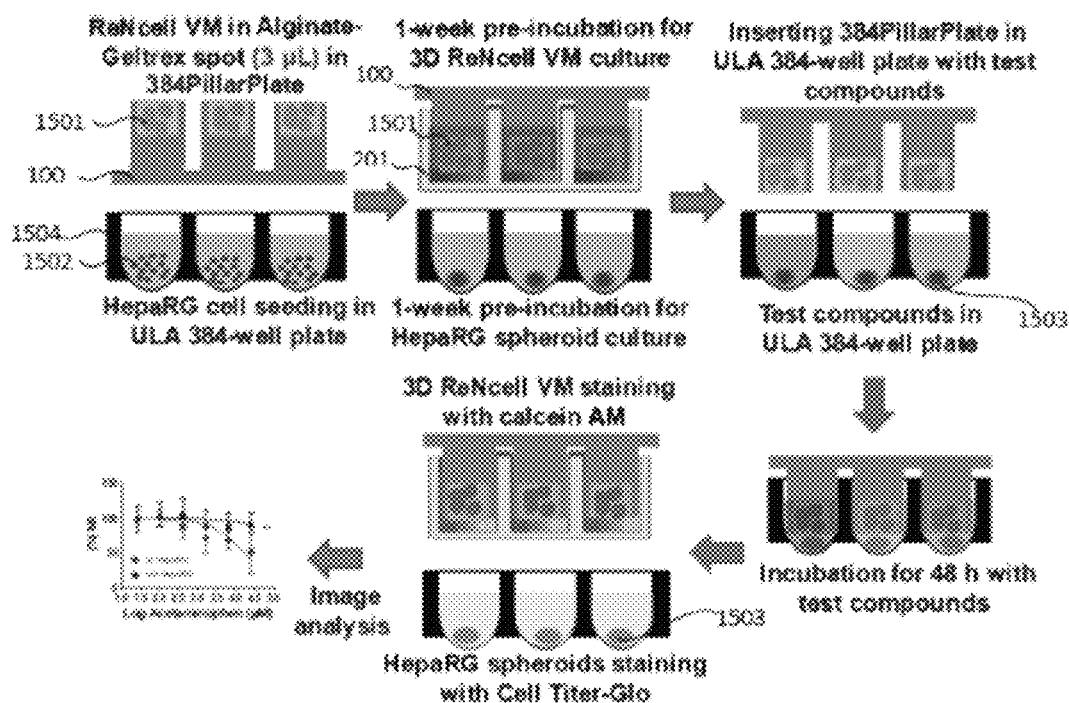
FIG. 18A shows a schematic illustration of cell-cell communications using cell spheroids on a pillar plate with cell aggregates in a ULA well plate.

Referring now to FIG. 18A, schematics of an exemplary experimental procedure for facilitating tissue growth where two cell types can be incubated and grown at the same time is illustrated. Generally in this method, cell aggregates can be cultured in a pillar plate at the same time that cell spheroids are cultured in a ULA plate. The method is not limited to a ULA plate, but a microtiter or perfusion plate can also be used in place of the ULA plate throughout this exemplary method. Further, the cell aggregates can be cultured in a ULA, microtiter, or perfusion plate, while the cell spheroid can be cultured in the pillar plate. A pre-incubation stage can take place, in which the cell aggregates in one plate (for example, the pillar plate) can be cultured at the same time the cell spheroids are cultured in another plate (for example, the ULA plate). The cell aggregate on the pillar plate can be encapsulated with a hydrogel according to the methods described herein. Test compounds can be added to the ULA plate, and the pillar plate can be inserted in the ULA plate. The cell aggregates, cell spheroids, and test compounds can be incubated for another time period. After that, the cell aggregates and cell spheroids can be tested.

Specifically referring now to FIG. 18A, a schematic of experimental procedures for metabolism-mediated neurotoxicity by liver-brain interactions is illustrated. The metabolism-induced neurotoxicity of compounds was assessed with 3D-cultured ReNcell VM 1501 on the 384-pillar plate coupled with HepaRG cell spheroids and acetaminophen in a ULA 384-well plate. ReNcell VM was encapsulated in 0.75% (w/v) alginate and 2.5 mg/mL Geltrex and cultured in 3D on the 384-pillar plate for 7 days. HepaRG cells 1502 were incubated for 7 days in the ULA 384-well plate to form spheroids 1503 and maintain high hepatic functions prior to compound exposure. The pillar plate with ReNcell VM was inserted into the ULA plate with HepaRG spheroids and test compounds. Compound exposure in the ReNcell VM (1501) and HepaRG co-culture system was performed for 2 days. Then, the 3D ReNcell VM was stained with calcein AM and the HepaRG spheroids was stained with Cell Titer-Glo. An image analysis was then performed, and the results illustrated in the graph in FIG. 18A. The method of culturing cell spheroids and/or creating an organotypic tissue construct is not limited to the exemplary method described herein, and can be any conventional method used prior to engaging the pillar plate with ULA well plates or traditional microtiter well plates or perfusion well plates.

Figure 18B:
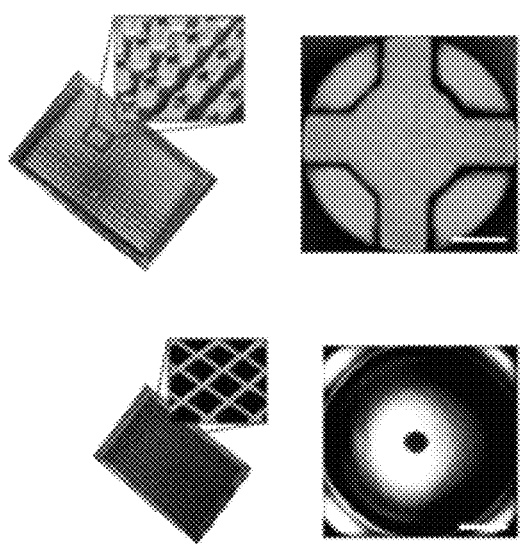
FIG. 18B shows HepaRG cell spheroids on a pillar plate and ReNcell VM aggregates in a ULA well plate to determine metabolism-induced neurotoxicity by HepaRG and ReNcell VM.

Referring now to FIG. 18B, images of the 384-pillar plate and the ULA 384-well plate with organotypic cells are shown. The top row of images in FIG. 16B show the 384-pillar plate with 3D-cultured ReNcell VM, and the bottom row of images show the ULA 384-well plate with HepRG spheroids.

Figure 19A:
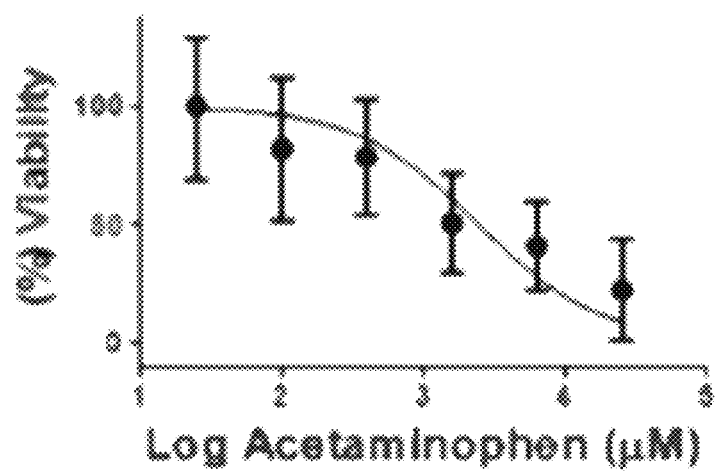
FIG. 19A shows an exemplary dose response curve obtained by HepaRG cell spheroids exposed to acetaminophen.
Figure 19B:
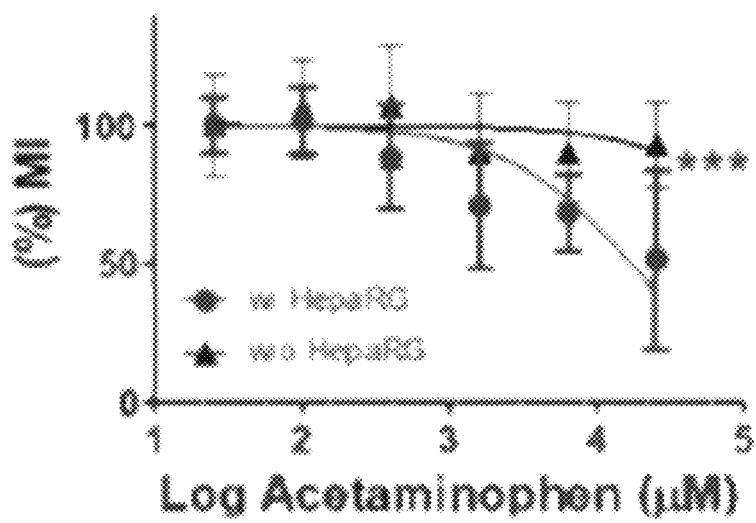
FIG. 19B shows an exemplary dose response curves obtained by ReNcell VM aggregates exposed to acetaminophen alone (no HepaRG) and acetaminophen with HepaRG cell spheroids to determine metabolism-induced neurotoxicity.

FIGS. 19A and 19B show dose response curves corresponding to FIGS. 18A and 18B, respectively. After creating organotypic neural stem cell spheroids on the pillar plate, tissue-tissue interactions have been facilitated by (1) engaging the pillar plate 100 with ULA plates 1504 with liver cell spheroids and a test compound or (2) engaging the pillar plate with ULA plates 1504 with a compound alone. This approach allows rapid investigation of two organ communications for disease modeling and predictive drug screening. FIG. 19A shows a dose response curve of HepaRG cell spheroids in the ULA 384-well plate tested with acetaminophen. Cell viability was measured by the Cell Titer-Glo assay. FIG. 19B shows dose response curves of 3D-cultured ReNcell VM on the 384-pillar plate tested with HepaRG spheroids in the ULA 384-well plate in the presence of acetaminophen. For cell viability, membrane integrity of 3D-cultured ReNcell VM was measured with calcein AM staining. In FIGS. 19A and 19B, *** is for $p<0.001$.

Example 4

With reference to FIGS. 17A-B, the perfusion plate of the exemplary embodiments described herein can also be used for testing compounds (as shown in FIG. 17). The cells on the pillar plate can be exposed to compounds by supplying growth media containing compounds in the perfusion plate. In other exemplary methods of testing cells, a conventional ULA well plate without perfusion can be used to test the cells after they have been grown and/or incubated by sandwiching a pillar plate with cells onto a ULA well plate containing compounds and/or cells (as shown in FIG. 18A).

Referring generally now to FIGS. 17A and 17B, the exemplary embodiments and methods described herein can be used to facilitate tissue to tissue communication; that is, communication between more than one tissue type. In the exemplary embodiments having one tissue type on a pillar plate and another in the wells of a ULA plate (such as the cell aggregates and cell spheroids illustrated in FIG. 18A for example), the tissue to tissue communication occurs when the plates are in contact with each other. In an exemplary embodiment, each row of a pillar plate can have its own type of cell aggregate, which can be encapsulated according to the methods described herein. Each row of wells in a ULA plate, or microtiter plate, or perfusion plate, can have cell spheroids or cell aggregates of its own tissue type. The sandwiching of the pillar plate with the ULA (or microtiter or perfusion) plate in a first orientation can align the cell aggregates in the first row of pillars with the cell spheroids in the first row of wells. However, rotation of the pillar plate and sandwiching it again into the plate having wells, provides communication between the cell spheroids in the first row of pillars with each of the cell spheroid types, one with each spheroid type, because a row of pillars that was previously horizontal is now vertically aligned with the plate having wells.

Referring specifically now to FIGS. 17A and 17B, a schematic illustration of a specific example of tissue to tissue communication is shown. Multiple organ communications on the 36-pillar plate 100 having 36 pillars 102 with liver, pancreas, and intestine organoids positioned onto the 36-well perfusion plate 201 having 36 perfusion wells 204 is shown. FIG. 17A illustrates that liver organoids 1704, pancreas organoids 1705, and intestine organoids 1706 printed on the 36-pillar plate 201, where each cell type is printed on two 6-pillar arrays, can be cultured using individual growth media (i.e., growth media for liver organoids 1701, growth media for pancreas organoids 1702, and growth media for intestine organoids 1703) in the inflow reservoirs 202 supplied through the microchannels to the perfusion wells by flowing in a direction from the inflow reservoirs 202 to the outflow reservoirs 203 as indicated by arrow 1707. FIG. 17B illustrates that the 36-pillar plate can be rotated 90 degrees, and then liver, pancreas, and intestine organoids were connected by supplying universal growth media 1708 optimal for the three tissues. Six different compounds in universal growth media were tested simultaneously to investigate three tissue interactions. By encapsulating the cells on the pillar plate, the plates are able to be rotated and sandwiched in the rotated position. Any number of rows of pillars can be used on the pillar plate. Further, this rotation to facilitate tissue to tissue interaction can be performed with a pillar plate and any other plate, such as a ULA plate, a microtiter plate, and a perfusion plate according to the embodiments described herein.

Example 5

Figure 20A:
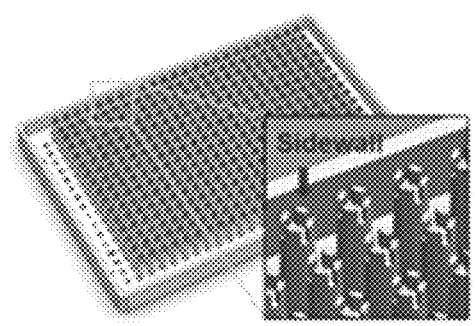
FIG. 20A shows a 384PillarPlate in accordance with various embodiments.
Figure 20B:
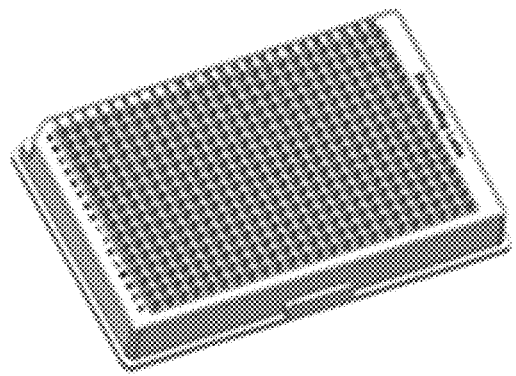
FIG. 20B shows a 384DeepWellPlate in accordance with various embodiments.
Figure 20C:
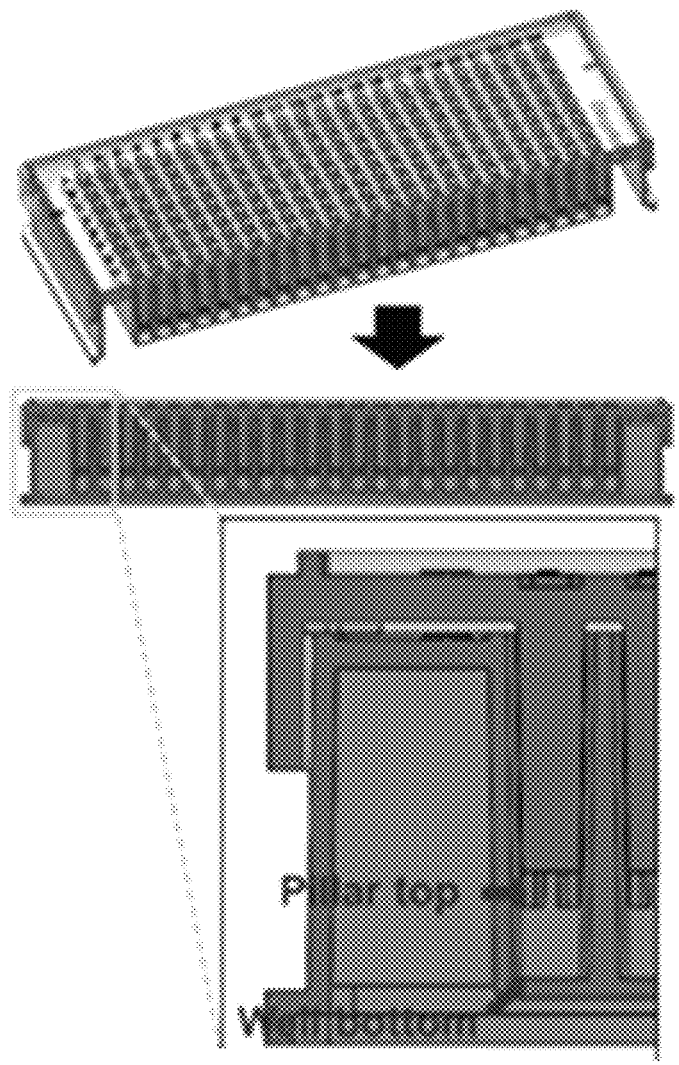
FIG. 20C shows a 384PillarPlate sandwiched onto a 384DeepWellPlate in accordance with various embodiments.
Figure 20D:
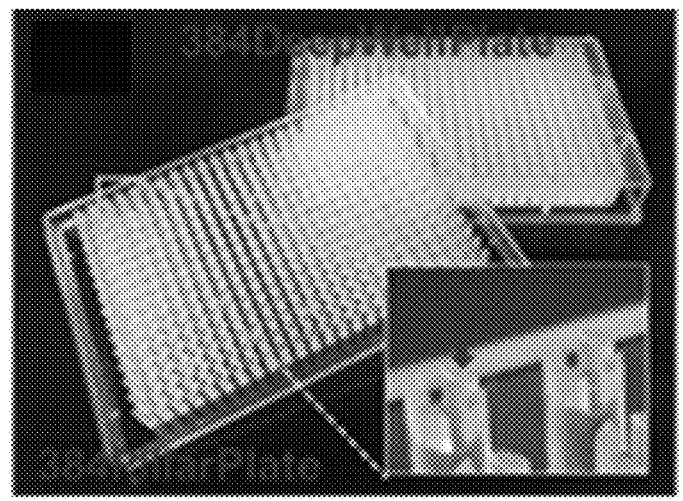
FIG. 20D shows a 384PillarPlate in accordance with various embodiments.
Figure 20E:
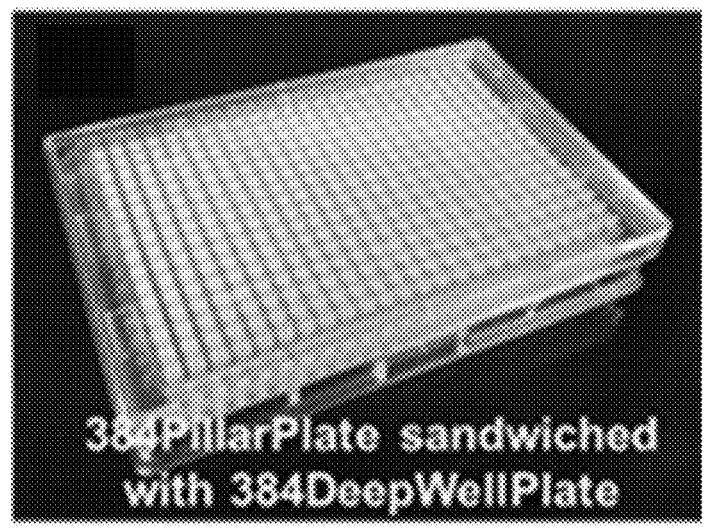
FIG. 20E shows a 384DeepWellPlate in accordance with various embodiments.

With reference to FIGS. 20A-E, a pillar plate and a deep well plate can be used for static organoid culture in accordance with various embodiments herein. A 384PillarPlate (FIG. 20A), a 384DeepWellPlate (FIG. 20B), and a 384PillarPlate sandwiched onto a 384DeepWellPlate (FIG. 20C). Sidewalls and slits on the pillars are designed for stem cell printing and robust spot attachment for long-term static organoid culture. Injection molding with polystyrene was performed to manufacture the 384PillarPlate (FIG. 20D) and the 384DeepWellPlate (FIG. 20E) for static organoid culture. With reference to FIG. 20C, there is a space between the top of pillars and the bottom of perfusion wells to accommodate enough cell culture media while allowing cell imaging. A highly versatile 384PillarPlate with sidewalls and slits and a complementary 384DeepWellPlate can be manufactured via injection molding of polystyrene to support 3D cell cultures and organoid cultures with an array of human cell types for various HTS assays. A single 384PillarPlate contains 384 pillars onto which an array of human organoid culture has been dispensed using a 3D bioprinter and a multichannel pipette (see FIG. 25A, which illustrates experimental procedures for cell printing and organoid culture on the pillar plate). Prior to injection molding, various shapes and structures of pillars with sidewalls and slits were tested via 3D printing of plastics for optimum cell printing, formation of a gel for cell encapsulation, and analysis of 3D cells in different layers for high-content imaging (HCI) assays for miniature tissue regeneration. The 384PillarPlate (FIG. 20A) with the following dimensions was manufactured by injection molding: the pillar-to-pillar distance (4.5 mm), the height of pillars (11.6 mm), and the diameter of pillars (outer 2.5 mm and inner 1.5 mm). The unique sidewall and slit structure on the 384PillarPlate ensured robust cell spot attachment for HCI and immunofluorescence assays as compared to the pillars with a flat surface. In addition, hydrophilic surface functionalization of the pillar plates was performed to avoid air bubble entrapment on top of the pillars, retain cell spots in hydrogels over a long period of time (typically 4 weeks), and prevent 2D cell growth on the pillar surface. The pillar plates were coated with poly(maleic anhydride-alt-1-octadecene) (PMA-OD) and then treated with a mixture of poly-L-lysine (PLL) and CaCl2 to create thin alginate coating on top of the pillars. Alginate coating had a high compatibility with Matrigel for long-term cell encapsulation and was non-adhesive to cells to avoid 2D cell growth. Each pillar can accommodate the optimum volume of 5 μL of hydrogels containing PSCs and the maximum volume of 7 μL. Polystyrene used for injection molding of the 384PillarPlate is nontoxic for cell culture and transparent for image acquisition of organoids. The 384DeepWellPlate built on a footprint of conventional 384-well plates has 384 deep wells and is complementary to the 384PillarPlate to accommodate growth media for cell culture and reagents for cell staining. The 384DeepWellPlate (FIG. 20B) with the following dimensions was manufactured by injection molding: the well-to-well distance (4.5 mm) and the width, length, and depth of wells (3.5, 3.5, and 14.7 mm). Each deep well can accommodate the maximum volume of 120 μL of solutions, and the optimum volume allowed after sandwiching with the 384PillarPlate is 80 μL for static organoid culture without the overflow. By sandwiching the 384PillarPlate onto the 384DeepWellPlate, various biochemical and cell-based assays can be performed in the plate system

Example 6

Figure 21A:
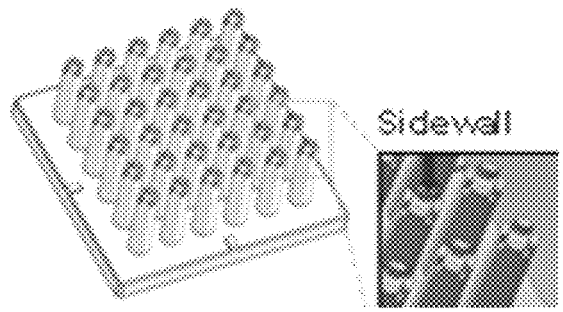
FIG. 21A shows a 36PillarPlate in accordance with various embodiments.
Figure 21B:
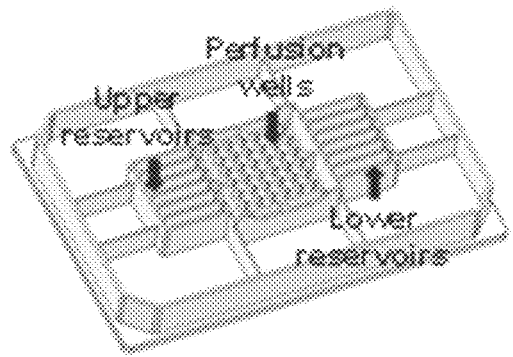
FIG. 21B shows a 36PerfusionPlate in accordance with various embodiments.
Figure 21C:
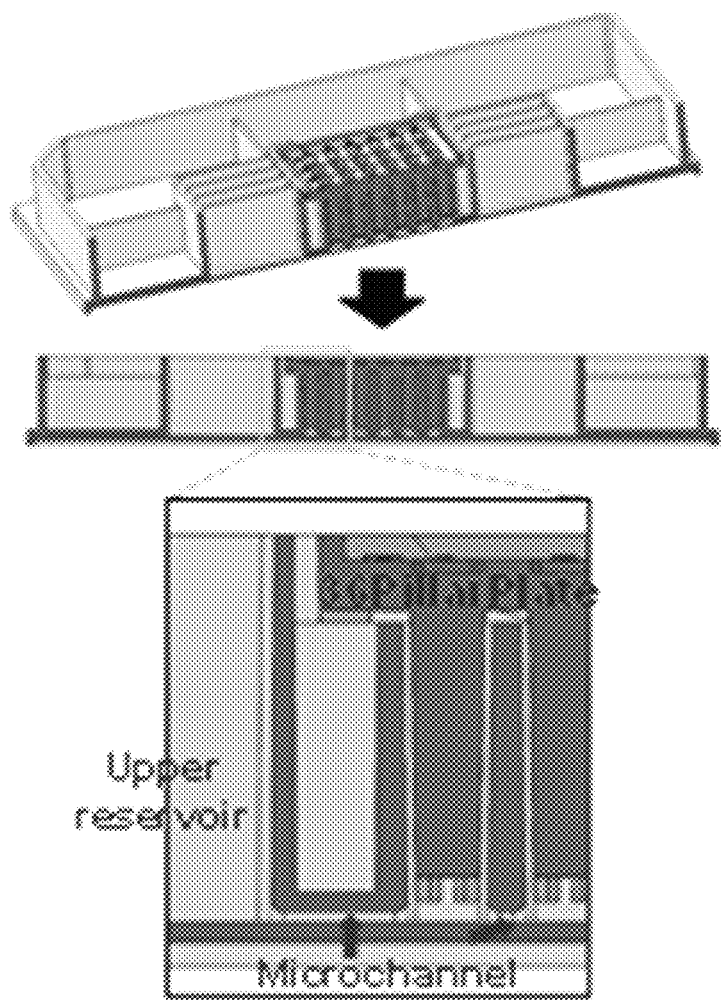
FIG. 21C shows a 36PillarPlate sandwiched onto a 36PerfusionPlate in accordance with various embodiments.
Figure 21D:
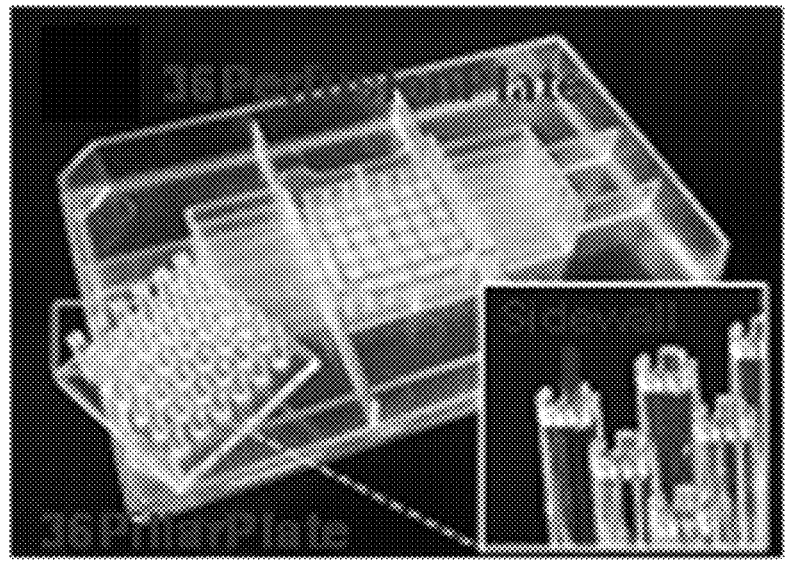
FIG. 21D shows a 36PillarPlate in accordance with various embodiments.
Figure 21E:
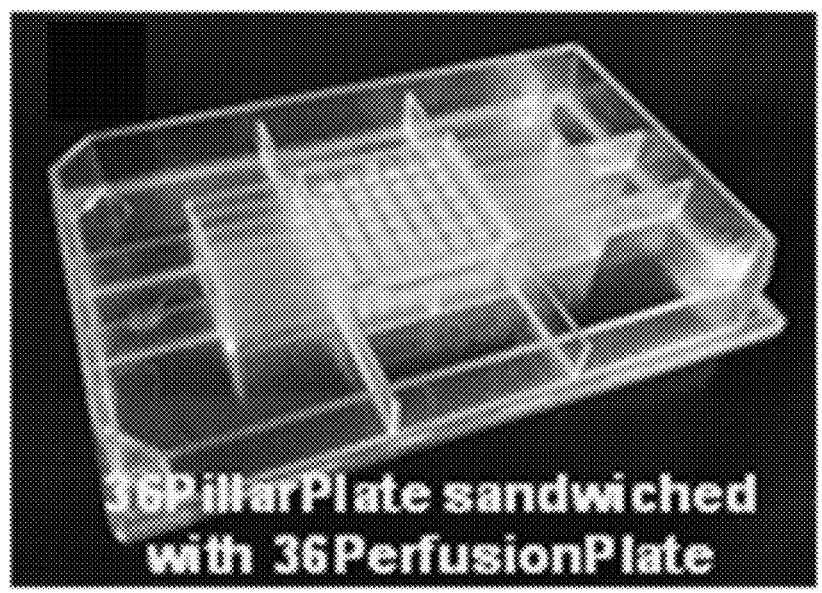
FIG. 21E shows a 36PerfusionPlate in accordance with various embodiments.
Figure 21F:
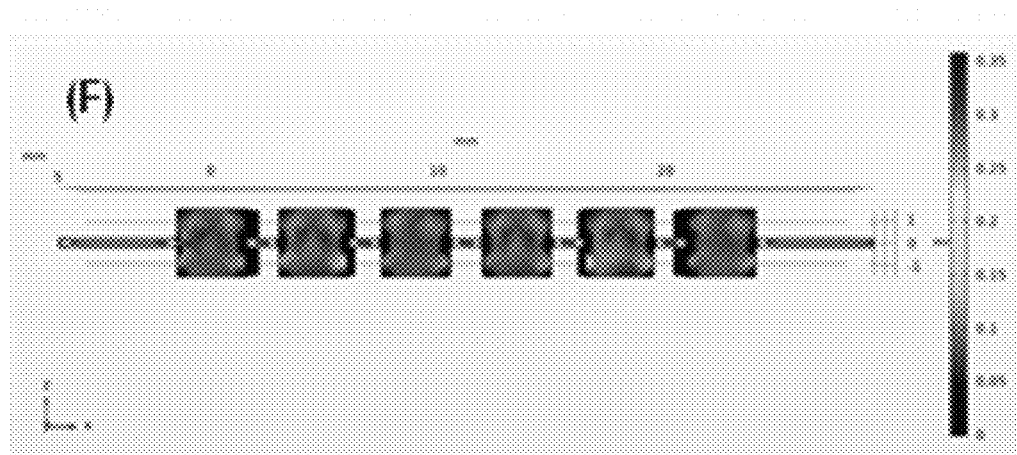
FIG. 21F shows velocity profiles in perfusion wells and microchannels simulated with COMSOL Multiphysics software.
Figure 21G:
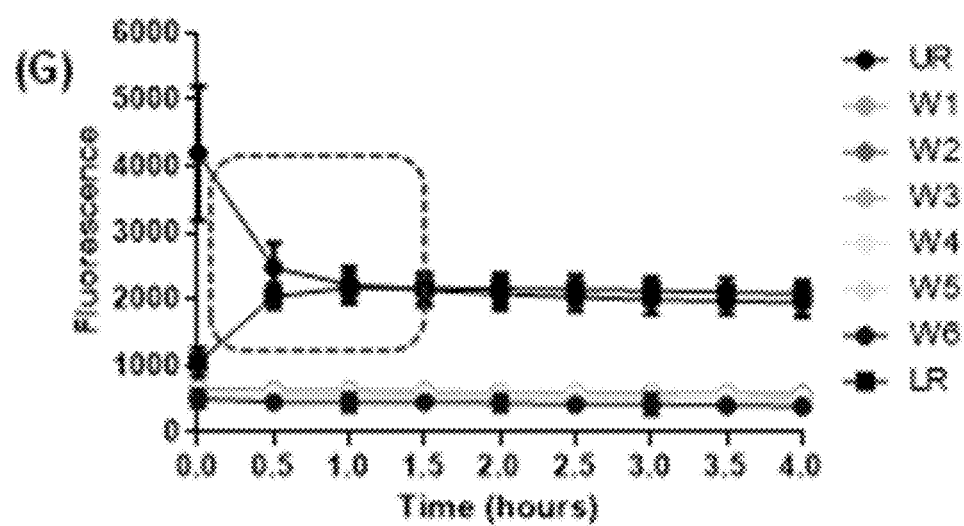
FIG. 21G shows flow rates measured with 2 $\mu M$ rhodamine B-dextran in a polydopamine-functionalized 36PerfusionPlate sandwiched with the 36PillarPlate.

With reference to FIGS. 21A-E, the combination of a pillar plate and a perfusion well plate for dynamic organoid culture is illustrated in accordance with various embodiments. SolidWorks designs of a 36PillarPlate (FIG. 21A), a 36PerfusionPlate (FIG. 21B), and the 36PillarPlate sandwiched onto a 36PerfusionPlate (FIG. 21C). Injection molding with polystyrene was performed to manufacture the 36PillarPlate (FIG. 21D), and the 36PerfusionPlate (FIG. 21E) for dynamic organoid culture. The culture media added into the upper reservoirs can flow through the microchannels and the perfusion wells to reach the lower reservoirs. FIG. 21F illustrates velocity profiles in perfusion wells and microchannels simulated with COMSOL Multiphysics software. The greatest velocity profiles found in and around microchannels, eliminating air bubbles. FIG. 21G illustrates the flow rates measured with 2 µM rhodamine B-dextran in a polydopamine-functionalized 36PerfusionPlate sandwiched with the 36PillarPlate. The fluid flow generated due to the height difference of growth media in the upper reservoirs and lower reservoirs. Changes in fluorescence measured by using a microtiter well plate reader represent the volume of the rhodamine solution in reservoirs and perfusion wells. The flow reached equilibrium within 1.5 hours so that bidirectional flows were generated on a digital rocker for long-term cell culture.

In addition to the 384PillarPlate and the 384DeepWellPlate, a 36PillarPlate and a 36PerfusionPlate were built on the footprint of conventional 384-well plates by injection molding with polystyrene for dynamic organoid culture. A single 36PillarPlate contains 36 pillars onto which an array of human organoids (entrapped in 1-6 µL spots of Matrigel) can be dispensed using a 3D bioprinter or a multichannel pipette. The dimension of the 36PillarPlate is identical to the 384PillarPlate except for the number of pillars. The 36PerfusionPlate complementary to the 36PillarPlate contains up to 1200 µL of growth media in each of twelve reservoirs and typically 50-70 µL solutions in 36 perfusion wells. A thin polystyrene film was attached at the bottom of the 36PerfusionPlate by ultrasonic welding to create microchannels, which connect reservoirs and perfusion wells for dynamic organoid culture and organoids communication. Each channel consists of one upper reservoir, one lower reservoir, and six perfusion wells. To control flow rates within microchannels in the 36PerfusionPlate, it was necessary to change the surface property from hydrophobic to hydrophilic using robust surface chemistry. There was no flow generated in the 36PerfusionPlate without surface functionalization due to high surface tension from the hydrophobic polystyrene surface. Hydrophilic surface functionalization was important to minimize air bubble entrapment in microchannels, which is critical for uniform organoid culture within the 36PillarPlate. To this end, the surface of the 36PerfusionPlate was functionalized with hydrophilic polydopamine, leading to uniform flow rates within microchannels (See FIG. 21G). By sandwiching the 384PillarPlate and 36PerfusionPlate together, various biochemical and cell-based assays can be performed with unidirectional or bidirectional flows generated. The optimal volume of growth media within each channel is approximately 900 µL to avoid an "overflow" after sandwiching. For dynamic organoid culture, 600 µL of old growth media can be removed from each upper reservoir and lower reservoir, which will be replaced with the same volume of fresh growth media. Velocity profiles in microchannels and perfusion wells were simulated by using COMSOL Multiphysics software (see FIG. 21F). The transport phenomenon considered in this model was the Navier-Stokes equation for free laminar flow. The geometry of the rectangular perfusion wells was designed with two reservoirs. The model assumed that the 36PillarPlate was sandwiched onto the 36PerfusionPlate. To mesh the model's geometry, the COMSOL tetrahedral mesh generator was used to calculate flow rates at different conditions. By changing the level of water in the upper reservoir and the lower reservoir (i.e., inlet and outlet pressure), the velocity profiles were constructed for the microchannels and the perfusion wells to avoid diffusion limitation of growth media on the 36 pillars. The greatest velocity profiles found in and around microchannels, eliminating air bubbles (See FIG. 27B). The volume changes in perfusion wells and reservoirs in the 36PerfusionPlate sandwiched with the 36PillarPlate over time were measured with 2 µM rhodamine B isothiocyanate-dextran dissolved in distilled water. The unidirectional fluid flow in each channel generated the height difference in reservoirs while maintaining uniform heights within perfusion wells over time (FIG. 21G). The average flow rates achieved was approximately 2 µL/min by simply adding growth media in upper reservoirs and removing in lower reservoirs without using pumps and tubes.

Example 7

Figure 22A:
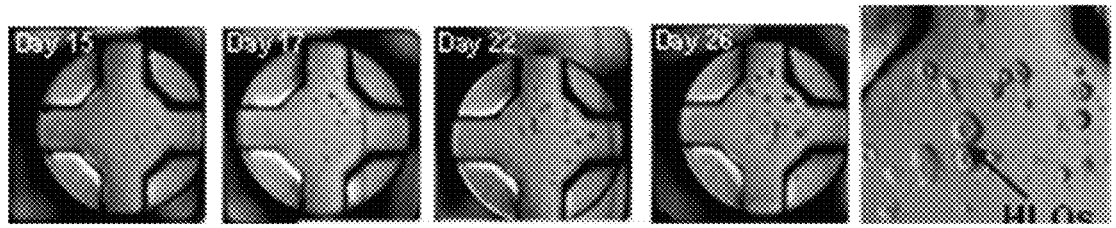
FIG. 22A shows bioprinted frozen foregut cells encapsulated in Matrigel on the 36PillarPlate differentiated and matured into HLOs for four weeks.
Figure 22B:
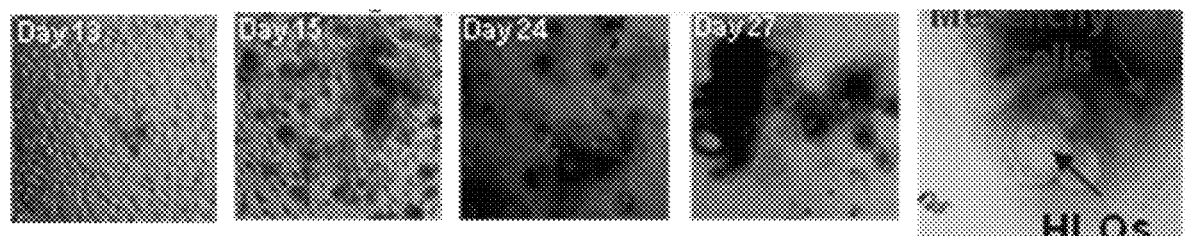
FIG. 22B shows frozen foregut cells in Matrigel domes cultured in 48-well plates.
Figure 22C:
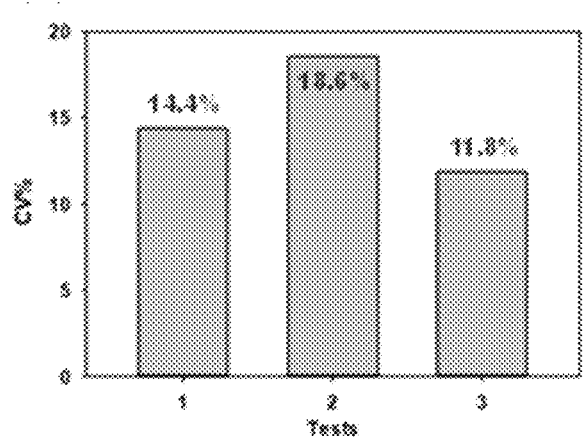
FIG. 22C shows a graphical representation of the accuracy of printing frozen foregut cell suspension in Matrigel for differentiation of HLOs on the 36PillarPlate.

With reference to FIGS. 22A-C, demonstrations of rapid cell loading strategies on the pillar plates for organoid culture are illustrated in accordance with various embodiments. Bioprinted human liver organoids (HLOs) on the pillar plate. FIG. 22A illustrates bioprinted frozen foregut cells encapsulated in Matrigel on the 36PillarPlate differentiated and matured into HLOs for four weeks. FIG. 22B illustrates frozen foregut cells in Matrigel domes cultured in 48-well plates as a control. The size of the matured HLOs was 0.2-0.4 mm. Unlike HLOs cultured on the 36PillarPlate, HLOs cultured in 48-well plates showed high levels of mesenchymal cell outgrowth, which needed to be eliminated frequently by cumbersome Matrigel dissociation and centrifugation. FIG. 22C illustrates a graphical representation of the accuracy of printing frozen foregut cell suspension in Matrigel for differentiation of HLOs on the 36PillarPlate. To calculate the coefficient of variation (CV) of bioprinting on pillars, viability of frozen foregut cells in Matrigel was measured using CellTiter-Glo® luminescent cell viability assay kit after cell printing. The low CV values at different trials indicate uniform cell printing on the pillar plate.

Figure 23A:
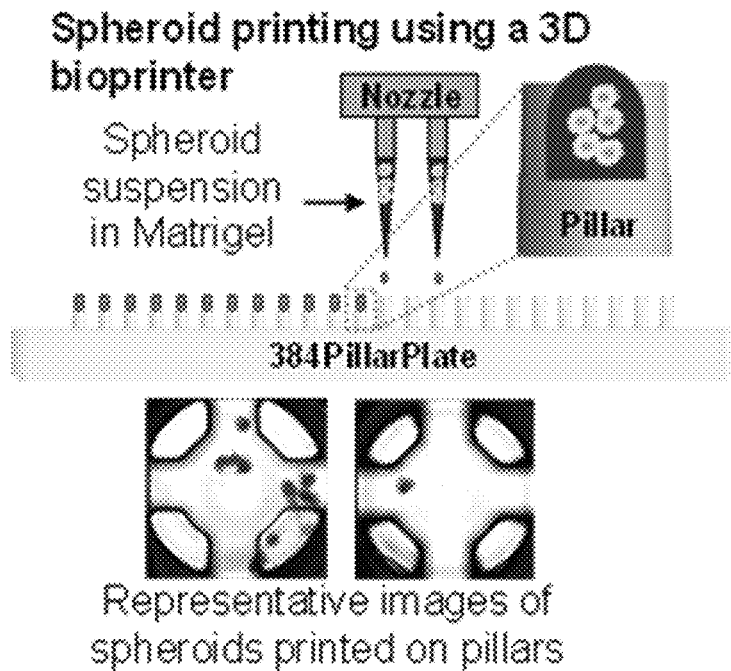
FIG. 23A shows spheroid printing using a 3D bioprinter.

To establish organoid proliferation, differentiation, and function on the pillar/perfusion plate platforms successfully, the choice of iPSCs at different stages, biomimetic hydrogels, and growth media with specific cocktails of growth factors and additives were made. In particular, the differentiation stages of iPSCs and aggregation of iPSCs are important for successful creation of human organoids. For example, mature tumor organoids could be dissociated into single cells, dispensed in Matrigel, and cultured into a full size of organoids. Thus, it could be more compatible with automated liquid handling machines and more amenable to HTS. However, organoids derived from iPSCs such as intestine organoids and brain organoids require cell-to-cell contact by creating cell aggregates prior to encapsulation in biomimetic hydrogels. These cell aggregates can be difficult to dispense using conventional liquid handling machines due to rapid precipitation in growth media. In addition, most liquid handling machines are incapable of robustly dispensing cells in hydrogels, in particular, temperature-sensitive hydrogels such as Matrigel due to lack of a chilling dispensing head. To address these issues and successfully dispense single cells and cell aggregates suspended in biomimetic hydrogels, miniature 3D bioprinting technology and associated pillar/perfusion plate platforms were developed. Briefly, single cells and cell aggregates suspended in Matrigel were printed on the pillar plates using a 3D bioprinter with a chilling printing head equipped with microsolenoid valves and custom-made 600 µm orifice nozzles (see FIGS. 22A-C and 23A-B). The differentiation stages of iPSCs for miniature 3D bioprinting were selected based on the timing of cell encapsulation in hydrogels, success rates of cryopreservation, and efficiency of mass production of cells. For HLOs, frozen foregut cells were thawed, suspended in Matrigel, and printed rapidly (within 3 minutes) on the pillar plates. For HIOs, frozen hindgut cells were thawed and added in an AggreWell Plate™ 400 6-well plate to create cell aggregates, which were followed by suspension in Matriel and rapid printing on the pillar plates (FIG. 23A). Several biomimetic hydrogels can be used for organoid cultures, including Matrigel, which is widely used in organoid culture. To successfully print single cells and cell aggregates suspended in hydrogels and minimize sheer stress and clogging, viscosity of hydrogels, cell seeding density, simplified channel structure in the microsolenoid valve, large orifice of the nozzle, pre-pressurization of syringe pumps, and valve open time were optimized. Foregut cells were suspended in 2-fold diluted Matrigel on ice (typically 6 mg/mL), and the mixture was dispensed onto the 36PillarPlate (6×6 replicates per plate, triplicate spots) on a chilling deck using a 3D bioprinter (ASFA™ spotter from MBD Korea). The printed cell spots in Matrigel (typically 5 µL) were gelled by sandwiching the 36Pillar-Plate onto the 384DeepWellPlate with 30 µL of growth medium in each well and incubating them in a humid chamber at 37° C. for 20 minutes (see FIG. 25A). This is followed by separating the 36PillarPlate and sandwiching with the 384DeepWellPlate containing 80 µL of differentiation and maturation media over time to mimic the liver differentiation process (FIG. 26A). The culture media were replaced every 2 days, and the cells were cultured for up to 4 weeks. To measure reproducibility of cell printing and organoid formation on the pillar plates, the coefficient of variation (CV) was measured 1 day after cell printing and 21 days after cell differentiation and maturation by measuring cell viability with CellTiter-Glo® luminescent cell viability assay kit and liver function with an albumin secretion assay. Changes in drug-metabolizing enzyme (DME) expression were monitored by P450-Glo® assay kit.

Example 8

Figure 23B:
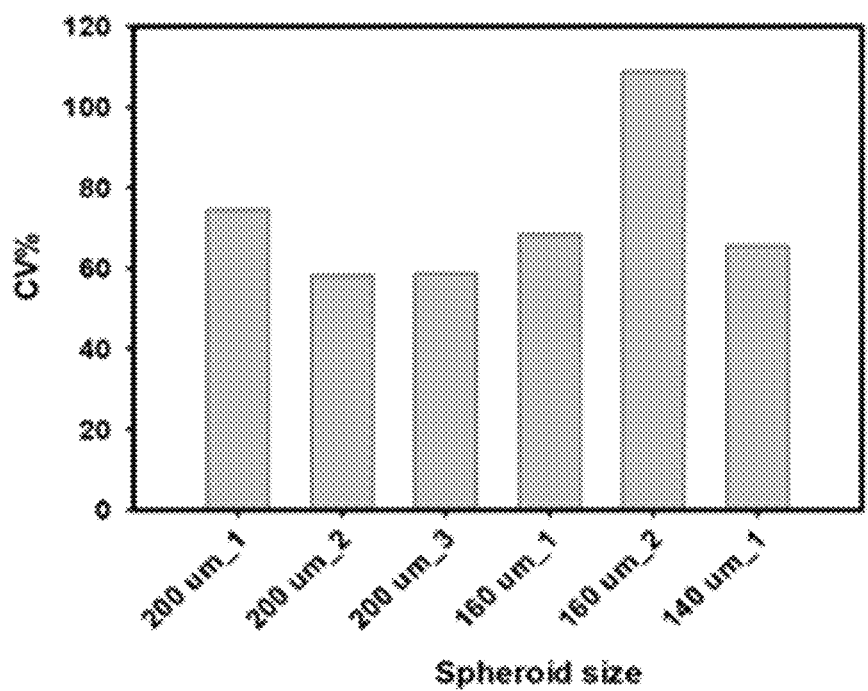
FIG. 23B shows a graphical representation of the coefficient of variation of bioprinting on pillars for different spheroid sizes.

With reference to FIGS. 23A-B, accuracy of printing frozen posterior foregut endoderm spheroids in Matrigel for differentiation of human intestine organoids (HIOs) on the 384PillarPlate are described herein. To calculate the coefficient of variation (CV) of bioprinting on pillars, the number of spheroids on pillars after printing was counted under the bright-field microscope. The high CV values at different trials indicate unreliable spheroid printing on the pillar plate presumably due to difficulty in maintaining the homogenous suspension of spheroids in Matrigel during printing.

Example 9

Figure 24A:
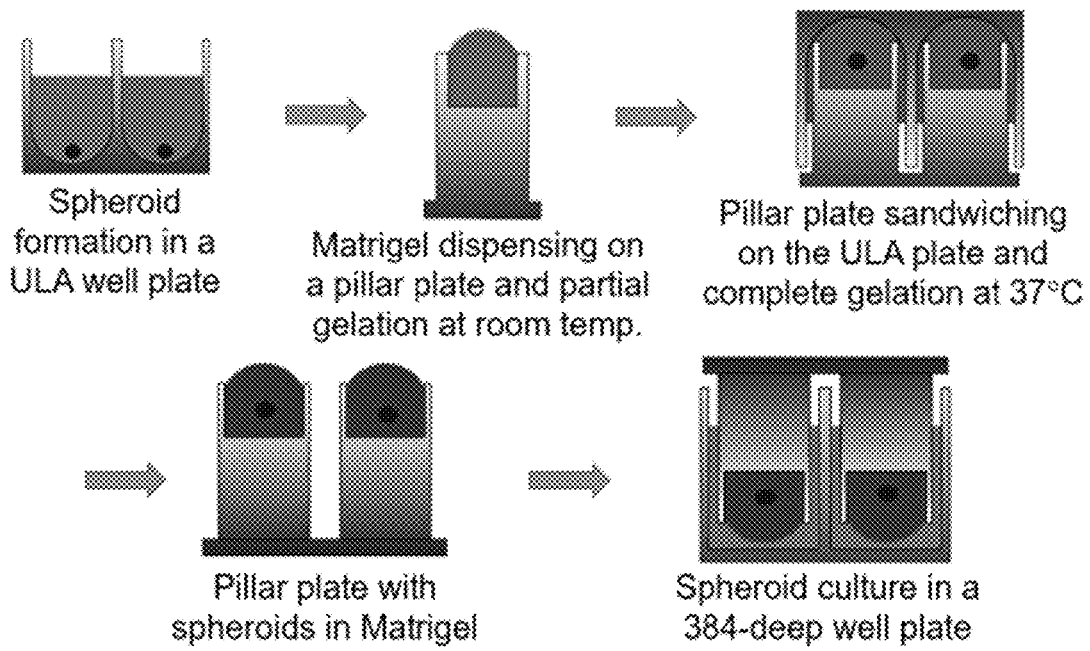
FIG. 24A shows experimental procedure of using spheroid transfer.
Figure 24B:
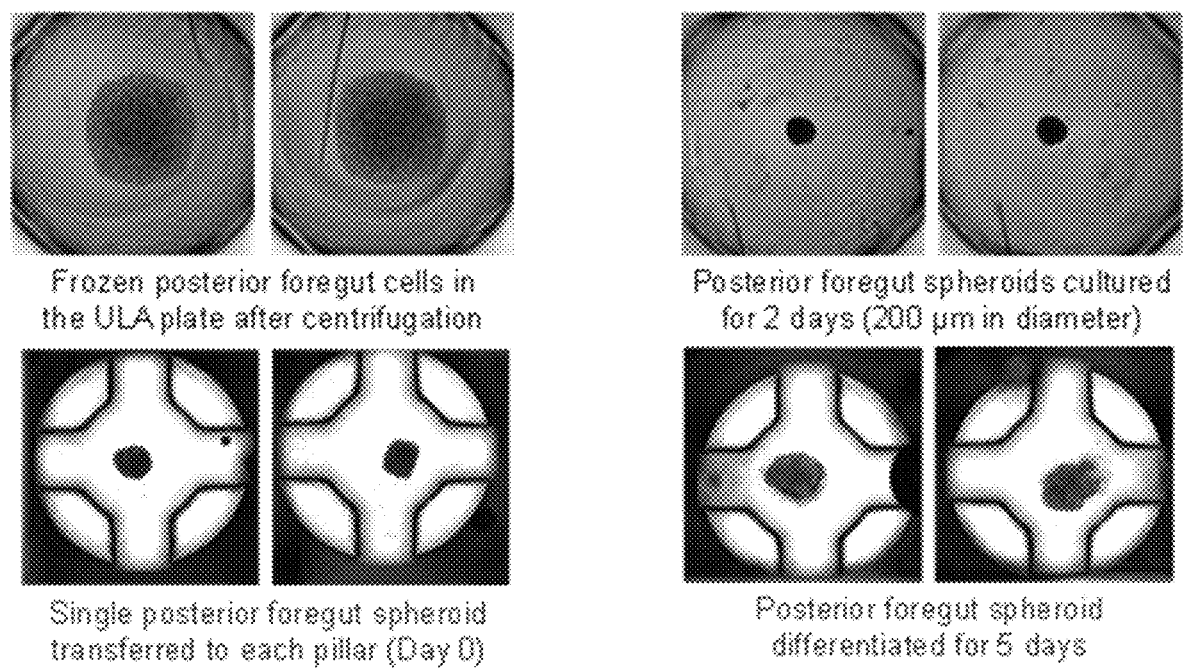
FIG. 24B shows bright-field images of frozen posterior foregut spheroids on the 384PillarPlate transferred from Nexcelom ULA 384-well plate.

With reference to FIGS. 24A-B, transferring single spheroid from an ultralow attachment (ULA) 384-well plate to the 384PillarPlate for uniform differentiation of HIOs on the pillar plate is illustrated. FIG. 24A illustrates an experimental procedure of spheroid transfer. FIG. 24B illustrates bright-field images of frozen posterior foregut spheroids on the 384PillarPlate transferred from Nexcelom ULA 384-well plate. Single spheroid in diameter of 200 µm was robustly transferred from the ULA 384-well plate to the 384PillarPlate (95-100% success rate achieved reproducibly). Transferred spheroids were all viable and uniform.

Example 10

Fabrication of pillar/perfusion plates: The 384PillarPlate, the 384DeepWellPlate, the 36PillarPlate, and the 36PerfusionPlate (see, for example, the FIGS. 20A-E and 21A-E) were manufactured by plastic injection molding using an injection molder (Woojin SM130, South Korea). Metal molds were made of carbon steel by using a CNC milling machine (Hwa Cheon, South Korea). The 384PilllarPlate and the 36PillarPlate, made of polystyrene, contain 384 pillars and 36 pillars (4.5 mm pillar-to-pillar distance, 11.6 mm pillar height, and 2.5 mm outer and 1.5 mm inner diameter of pillars), respectively. The 384DeepWellPlate and the 36PerfusionPlate, made of polystyrene, have 384 complementary wells (3.5, 3.5, and 14.7 mm well width, length and depth, and 4.5 mm well-to-well distance) and 36 wells (3.4, 3.4, and 11.9 mm well width, length and depth, and 4.5 mm well-to-well distance) with microchannels and reservoirs, respectively. All plates which are similar in size to conventional 384-well plates (86 mm×128 mm) are commercialized by Bioprinting Laboratories Inc. (Cleveland, OH, USA).

Example 11

Functionalization of pillar/perfusion plates: To ensure robust cell spot attachment to the pillar plates, the surface of the pillar plates was coated with 0.01% (w/v) poly(maleic anhydride-alt-1-octadecene) (PMA-OD from Sigma-Aldrich, St. Louis, MO, USA). Briefly, a 0.01% (w/v) PMA-OD working solution was prepared in 50 mL conical tubes by diluting 0.1% (w/v) PMA-OD dissolved in ethanol 10-fold with ethanol and proper mixing. The pillar plates were immersed in 20 mL of the 0.01% (w/v) PMA-OD in the lid of a 384-well plate and then dried in a sterile bioassay plate at room temperature for 2-3 hours. For robust spot attachment by ionic interactions and gelation with alginate, a 3 µL mixture of 0.0033% poly-L-lysine (PLL from Sigma-Aldrich) and 25 mM calcium chloride ($CaCl_2$ from Sigma-Aldrich) was printed on each pillar of the PMA-OD-coated pillar plates using a 3D bioprinter (ASFA™ spotter from MBD Korea, Suwon, South Korea). After drying overnight, 5 µL of 0.75% low-viscosity alginate (Sigma-Aldrich) was printed on each pillar of the PLL-$BaCl_2$-treated pillar plate and dried for 30 minutes at room temperature. The alginate coating provided for robust attachment of Matrigel with cells while reducing air bubble entrapment and 2D cell growth on top of the pillars.

Example 12

Simulation of flow patterns within the perfusion plate using COMSOL Multiphysics: To ensure uniform mixing and avoid diffusion limitation on the pillars inserted in the perfusion wells at relatively slow flow rates, a 3D computational model for the flow rate and profile has been developed using the COMSOL software package (COMSOL Multiphysics® 5.0, Stockholm, Sweden). To estimate the fluid dynamics within the 36PerfusionPlate, the transport phenomenon was simulated using a simplified version of the incompressible Navier-Stokes equation below:

$$\rho \frac{du}{dt} = -\nabla P + \mu \nabla^2 u$$

$$\nabla \cdot u = 0$$

where, $\rho$ is water density at 37° C. (9934 kg/m3), u is flow rate (m/s), P is pressure at 1 cm water height in the UR (100 Pa), and $\mu$ is dynamic viscosity of water at 37° C. (6.9×10−4 Pa·s). This simplified equation was used because of the low Reynold's number in the 36PerfusionPlate. The geometry of the 36PerfusionPlate was simplified to model only six rectangular perfusion wells with two reservoirs in a single row connected by microchannels. The microchannels have a dimension of 0.4 mm×0.4 mm. In addition, the model assumed that the 36PillarPlate is sandwiched onto the 36PerfusionPlate. There is a 0.5 mm gap from the bottom of perfusion wells to the top of pillars. In addition, it was assumed that the water-air boundary at the top of the perfusion wells acted as a wall. To mesh the model's geometry, the COMSOL tetrahedral mesh generator was used to calculate flow rates at different conditions. By changing the level of water in the UR and the LR (i.e., inlet and outlet pressure), the velocity profiles within the microchannels and the perfusion wells were determined to avoid diffusion limitation of growth media on the 36 pillars.

Example 13

Measurement of flow rates within the perfusion plate: The change of the water level in the 36PerfusionPlate was measured with a fluorescent dye. Briefly, the dopamine-functionalized 36PerfusionPlate was placed on a flat surface, and then 900 µL of 2 µM rhodamine B isothiocyanate-dextran dissolved in distilled water was added in the upper reservoir. After covering the 36PerfusionPlate with aluminum foil to avoid light exposure and waiting 1 hour until reaching an equilibrium, the 36PillarPlate was sandwiched onto the 36PerfusionPlate. After waiting additional 1 hour until the water level in the perfusion wells reaching equilibrium, 300 µL of 2 µM rhodamine B isothiocyanate-dextran was added in the upper reservoir, and then immediately 300 µL of the rhodamine B solution was removed from the lower reservoir. The change of the water level in the reservoirs and the perfusion wells due to gravity-driven flow was immediately recorded by measuring the changes in fluorescence intensity using a microtiter well plate reader (Synergy H1, BioTek Instrumentation, Inc.) at an excitation wavelength of 553 nm and an emission wavelength of 627 nm.

Example 14

Bioprinting of foregut cells suspended in Matrigel on the pillar plate to create human liver organoids (HLOs): HLOs were generated on the pillar plates with modified protocols previously described (FIG. 26A). Briefly, definitive endoderm was generated on day 3 by differentiating multiple iPSCs using 50 ng/mL bone morphogenetic protein 4 (BMP4) and 100 ng/mL Activin A along with 0.2% fetal bovine serum (FBS) on day 2. This was followed by inducing foregut cells and budded spheroids using 500 ng/mL fibroblast growth factor 4 (FGF4) and 3 µM CHIR99021 (GSK3 inhibitor). Foregut cells were collected with mesenchymal cells by gentle pipetting and mixed with Matrigel™ matrix (Corning Inc., NY, USA) on ice to achieve a final concentration of 750,000 cells/mL suspended in Matrigel. The mixture of cells and Matrigel was printed on top of the alginate-coated 36PillarPlate at a volume of 4 (3000 cells per pillar) using the 3D bioprinter while maintaining the slide deck at 4° C. to prevent water evaporation during printing. For Matrigel gelation, each 36PillarPlate was placed in petri dish containing a few droplets of water for maintaining high humidity and incubated in a 5% $CO_2$ incubator at 37° C. for 15-20 minutes. For HLO formation, the 36PillarPlate was sandwiched onto a 384DeepWellPlate containing 80 µL of organoid formation medium in advanced DMEM/F12 with 2% B27, 1% $N_2$, 10 mM HEPES, 1% Glutamax or L-glutamine, 1% Pen/Strep, 5 ng/mL fibroblast growth factor 2 (FGF2), 10 ng/mL vascular endothelial growth factor (VEGF), 20 ng/mL epidermal growth factor (EGF), 3 µM CHIR99021, 0.5 µM A83-01, and 50 µg/mL ascorbic acid, and incubated in the CO2 incubator for 4 days with medium change every 2 days. For HLO differentiation, the 36PillarPlate was separated and sandwiched onto another 384DeepWellPlate containing 80 µL of differentiation medium in advanced DMEM/F12 with 2% B27, 1% N2, 10 mM HEPES, 1% Glutamax or L-glutamine, 1% Pen/Strep, and 2 µM retinoic acid (RA), and incubated in the CO2 incubator for 4 days with medium change every 2 days. To promote the polarization of organoids and increase size and complexity of the bile canaliculi and the pericanalicular sheaths, the encapsulated cells were incubated with retinoic acid (RA). After RA treatment, HLOs were matured in hepatocyte maturation medium in hepatocyte culture medium (Lonza, catalog no. CC-3198) with 10 ng/mL hepatocyte growth factor (HGF), 0.1 µM dexamethasone, and 20 ng/mL oncostatin M (OSM).

Example 15

Figure 26A:
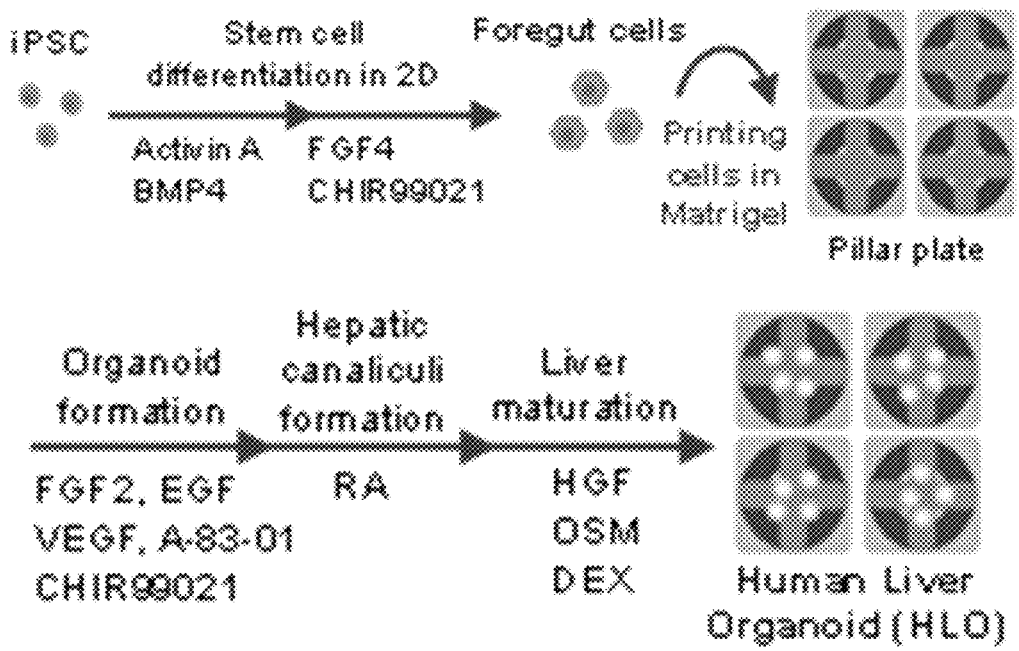
FIG. 26A shows steps necessary for human liver organoid generation and timing considered for cell printing.
Figure 26B:
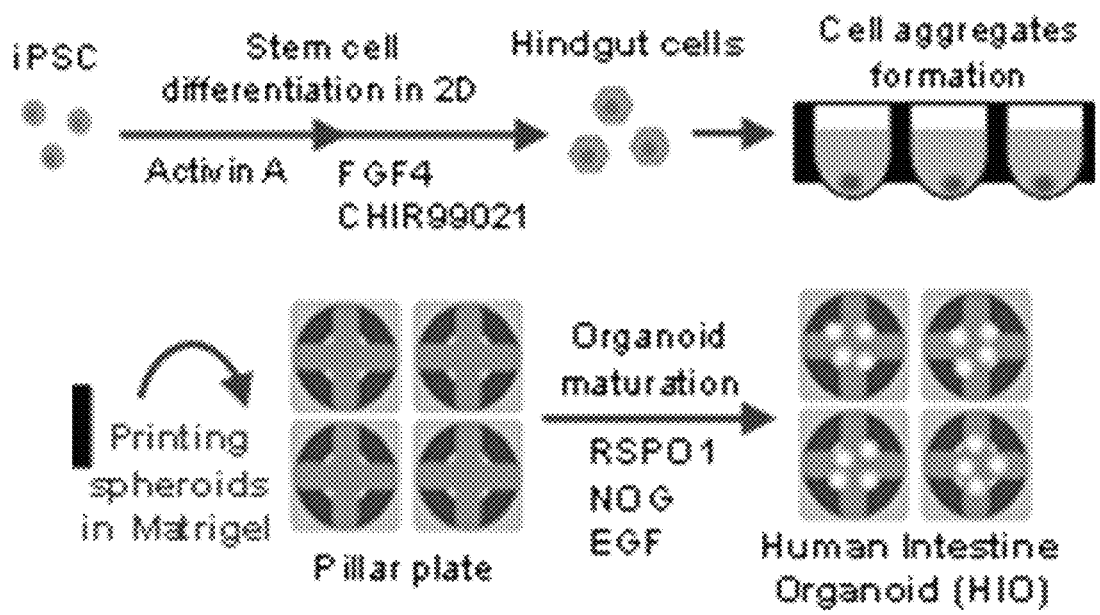
FIG. 26B shows steps necessary for human intestine organoid generation and timing considered for cell printing.

Bioprinting of hindgut cell aggregates suspended in Matrigel on the pillar plate to create human intestine organoids (HIOs): HIOs were generated on the pillar plates with modified protocols previously described (FIG. 26B). Briefly, iPSCs generated at Cincinnati Children's Hospital Medical Center were maintained in mTeSR (StemCell Technologies) in monolayer and passaged every 7 days using Gentle Cell Dissociation Reagent (StemCell). PSCs were treated with Accutase (StemCell) and plated on to 24-well plates coated with ESC-qualified Matrigel (Corning) in mTeSR supplemented with Y-27632 (Vendor). PSCs were then differentiated into definitive endoderm by treatment with 100 ng/mL Activin A (R&D) and 15 ng/mL BMP4 (R&D) in RPMI supplemented with nonessential amino acids (NEAA, Gibco) for 1 day, followed by 100 ng/mL Activin A in RPMI with NEAA and 0.2% FBS (Gibco) for 1 day, and 100 ng/mL Activin A in RPMI with NEAA and 2% FBS for 1 day. The resulting definitive endoderm was subjected to 3 µM CHIR 99021 and 500 ng/mL FGF4 (R&D) in RPMI with NEAA and 2% FBS for 4 days. The resulting hindgut cell monolayer was dissociated using Accutase for 8-10 minutes. The resulting single cell suspension was either frozen in Cell Banker 1 (amsbio) or resuspended in Gut media (consisting of Advanced DMEM/F12 with N2, B27, 15 mM HEPES, 2 mM L-gluamine, 100 UI/mL penicillin/streptomycin) supplemented with 100 ng/mL EGF (R&D) and ROCK inhibitor Y-27632. The resulting single cell suspension was aggregated using AggreWell™ 400 plates (StemCell) with each aggregate consisting of approximately 3000 cells. For HIO culture on the pillar plate, hindgut cell aggregates were mixed with Matrigel™ matrix (Corning) on ice to achieve a concentration of aggregates suspended in Matrigel. The mixture of cell aggregates and Matrigel was printed on top of the alginate-coated 36PillarPlate at a volume of 5 µL. After Matrigel gelation, the 36PillarPlate was sandwiched with a 384DeepWellPlate containing 80 µL of Gut media per well and incubated in the $CO_2$ incubator with medium change every 2 days. HIOs were grown in Gut media plus EGF for the remainder of culture for maturation.

Example 16

Measurement of cell viability using CellTiter-Glo® luminescent cell viability assay kit: The pillar plates with cells were sandwiched with an opaque white 384-well plate containing 20 µL of CellTiter-Glo® Reagent from CellTiter-Glo® cell viability kit (Promega, Madison, WI, USA) and 20 µL of cell culture medium in each well to measure cellular adenosine triphosphate (ATP) levels. To induce cell lysis, the sandwiched pillar/well plates were placed on an orbital shaker for 25 minutes. After stabilizing the luminescence for 15 minutes at room temperature, the luminescent signals were recorded using the microtiter well plate reader (Synergy H1) at an emission wavelength of 560 nm. A standard calibration curve was generated using ATP disodium salt (Sigma Aldrich) at a concentration range of 10 nM to 1 µM.

Example 17

Measurement of cell viability using calcein AM and ethidium homodimer-1 in static and dynamic conditions: The HLOs on the 36PillarPlate were rinsed once with a saline solution and then stained with 80 µL of a mixture of 2 µM calcein AM, 4 µM ethidium homodimer-1, and one drop of NucBlue® Live ReadyProbes® Reagent (Thermo Fisher Scientific Inc., MA, USA) in a 384DeepWellPlate for 1 hour at room temperature. After staining, the 36PillarPlate was rinsed twice with the saline solution, and fluorescent images were acquired in high throughput with Keyence BZ-X710 automated fluorescence microscope (Keyence, Osaka, Japan).

Example 18

Measurement of albumin secretion from HLOs: To measure the level of albumin secretion from HLOs on pillars, 80 µL of culture medium in the 384DeepWellPlate was collected after 24 hours of incubation with HLOs encapsulated in Matrigel on the 36PillarPlate. The culture medium was centrifuged at 1,500 rpm (250 g) for three minutes to remove any debris, and the resulting supernatant was assayed with human albumin ELISA kit (EHLAB, ThermoFisher Scientific) according to the manufacturer's instruction. To quantify the number of HLOs on each pillar and normalize the amount of albumin secreted by the HLO number, images were captured with the Keyence microscope.

Example 19

Immunofluorescence staining of whole HLOs on the pillar plate: HLOs on the 36PillarPlate were rinsed by sandwiching the 36PillarPlate onto a 384DeepWellPlate with 80 of 1×PBS at room temperature twice for 30 minutes each on a slow-speed orbital shaker. The HLOs were fixed with 80 µL of 4% paraformaldehyde (PFA) solution in a 384DeepWellPlate for 2 hours at room temperature. After washing the 36PillarPlate with 80 µL of 1×PBS in the 384DeepWellPlate at room temperature four times for 30 minutes each on the slow-speed shaker, HLOs were permeabilized with 80 µL of 2% Triton X-100 in PBS solution in a 384DeepWellPlate for 1 day at 4° C. on the slow-speed shaker. After washing the 36PillarPlate once with 80 µL of 1×PBS with 0.5% Triton X-100 in the 384DeepWellPlate at room temperature for 30 minutes on the slow-speed shaker, HLOs were exposed to 80 µL of 1×PBS with 10% normal donkey serum (NDS) and 0.5% Triton X-100 for overnight at 4° C. on the slow-speed shaker to prevent non-specific binding. For primary antibody staining, HLOs were treated with 80 µL of 200×-diluted primary antibody in 1×PBS with 1% NDS and 0.5% Triton X-100 for 1 day at 4° C. on the slow-speed shaker. To remove unbound primary antibody, HLOs were rinsed three times with 80 µL of 1×PBS with 0.5% Triton X-100 for 1 hour each at room temperature on the slow-speed shaker. For secondary antibody staining, HLOs were exposed to 80 µL of 200×-diluted, fluorophore-conjugated secondary antibody in 1×PBS with 0.5% Triton X-100 for 1 day at 4° C. on the slow-speed shaker. To remove unbound secondary antibody, HLOs were rinsed twice with 80 µL of 1×PBS for 1 hour each at room temperature on the slow-speed shaker. Finally, HLOs were stained with 80 µL of 5 µg/mL DAPI in 1×PBS for 45 minutes. After rinsing twice with 80 µL of 1×PBS for 1 hour each at room temperature, HLOs were cleared by incubating in 30 µL of 1× pre-warm (at 37° C.) RapiClear reagent (Sunjin Lab, Taiwan) in a clear flat-bottom, 384-well plate at room temperature for overnight on the slow-speed shaker. The stained and cleared HLOs were inspected under the Keyence microscope.

Example 20

Measurement of bile acid transport function in HLOs on the pillar plate by time-lapse imaging: To analyze the function of bile acid transport in HLO, HLOs on the 36PillarPlate were treated with 5 nM cholyl-lysyl-fluorescein (AAT Bioquest, Inc., CA, USA) in a 384DeepWellPlate. Time-lapse images were captured in 20-minute intervals for 16 hours using Celldiscoverer 7 (Carl Zeiss, Oberkochen, Germany) equipped with 10× objective lens at 37° C. and 5% $CO_2$. Time-lapse images obtained from the 36PillarPlate were batch-processed using ImageJ (NIH) to extract fluorescence intensity from the entire cell spots.

Example 21

Measurement of lipid accumulation in HLOs using BODIPY in static and dynamic conditions: Accumulation of lipid in HLOs on the pillar plate was measured using BODIPY® 493/503 (ThermoFisher Scientific). Briefly, HLOs on the 36PillarPlate were treated with hepatocyte maturation medium in the presence and absence of 300 µM sodium oleic acid for 72 hours. Following incubation in the 36PerfusionPlate, HLOs were rinsed three times with warm PBS to remove any residual oleic acid on the cell surface. Lipids accumulated in HLOs and cytoskeleton were stained with 2 µM BODIPY® 493/503 and 1 µM SiR-Actin (Cytoskeleton, Inc., CO, USA), respectively. Nuclei were stained with NucBlue® Live ReadyProbes® Reagent. After staining, HLOs on the 36PillarPlate were visualized and scanned using a Nikon A1 inverted confocal microscope (Japan) equipped with 10× objective lens and Keyence BZ-X710 automated fluorescence microscope. The lipid droplet volume was calculated by using ImageJ and normalized with each nucleus signal. Statistical difference in lipid accumulation between control and lipid exposure conditions was determined by Student's t-test. Statistically significant difference between control and test conditions was indicated by * for P<0.05,  for P<0.01, and * for P<0.001.

Example 22

Immunofluorescence staining of whole HLOs on the pillar plate: HIOs on the 36PillarPlate were rinsed by sandwiching the 36PillarPlate onto a 384DeepWellPlate with 80 μL of 1×PBS at room temperature twice for 30 minutes each on a slow-speed orbital shaker. The HIOs were fixed with 80 μL of 4% paraformaldehyde (PFA) solution in a 384DeepWellPlate for 2 hours at room temperature. After washing the 36PillarPlate with 80 μL of 1×PBS in the 384DeepWellPlate at room temperature four times for 30 minutes each on the slow-speed shaker, HIOs were permeabilized with 80 μL of 2% Triton X-100 in PBS solution in a 384DeepWellPlate for 1 day at 4° C. on the slow-speed shaker. After washing the 36PillarPlate once with 80 μL of 1×PBS with 0.5% Triton X-100 in the 384DeepWellPlate at room temperature for 30 minutes on the slow-speed shaker, HIOs were exposed to 80 μL of 1×PBS with 10% normal donkey serum (NDS) and 0.5% Triton X-100 for overnight at 4° C. on the slow-speed shaker to prevent non-specific binding. For primary antibody staining, HIOs were treated with 80 μL of 200×-diluted primary antibody in 1×PBS with 1% NDS and 0.5% Triton X-100 for 1 day at 4° C. on the slow-speed shaker. To remove unbound primary antibody, HIOs were rinsed three times with 80 μL of 1×PBS with 0.5% Triton X-100 for 1 hour each at room temperature on the slow-speed shaker. For secondary antibody staining, HIOs were exposed to 80 μL of 200×-diluted, fluorophore-conjugated secondary antibody in 1×PBS with 0.5% Triton X-100 for 1 day at 4° C. on the slow-speed shaker. To remove unbound secondary antibody, HIOs were rinsed twice with 80 μL of 1×PBS for 1 hour each at room temperature on the slow-speed shaker. Finally, HIOs were stained with 80 μL of 5 μg/mL DAPI in 1×PBS for 45 minutes. After rinsing twice with 80 μL of 1×PBS for 1 hour each at room temperature, HIOs were cleared by incubating in 30 μL of 1× pre-warm (at 37° C.) RapiClear reagent (Sunjin Lab, Taiwan) in a clear flat-bottom, 384-well plate at room temperature for overnight on the slow-speed shaker. The stained and cleared HIOs were inspected under the Keyence microscope.

Example 23

Dynamic secretion of ghrelin from HIOs in the 36PerfusionPlate: HIOs were generated using PSC lines containing a neurogenin-3 inducible construct to increase differentiation of enteroendocrine cells. After 24-hour doxycycline treatment, HIOs were cultured in 24-well plates for an additional 5 days. On the 6th day, HIOs were re-encapsulated in undiluted Matrigel and manually pipetted into the 36PillarPlate in 6 μL volumes. The 36PillarPlate was then inverted and combined with the 36PerfusionPlate and incubated at 37° C. for 5 minutes before the addition of Gut media with EGF. Following overnight culture in the 36PillarPlate/36PerfusionPlate, HIOs were rinsed several times with warm PBS to remove residual media. HIOs were then subjected to nutrient challenges by first loading the upper reservoir (UR) with 600 μL of 3 mM glucose in Krebs-Ringer Bicarbonate (KRB). After 30 minutes, 100 μL was removed from the lower reservoir (LR) and then 100 μL of fresh 3 mM glucose in KRB was added to the UR to maintain a constant flow rate. This was repeated every 30 minutes for a total of 2 hours in 3 mM glucose. All media was aspirated after 2 hours, and the process was repeated with 20 mM glucose in KRB for 3 hours. All samples were immediately frozen at −80° C. until analysis. KRB consisting of 140 mM NaCl, 0.15 mM Na2HPO4, 5 mM NaHCO$_3$, 1 mM MgSO4, 4.6 mM KCl, 2 mM CaCl2, 0.05% BSA, and 30 mM HEPES, pH 7.4. was prepared freshly the day of or before nutrient challenges. Undiluted sample buffer was assayed for Ghrelin content using Ghrelin human ELISA kit (ThermoFisher) according to manufacturer specifications.

Example 24

Calculation of the IC$_{50}$ value: Since the background luminescence of completely dead cells (following treatment with 70% methanol for 1 hour) was negligible due to background subtraction, the percentage of live HLOs was calculated using the following equation:

$$\% \text{ Live cells} = \left[\frac{L_{Drug}}{L_{Max}}\right] \times 100$$

where $L_{Drug}$ is the luminescence intensity of HLOs exposed to nefazodone and $L_{Max}$ is the luminescence intensity of fully viable HLOs (control).

To produce a conventional sigmoidal dose-response curve with response values normalized to span the range from 0% to 100% plotted against the logarithm of test concentration, the luminescence intensities of all HLO spots were normalized with the luminescence intensity of a 100% live HLO spot (HLOs contacted with no compound) and converted the test compound concentration to their respective logarithms using Prism 8 (GraphPad Software, San Diego, CA). The sigmoidal dose-response curve (variable slope) and IC$_{50}$ value (i.e., concentration of nefazodone where 50% of HLO viability inhibited) were obtained using the following equation:

$$Y = \text{Bottom} + \left[\frac{\text{Top} - \text{Bottom}}{1 + 10^{(LogIC_{50} - X) \times H}}\right]$$

where IC$_{50}$ is the midpoint of the curve, H is the hill slope, X is the logarithm of test concentration, and Y is the response (% live cells), starting from the top plateau (Top) of the sigmoidal curve to the bottom plateau (Bottom).

Example 25

Calculation of the Z' factor and the coefficient of variation (CV): To establish the robustness of the assays on the pillar plates, the reproducibility and range of error were measured using the Z' factor and the coefficient of variation (CV). The Z' factor can be explained by the following equation:

$$Z' = \frac{(Avg_{Max} - 3SD_{Max}) - (Avg_{Min} + 3SD_{Min})}{Avg_{Max} - Avg_{Min}}$$

where $Avg_{Max}$ is the average of all maximum luminescence intensity from fully viable cells on the pillar plate, $SD_{Max}$ is the standard deviation of maximum luminescence intensity, Avg$_{Min}$ is the average of all minimum luminescence intensity from the dead cells affected by the highest dose of toxic compound, and SD$_{Min}$ is the standard deviation of minimum luminescence intensity.

The CV is the ratio of the standard deviation (SD) to the average (Avg). It represents variability in relation to the average signal strength, thus the inverse of the signal-to-noise ratio.

$$CV = \frac{SD}{Avg} \times 100$$

Example 26

Figure 25A:
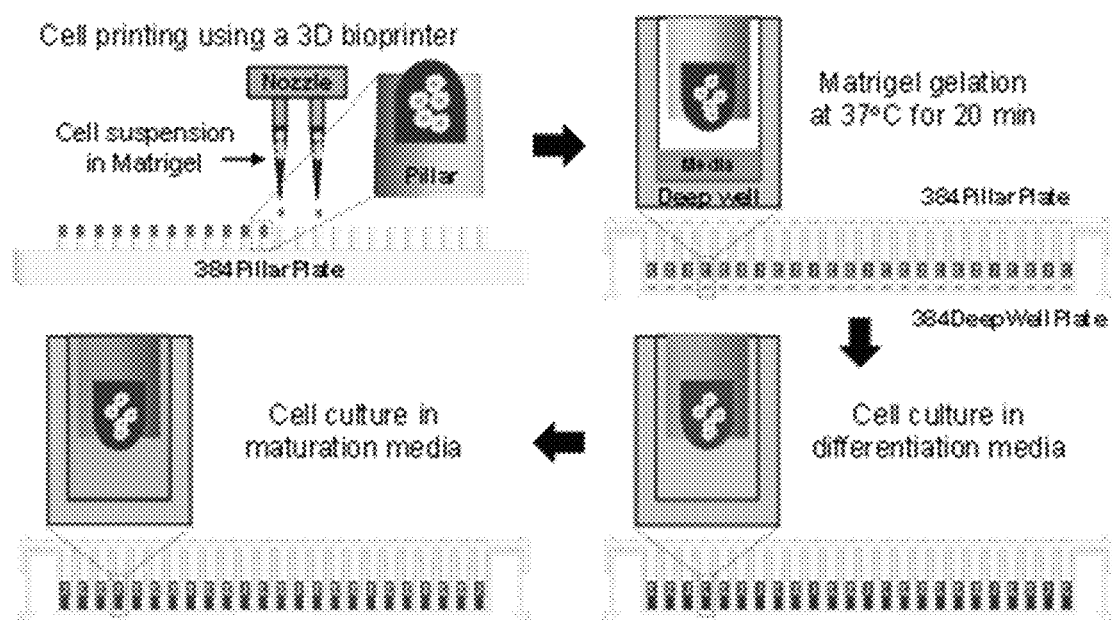
FIG. 25A shows experimental procedures for cell printing and organoid culture on the pillar plate.
Figure 25B:
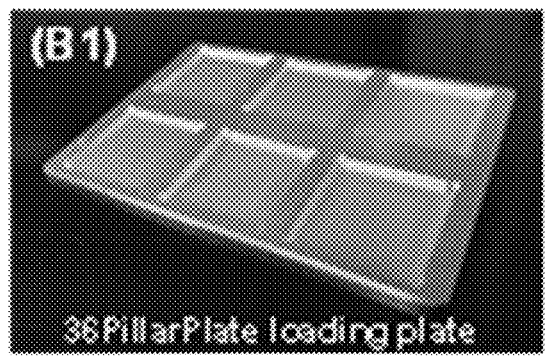
FIG. 25B shows an aluminum plate made for cell printing on the 36PillarPlate.
Figure 25C:
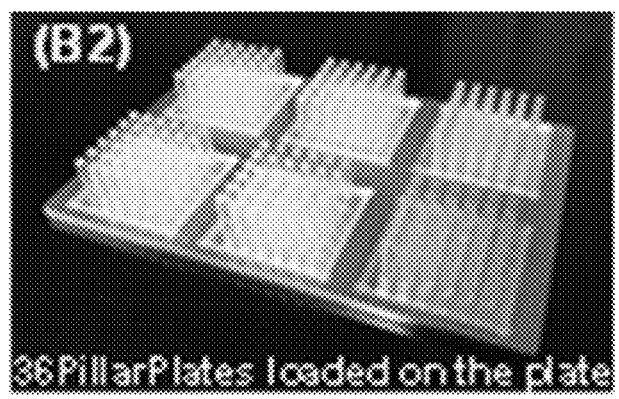
FIG. 25C shows six of 36PillarPlates loaded on the aluminum plate.
Figure 25D:
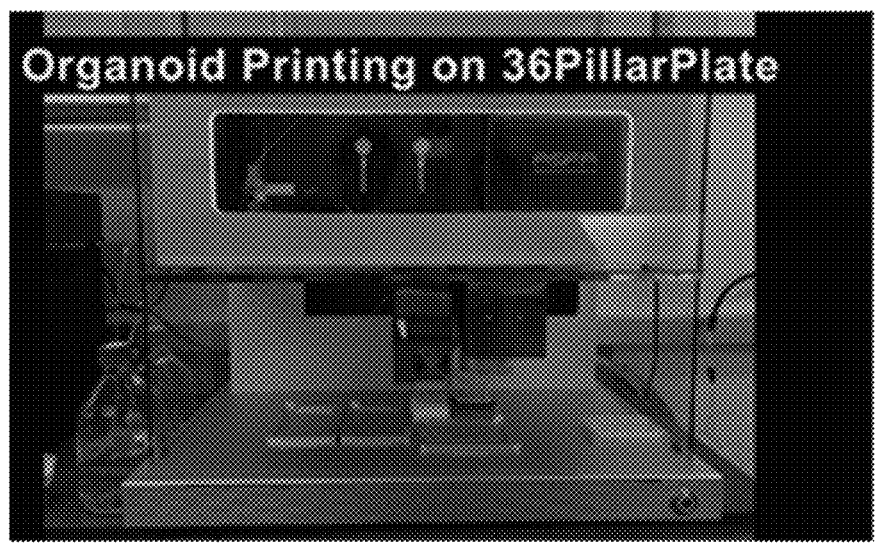
FIG. 25D shows automatic cell printing on the 36Pillar-Plate using the 3D bioprinter.
Figure 25E:
FIG. 25E shows manual cell loading on the 36PillarPlate using a multichannel pipette.

With reference to FIGS. 25A-E, experimental procedures with the 36PillarPlate/384PillarPlate and the 384DeepWellPlate are depicted. FIG. 25A illustrates experimental procedures for cell printing and organoid culture on the pillar plate. FIG. 25B-D illustrate cell printing on the 36PillarPlate. FIG. 25B shows an aluminum plate made for cell printing on the 36PillarPlate, FIG. 25C shows six of 36PillarPlates loaded on the aluminum plate, and FIG. 25D shows automatic cell printing on the 36PillarPlate using the 3D bioprinter. FIG. 25E shows manual cell loading on the 36PillarPlate using a multichannel pipette.

Example 27

With reference to FIGS. 26A-B, steps necessary for organoid generation and timing considered for cell printing are shown. FIG. 26A illustrates human liver organoids generated by printing single cell suspension. FIG. 26B illustrates human intestine organoids generated by printing cell spheroids.

Example 28

Figure 27A:
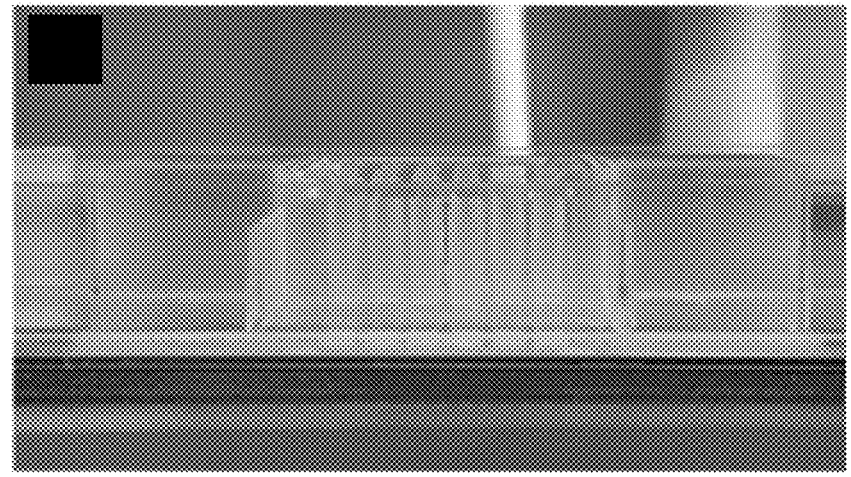
FIG. 27A shows gravity-driven flow of trypan blue dye within the 36PerfusionPlate sandwiched with the 36Pillar-Plate.
Figure 27B:
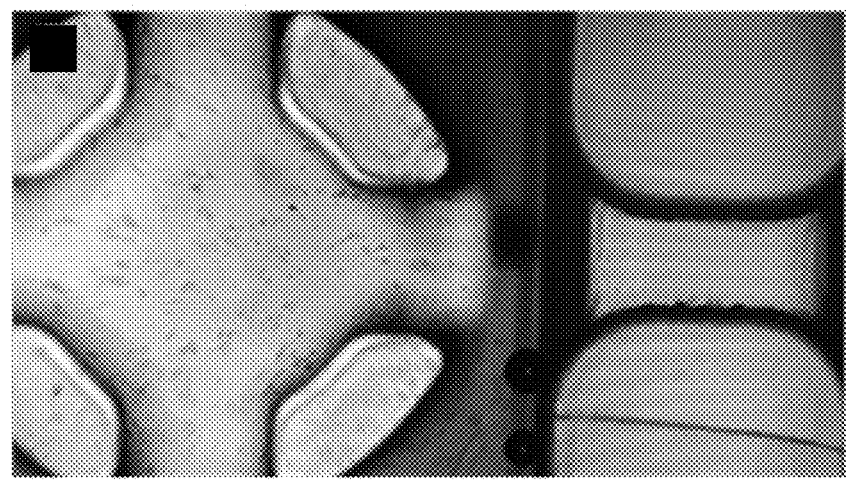
FIG. 27B shows flow of Trypan blue-stained Hep3B cells under the pillar through the microchannel in the 36PerfusionPlate.
Figure 27C:
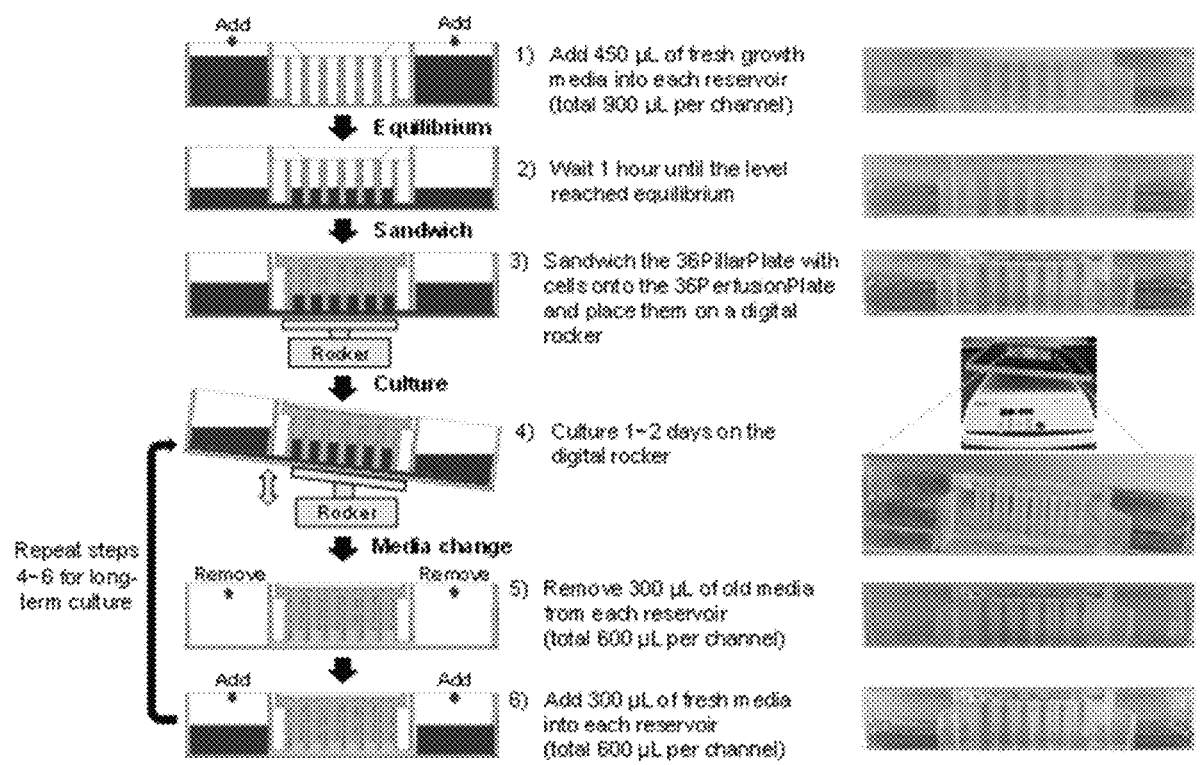
FIG. 27C shows experimental procedures for long-term dynamic organoid culture in the 36PerfusionPlate.

With reference to FIGS. 27A-C, Experimental procedures with the 36PillarPlate and the 36PerfusionPlate are depicted. FIG. 27A illustrates gravity-driven flow of trypan blue dye within the 36PerfusionPlate sandwiched with the 36PillarPlate. FIG. 27B illustrates flow of Trypan blue-stained Hep3B cells under the pillar through the microchannel in the 36PerfusionPlate. FIG. 27C shows experimental procedures for long-term dynamic organoid culture in the 36PerfusionPlate.

Example 29

With reference to various embodiments, the pillar/perfusion plate platforms (see FIGS. 20A-E and 21A-E) allow investigators/researchers to combine rapid 3D bioprinting with "microfluidic-like" features for static and dynamic organoid cultures. There are several unique features of the pillar/perfusion plates for HTS, which include high-throughput, highly reproducible, and cost-effective cell printing protocols that can be used for controlling cellular microenvironments for disease modeling. Highly reproducible, high-throughput precision printing allows testing of a variety of organoid culture conditions and individual drugs/mixtures of drugs in combination, which makes it well suited for early-stage HTS of compound libraries. The pillar/perfusion plate platforms require relatively small amounts of cells, hydrogels, ECMs, growth factors, compounds, and reagents for creating and evaluating organoids. Multiple organoids with physiologically relevant characteristics of the tissue of origin can be created on a single pillar plate by static and dynamic culture that could provide predictive insight into potential organ-specific toxicity of compounds. The pillar/perfusion plates can be manufactured by injection molding with polystyrene, which is nontoxic and has no concern for nonspecific compound adsorption. In addition, they can be optically clear for direct visualization of organoids on the pillars for in situ high-content cell staining and imaging. Cell image acquisition from bioprinted organoids is easy and straightforward because the whole sample depth fits within the focus depth of a normal objective (4×× and 10× magnification). In addition, the pillar/perfusion plates are highly flexible for biological assays with organoids. For example, organoids on the 36PillarPlate can be cultured in the 384DeepWellPlate or the 36PerfusionPlate to simulate static or dynamic conditions. Unlike traditional MPSs, the 36PillarPlate with multiple organoids can be easily detached from the 384DeepWellPlate or the 36PerfusionPlate and then sandwiched onto conventional 384-well plates containing cell-staining reagents for high-throughput assays. The 36PerfusionPlate requires no pumps and tubes that makes it easy to change growth media for long-term organoid culture as well as drug-organoid and organoid-organoid interactions. Multiple organoid types can be created on the 36PillarPlate and then connected by using the 36PerfusionPlate to simulate complex diseases with multiple organoids involved. Moreover, the pillar/perfusion plates built on the footprint of standard 384-well plates are compatible with existing HTS equipment such as fully automated fluorescent microscopes and microtiter well plate readers, which is an important feature for developing HTS assays.

Example 30

Pillar/perfusion plates can be manufactured via injection molding of polystyrene and demonstrated static and dynamic HLO and HIO culture with functional assays. The pillar/perfusion plates maintained long-term organoid culture with single cell suspensions and cell aggregates printed on the pillar plates by supporting either static culture with growth media in the deep well plate or dynamic culture with a flow of growth media through the perfusion well plate without the use of pumps and tubes. Developed cell printing and encapsulation protocols were highly flexible and allowed for culturing multiple organoids in Matrigel on the pillar plates, consequently providing more insight into potential organ-specific toxicity of compounds. The miniature 3D bioprinting technology demonstrated on the pillar/perfusion plates represent a unique and harmless method of printing PSCs and organoids in biomimetic hydrogels on the pillar plates rapidly. Human organoids on the pillar/perfusion plate platforms could recapitulate tissue development and maintain high tissue functions by mimicking in vivo microenvironments. In addition, tissue functions and mechanistic actions of compounds could be replicated and elucidated in vitro through high-throughput, high-content organoid analysis. Bioprinted organoids were combined with high-content, whole organoid imaging to better understand functions of organoids generated and cytotoxicity of compounds. Thus, the miniature 3D bioprinting technology could address the unmet need in organoid research by combining rapid printing of PSCs on the pillar plates, differentiating and maturing into organoids in static and dynamic culture to mimic the physiological microenvironment of tissues inside the human body while enhancing throughput and maneuverability dramatically for predictive screening of compounds. Bioprinted human organoids on the pillar/perfusion plates can provide highly predictive toxicity and efficacy information needed in preclinical evaluations of compounds or prioritize environmental toxicants.

The inventive aspects have been described with reference to the exemplary embodiments. Modification and alterations will occur to others upon a reading and understanding of this specification. It is intended to include all such modifications and alterations insofar as they come within the scope of the appended claims or the equivalents thereof

I claim:

1. A method of operating a perfusion plate, comprising the steps of:
   encapsulating a cell spheroid in a hydrogel on the top end of at least one pillar on a pillar plate, wherein:
   a cell spheroid is created in a well on an ultralow-attachment (ULA) well plate;
   a hydrogel is deposited into the top end of the at least one pillar on the pillar plate, wherein:
   the top end of the at least one pillar comprises an outer-wall and a base;
   the top end of the at least one pillar containing the hydrogel is inserted into the well containing the cell spheroid; and
   the pillar plate and well plate are inverted, allowing the cell spheroid to transfer from the well to the top end of the at least one pillar and encapsulate into the hydrogel;
   removing the ULA well plate from the pillar plate;
   inverting and submerging the top end of the at least one pillar having the cell spheroid encapsulated in the hydrogel into a perfusion well of a perfusion plate, wherein the perfusion plate comprises a first reservoir and a second reservoir, wherein the first reservoir and the second reservoir are fluidly connected;
   adding a first volume of media fluid to the first reservoir of the perfusion plate; and
   incubating the perfusion plate and pillar plate in an incubator for cell culture.

2. The method of claim 1, further comprising the steps of:
   adding a second volume of media fluid to the second reservoir; and
   placing the perfusion plate and pillar plate on a rocker to generate a bidirectional flow of the first volume of media fluid and the second volume of media fluid.

3. The method of claim 1, further comprising the steps of:
   removing a second volume of media fluid from the second reservoir,
   placing the perfusion plate and pillar plate on a flat surface to generate a unidirectional flow of the first volume of media fluid.

4. The method of claim 1, wherein:
   the pillar plate comprises at least a first and second row of multiple pillars;
   a first type of cell spheroid is encapsulated on the top ends of the pillars in the first row of multiple pillars; and
   a second type of cell spheroid is encapsulated on the top ends of the pillars in the second row of multiple pillars.

5. A method of loading cells from a well plate to a pillar plate, comprising the steps of:
   loading cells into a plurality of wells in an ultralow-attachment (ULA) well plate;
   adding a hydrogel to a plurality of pillar-microwells on a pillar plate;
   sandwiching the plurality of pillar-microwells on the pillar plate into the plurality of wells of the ULA well plate;
   inverting the ULA well plate and the pillar plate; and
   allowing the cells to precipitate and encapsulate into the hydrogel.

6. The method of claim 5, wherein the ULA well plate is one of a microtiter plate and a perfusion plate.

7. The method of claim 5, wherein the cells loaded into the plurality of wells of the ULA well plate comprise one or more of: human and animal cells, microbials, fungi, yeasts, and viruses.

8. The method of claim 5, further comprising the steps of:
   removing the ULA well plate from the pillar plate, and
   sandwiching the pillar plate with a second well plate having at least one well, wherein
   the second well plate is one of a ULA plate, a microtiter plate, and a perfusion plate, and wherein the cells remain incubated.

9. The method of claim 8, further comprising the steps of:
   removing the pillar plate from the second well plate;
   rotating the pillar plate 90 degrees; and
   sandwiching the pillar plate with the second well plate having at least one well to induce cell-cell communications.

* * * * *